(12) United States Patent
Friedland et al.

(10) Patent No.: US 9,963,719 B1
(45) Date of Patent: May 8, 2018

(54) SYSTEMS AND METHODS FOR ONE-SHOT GUIDE RNA (OGRNA) TARGETING OF ENDOGENOUS AND SOURCE DNA

(71) Applicant: EDITAS MEDICINE, INC., Cambridge, MA (US)

(72) Inventors: Ari E. Friedland, Boston, MA (US); Hariharan Jayaram, Cambridge, MA (US); Barrett Ethan Steinberg, Cambridge, MA (US)

(73) Assignee: EDITAS MEDICINE, INC., Cambridge, MA (US)

( * ) Notice: Subject to any disclaimer, the term of this patent is extended or adjusted under 35 U.S.C. 154(b) by 0 days. days.

(21) Appl. No.: 15/832,567

(22) Filed: Dec. 5, 2017

Related U.S. Application Data

(60) Provisional application No. 62/430,154, filed on Dec. 5, 2016, provisional application No. 62/503,640, filed on May 9, 2017.

(51) Int. Cl.
| | | |
|---|---|---|
| *C12N 15/90* | (2006.01) | |
| *C12N 9/96* | (2006.01) | |
| *C12N 9/22* | (2006.01) | |
| *C12N 15/10* | (2006.01) | |
| *C12N 15/11* | (2006.01) | |

(52) U.S. Cl.
CPC ............. *C12N 15/907* (2013.01); *C12N 9/22* (2013.01); *C12N 9/96* (2013.01); *C12N 15/102* (2013.01); *C12N 15/11* (2013.01); *C12N 2310/20* (2017.05); *C12N 2810/10* (2013.01)

(58) Field of Classification Search
None
See application file for complete search history.

(56) References Cited

U.S. PATENT DOCUMENTS 9,752,132 B2 * 9/2017 Joung .................. C12Y 301/00

FOREIGN PATENT DOCUMENTS

| WO | WO 2015/070083 A1 | 5/2015 |
| WO | WO 2015/089351 A1 | 6/2015 |
| WO | WO 2016/176404 A1 | 11/2016 |
| WO | WO 2016/183438 A1 | 11/2016 |
| WO | WO 2017/136335 A1 | 8/2017 |

OTHER PUBLICATIONS

Epstein et al., "Engineering a Self-Inactivating CRISPR System for AAV Vectors," Molecular Therapy, 24(1):S50 (2016).
International Search Report dated Feb. 21, 2018 in International Application No. PCT/us2017/064720.
Liu et al., "A chemical-inducible CRISPR-Cas9 system for rapid control of genome editing," Nature Chemical Biology, 12(11):980-987 (2016).
Moore et al., "CRISPR-based self-cleaving mechanism for controllable gene delivery in human cells," Nucleic Acids Research, Information Retrieval Ltd., 43(2):1297-1303 (2015).
Singhal et al., "Self-Inactivating Cas9: A Method for Reducing Exposure While Maintaining Efficacy in Virally-Delivered Cas9 Applications," Editas Medicine: Publications & Presentations 2017 (Apr. 24, 2017).
Retrieved from the Internet on Mar. 19, 2018: URL:http://www.editasmedicine.com/data/documents/aef_asgct_poster_2017_final_-_-present_5-11-17_515pm1_1494537387_1494558495_1497467403.pdf.
Zetsche et al., "Multiplex gene editing by CRISPR-Cpf1 through autonomous processing of a single crRNA array," bioRxiv preprint, pp. 1-15 (2016).

* cited by examiner

*Primary Examiner* — Suzanne M Noakes
*Assistant Examiner* — Jae W Lee
(74) *Attorney, Agent, or Firm* — Baker Botts L.L.P.

(57) ABSTRACT

Engineered nucleic acids encoding genome editing system components are provided, as are engineered RNA-guided nucleases that include inserts encoded in part by cellular genomic or other sequences recognized by guide RNAs.

14 Claims, 13 Drawing Sheets

SYSTEMS AND METHODS FOR ONE-SHOT GUIDE RNA (OGRNA) TARGETING OF ENDOGENOUS AND SOURCE DNA

CROSS-REFERENCE TO RELATED APPLICATION

This application claims priority to U.S. Provisional Application No. 62/430,154 filed on Dec. 5, 2016, and to U.S. Provisional Application No. 62/503,640 filed on May 9, 2017, the content of which is incorporated by reference in its entirety, and to which priority is claimed.

SEQUENCE LISTING

This application contains a Sequence Listing, which was submitted in ASCII format via EFS-Web, and is hereby incorporated by reference in its entirety. The ASCII copy, created on Dec. 4, 2017, is named 0841770163SEQLISTING.TXT and is 92,969 bytes in size.

FIELD

This disclosure relates to genome editing systems and related methods and compositions for editing a target nucleic acid sequence, or modulating expression of a target nucleic acid sequence, and applications thereof. More particularly, the disclosure relates to engineered self-regulating genome editing systems.

BACKGROUND

CRISPRs (Clustered Regularly Interspaced Short Palindromic Repeats) evolved in bacteria and archaea as an adaptive immune system to defend against viral attack. Upon exposure to a virus, short segments of viral DNA are integrated into the CRISPR locus. RNA is transcribed from a portion of the CRISPR locus that includes the viral sequence. That RNA, which contains sequence complementary to the viral genome, mediates targeting of a Cas9 protein to a target sequence in the viral genome. The Cas9 protein, in turn, cleaves and thereby silences the viral target.

Recently, the CRISPR/Cas system has been adapted for genome editing in eukaryotic cells. The introduction of site-specific double strand breaks (DSBs) allows for target sequence alteration through endogenous DNA repair mechanisms, for example non-homologous end-joining (NHEJ) or homology-directed repair (HDR).

The use of CRISPR/Cas-based genome editing systems as a tool for the treatment of inherited diseases is widely recognized. The U.S. Food and Drug Administration (FDA), for example, held a Science Board Meeting on Nov. 15, 2016, addressing the use of such systems and potential regulatory issues they may pose. In that meeting, the FDA noted that while Cas9/guide RNA (gRNA) ribonucleoprotein (RNP) complexes may be customized to generate precise edits at a locus of interest, the complexes may also interact with, and cut at, other "off-target" loci. The potential for off-target cuts ("off-targets"), in turn, raises at least a regulatory risk with respect to approval of CRISPR/Cas therapeutics.

One strategy for reducing off-target risk is to include, in a vector encoding a Cas9, a "governing guide RNA," (ggRNA) which is a guide RNA targeted to the Cas9 coding sequence. When this vector is delivered to a subject, Cas9, which might otherwise be constitutively and/or stably expressed by virally transduced cells, is expressed only transiently. Over time, the Cas9 coding domain in the vector is disrupted by cutting mediated by the governing guide RNA.

SUMMARY

The instant disclosure provides genome editing systems and related methods which adapt gRNAs targeted to specific loci to temporally limit the genome editing activity of these systems in a manner distinct from conventional ggRNAs. These adapted gRNAs are referred to as "one-shot guide RNAs" or "ogRNAs". For clarity, ogRNAs described herein can be unimolecular or modular, as discussed in greater detail below. Adaptation of gRNAs into ogRNAs is achieved by engineering cellular DNA sequences recognized by such gRNAs into nucleic acid sequences encoding an RNA-guided nuclease, e.g., a Cas9 nuclease or a Cpf1 nuclease or a vector backbone. In certain embodiments, the RNA-guided nuclease is Cas9. In certain embodiments, the RNA-guided nuclease is Cpf1.

In one aspect, this disclosure relates to an isolated nucleic acid encoding an RNA-guided nuclease, which isolated nucleic acid includes an, exogenous, substituted, inserted or engineered nucleic acid sequence, such as a eukaryotic nucleic acid sequence. The eukaryotic or otherwise exogenous sequence is generally 17 nucleotides or greater in length, and either comprises or is adjacent to a protospacer adjacent motif (PAM) that is recognized by the RNA-guided nuclease. Certain embodiments of the isolated nucleic acid also encode a gRNA (for instance, an ogRNA) having a targeting domain that is complementary to a portion of the exogenous or eukaryotic nucleic acid sequence that is adjacent to the PAM, which targeting domain is optionally greater than 16 nucleotides or 16-24 nucleotides in length. In certain embodiments, the complementarity of the targeting domain to a portion of the exogenous or eukaryotic nucleic acid sequence is sufficient to allow for modification of the nucleic acid sequence encoding the RNA-guided nuclease. In certain embodiments, the targeting domain is complementary to at least about 50%, about 60%, about 70%, about 80%, about 90%, about 91%, about 92%, about 93%, about 94%, about 95%, about 96%, about 97%, about 98%, about 99% of the exogenous or eukaryotic nucleic acid sequence. In certain embodiments, the RNA-guided nuclease is a Cas9 protein. In some embodiments, the eukaryotic nucleic acid sequence is within an RNA-guided nuclease coding sequence, where it can encode at least part of a modified portion of the protein. In instances wherein the exogenous sequence encodes all or part of a modified portion of the RNA-guided nuclease, that sequence can be positioned within a region that is flanked by codons for glycine, alanine or valine at each of its 3' and 5' ends. In some cases, the region of the RNA-guided nuclease coding sequence comprising the exogenous nucleic acid sequence encodes an amino acid having a sequence of G-(X)$_{6-10}$-G. In embodiments where the RNA-guided nuclease is Cas9, the proteins encoded by these sequences can comprise insertions (relative to SEQ ID NO: 2) such as E271_N272insGX$_{6-10}$G, L371_N372insGX$_{6-10}$G, and/or Q737_A738insGX$_{6-10}$G, and/or insertions at or near the N-terminus of a Cas9 peptide, and/or sequences of at least 95% identity (e.g. 95%, 96%, 97%, 98%, 99% or greater identity) to SEQ ID NOS: 3-5 and 10.

Continuing with this aspect of the disclosure, the isolated nucleic acid can include an insertion (relative to SEQ ID NO: 6) c.813_814insN27-36, c.1113_1114insN27-36, and/or c.2211_2212insN27-36, and/or insertions at or near the coding sequence of the N-terminus of a Cas9 peptide, and/or have at least 95% (e.g. 95%, 96%, 97%, 98%, 99% or greater identity) sequence identity to SEQ ID NOS: 7-9 and 11. The isolated nucleic acid can, alternatively or additionally include an insertion of c.157insN$_{19\text{-}36}$ and/or share at least 80% (e.g. 80%, 85%, 90%, 95%, 96%, 97%, 98%, 99% or greater identity) sequence identity with SEQ ID NO: 1. Isolated nucleic acids according to this aspect of this disclosure are optionally incorporated into vectors such as plasmids, viral vectors, naked DNA vectors, etc. In some instances, an adeno-associated virus (AAV) vector incorporates isolated nucleic acids according to this aspect of the disclosure. In certain embodiments, a target site for the gRNA is within the vector backbone. The vectors can be used to alter both a cellular endogenous target gene and the RNA-guided nuclease expression.

In certain embodiments, the RNA-guided nuclease is Cpf1. In certain embodiments, the amino acid sequence of a Cpf1 protein is set forth in SEQ ID NO: 13. In certain embodiments, the Cpf1 protein can comprise an insertion such as a GX$_{6\text{-}10}$G insertion. In certain embodiments, the insertion (relative to SEQ ID NO: 13) is positioned between amino acid positions 147 and 148, anywhere between amino acid positions 484 and 492, anywhere between amino acid positions 568 and 590, anywhere between amino acid positions 795 and 855, anywhere between amino acid positions 1131 and 1140, or anywhere between amino acid positions 1160 and 1173. In certain embodiments, the insertion is positioned at or near the N-terminus of a Cpf1 peptide. In certain embodiments, the amino acid sequence of the Cpf1 protein comprising the insertion has at least 95% sequence identity (e.g. 95%, 96%, 97%, 98%, 99% or greater identity) to SEQ ID NO: 13.

In certain embodiments, an isolated nucleic acid sequence encoding a Cpf1 protein is set forth in SEQ ID NO: 14. In certain embodiments, the isolated Cpf1 nucleic acid can comprise an insertion such as an N24-36 insertion. In certain embodiments, the insertion (relative to SEQ ID NO: 14) is positioned between nucleic acid positions 441 and 442, anywhere between nucleic acid positions 1452 and 1474, anywhere between nucleic acid positions 1704 and 1768, anywhere between nucleic acid positions 2385 and 2563, anywhere between nucleic acid positions 3393 and 3418, or anywhere between nucleic acid positions 3480 and 3517. In certain embodiments, the insertion does not alter the reading frame of the isolated Cpf1 nucleic acid. In certain embodiments, the insertion is positioned at or near the N-terminus of a Cpf1 peptide. In certain embodiments, the nucleic acid sequence of the Cpf1 protein comprising the insertion has at least 95% (e.g. 95%, 96%, 97%, 98%, 99% or greater identity) sequence identity to SEQ ID NO: 14. Isolated nucleic acids according to this aspect of this disclosure are optionally incorporated into vectors such as plasmids, viral vectors, naked DNA vectors, etc. In some instances, an adeno-associated virus (AAV) vector incorporates isolated nucleic acids according to this aspect of the disclosure. In certain embodiments, a target site for the gRNA is within the vector backbone. The vectors can be used to alter both a cellular endogenous target gene and the RNA-guided nuclease expression.

In another aspect, the disclosure relates to transiently active genome editing systems that include a guide RNA with a targeting domain that is complementary to a eukaryotic nucleotide sequence and an engineered RNA-guided nuclease encoded by a nucleic acid comprising a eukaryotic nucleic acid sequence as described above. In certain embodiments, the RNA-guided nuclease is a Cas9 protein. The gRNA and engineered Cas9 can form a Cas9/gRNA complex, which complex may in turn cleave or otherwise alter or inactivate the nucleic acid encoding the engineered Cas9 protein. In certain embodiments, the Cas9/gRNA complex can cleave a nucleic acid encoding a cellular endogenous target gene. The transiently active genome editing system can be used to alter both the cellular endogenous target and the RNA-guided nuclease expression. As discussed above, the eukaryotic nucleic acid sequence can encode, at least in part, a modified portion (e.g., amino acid insertion or substitution) of the Cas9, which modified portion has a sequence as described above. In certain embodiments, the engineered Cas9 protein has at least about 80% nuclease activity of a wild-type Cas9 protein.

In certain embodiments, the RNA-guided nuclease is a Cpf1 protein. The gRNA and engineered Cpf1 can form a Cpf1/gRNA complex, which complex may in turn cleave or otherwise alter or inactivate the nucleic acid encoding the engineered Cpf1 protein. In certain embodiments, the Cpf1/gRNA complex can cleave a nucleic acid encoding a cellular endogenous target gene. The transiently active genome editing system can be used to alter both the cellular endogenous target and the RNA-guided nuclease expression. As discussed above, the eukaryotic nucleic acid sequence can encode, at least in part, a modified portion (e.g., amino acid insertion or substitution) of the Cpf1, which modified portion has a sequence as described above. In certain embodiments, the engineered Cpf1 protein has at least about 80% nuclease activity of a wild-type Cpf1 protein In yet another aspect, the disclosure relates to a RNA-guided nuclease comprising an amino acid insertion or substitution at least partially encoded by a eukaryotic nucleic acid sequence of at least 17 nucleotides in length. In certain embodiments, the RNA-guided nuclease having the amino acid insertion or substitution has at least about 80% nuclease activity of a wild-type RNA-guided nuclease. The eukaryotic sequence can be a mammalian sequence, and/or the sequence of a human or animal subject. In certain embodiments, the RNA-guided nuclease can be a Cas9 protein and nucleic acids encoding the Cas9 protein according to this aspect of this disclosure are substantially as described above.

In another aspect, the disclosure relates to a method of altering a cell that involves delivering (e.g. contacting, administering, introducing, transfecting, transducing, etc.) a transiently expressed genome editing system as described above. In certain embodiments, the method can be used to alter a target site in a cell. In certain embodiments, the method can be used to alter both a cellular endogenous target gene and the RNA-guided nuclease expression.

In still another aspect, this disclosure relates to a kit comprising one or more components of a transiently active genome editing system, a nucleic acid and/or an RNA-guided nuclease according to the various aspects of the disclosure presented above.

BRIEF DESCRIPTION OF THE DRAWINGS

The accompanying drawings are intended to provide illustrative, and schematic rather than comprehensive, examples of certain aspects and embodiments of the present disclosure. The drawings are not intended to be limiting or binding to any particular theory or model, and are not necessarily to scale. Without limiting the foregoing, nucleic acids and polypeptides may be depicted as linear sequences, or as schematic two- or three-dimensional structures; these depictions are intended to be illustrative rather than limiting or binding to any particular model or theory regarding their structure.

DETAILED DESCRIPTION

Definitions and Abbreviations

Figure 1A:
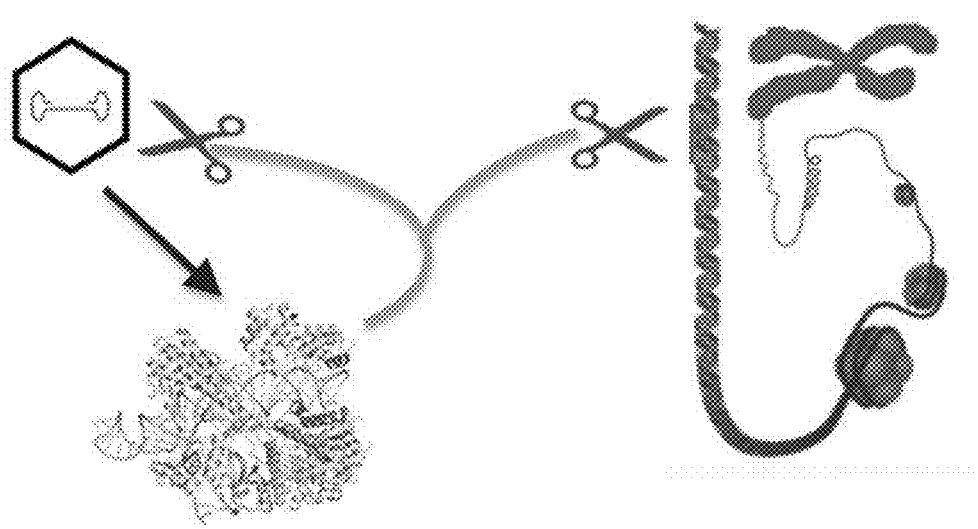
FIG. 1A is a diagram illustrating a SaCas9-gRNA complex targeting both an endogenous cellular target and a nucleic acid encoding the SaCas9 in a viral vector.

Unless otherwise specified, each of the following terms has the meaning associated with it in this section.

The indefinite articles "a" and "an" refer to at least one of the associated noun, and are used interchangeably with the terms "at least one" and "one or more." For example, "a module" means at least one module, or one or more modules.

The conjunctions "or" and "and/or" are used interchangeably as non-exclusive disjunctions.

"Domain" is used to describe a segment of a protein or nucleic acid. Unless otherwise indicated, a domain is not required to have any specific functional property.

An "indel" is an insertion and/or deletion in a nucleic acid sequence. An indel may be the product of the repair of a DNA double strand break, such as a double strand break formed by a genome editing system of the present disclosure. An indel is most commonly formed when a break is repaired by an "error prone" repair pathway such as the NHEJ pathway described below.

"Gene conversion" refers to the alteration of a DNA sequence by incorporation of an endogenous homologous sequence (e.g. a homologous sequence within a gene array). "Gene correction" refers to the alteration of a DNA sequence by incorporation of an exogenous homologous sequence, such as an exogenous single- or double-stranded donor template DNA. Gene conversion and gene correction are products of the repair of DNA double-strand breaks by HDR pathways such as those described below.

Indels, gene conversion, gene correction, and other genome editing outcomes are typically assessed by sequencing (most commonly by "next-gen" or "sequencing-by-synthesis" methods, though Sanger sequencing may still be used) and are quantified by the relative frequency of numerical changes (e.g., ±1, ±2 or more bases) at a site of interest among all sequencing reads. DNA samples for sequencing may be prepared by a variety of methods known in the art, and may involve the amplification of sites of interest by polymerase chain reaction (PCR), the capture of DNA ends generated by double strand breaks, as in the GUIDEseq process described in Tsai et al. (Nat. Biotechnol. 34(5): 483 (2016), incorporated by reference herein) or by other means well known in the art. Genome editing outcomes may also be assessed by in situ hybridization methods such as the FiberComb™ system commercialized by Genomic Vision (Bagneux, France), and by any other suitable methods known in the art.

"Alt-HDR," "alternative homology-directed repair," or "alternative HDR" are used interchangeably to refer to the process of repairing DNA damage using a homologous nucleic acid (e.g., an endogenous homologous sequence, e.g., a sister chromatid, or an exogenous nucleic acid, e.g., a template nucleic acid). Alt-HDR is distinct from canonical HDR in that the process utilizes different pathways from canonical HDR, and can be inhibited by the canonical HDR mediators, RAD51 and BRCA2. Alt-HDR is also distinguished by the involvement of a single-stranded or nicked homologous nucleic acid template, whereas canonical HDR generally involves a double-stranded homologous template.

"Canonical HDR," "canonical homology-directed repair" or "cHDR" refer to the process of repairing DNA damage using a homologous nucleic acid (e.g., an endogenous homologous sequence, e.g., a sister chromatid, or an exogenous nucleic acid, e.g., a template nucleic acid). Canonical HDR typically acts when there has been significant resection at the double strand break, forming at least one single-stranded portion of DNA. In a normal cell, cHDR typically involves a series of steps such as recognition of the break, stabilization of the break, resection, stabilization of single-stranded DNA, formation of a DNA crossover intermediate, resolution of the crossover intermediate, and ligation. The process requires RAD51 and BRCA2, and the homologous nucleic acid is typically double-stranded.

Unless indicated otherwise, the term "HDR" as used herein encompasses both canonical HDR and alt-HDR.

"Non-homologous end joining" or "NHEJ" refers to ligation mediated repair and/or non-template mediated repair including canonical NHEJ (cNHEJ) and alternative NHEJ (altNHEJ), which in turn includes microhomology-mediated end joining (MMEJ), single-strand annealing (SSA), and synthesis-dependent microhomology-mediated end joining (SD-MMEJ).

"Replacement" or "replaced," when used with reference to a modification of a molecule (e.g. a nucleic acid or protein), does not require a process limitation but merely indicates that the replacement entity is present.

"Subject" means a human or non-human animal. A human subject can be any age (e.g., an infant, child, young adult, or adult), and may suffer from a disease, or may be in need of alteration of a gene. Alternatively, the subject may be an animal, which term includes, but is not limited to, mammals, birds, fish, reptiles, amphibians, and more particularly non-human primates, rodents (such as mice, rats, hamsters, etc.), rabbits, guinea pigs, dogs, cats, and so on. In certain embodiments of this disclosure, the subject is livestock, e.g., a cow, a horse, a sheep, or a goat. In certain embodiments, the subject is poultry.

"Treat," "treating," and "treatment" mean the treatment of a disease in a subject (e.g., a human subject), including one or more of inhibiting the disease, i.e., arresting or preventing its development or progression; relieving the disease, i.e., causing regression of the disease state; relieving one or more symptoms of the disease; and curing the disease.

"Prevent," "preventing," and "prevention" refer to the prevention of a disease in a mammal, e.g., in a human, including (a) avoiding or precluding the disease; (b) affecting the predisposition toward the disease; or (c) preventing or delaying the onset of at least one symptom of the disease.

A "Kit" refers to any collection of two or more components that together constitute a functional unit that can be employed for a specific purpose. By way of illustration (and not limitation), one kit according to this disclosure can include a guide RNA complexed or able to complex with an RNA-guided nuclease, and accompanied by (e.g. suspended in, or suspendable in) a pharmaceutically acceptable carrier. The kit can be used to introduce the complex into, for example, a cell or a subject, for the purpose of causing a desired genomic alteration in such cell or subject. The components of a kit can be packaged together, or they may be separately packaged. Kits according to this disclosure also optionally include directions for use (DFU) that describe the use of the kit e.g., according to a method of this disclosure. The DFU can be physically packaged with the kit, or it can be made available to a user of the kit, for instance by electronic means.

The terms "polynucleotide", "nucleotide sequence", "nucleic acid", "nucleic acid molecule", "nucleic acid sequence", and "oligonucleotide" refer to a series of nucleotide bases (also called "nucleotides") in DNA and RNA, and mean any chain of two or more nucleotides. These terms refer to compositions that can be chimeric mixtures or derivatives or modified versions thereof, single-stranded or double-stranded. These terms also refer to compositions that can be modified at the base moiety, sugar moiety, or phosphate backbone, for example, to improve stability of the molecule, its hybridization parameters, etc. A nucleotide sequence typically carries genetic information, including, but not limited to, the information used by cellular machinery to make proteins and enzymes. These terms include double- or single-stranded genomic DNA, RNA, any synthetic and genetically manipulated polynucleotide, and both sense and antisense polynucleotides. These terms also include nucleic acids containing modified bases.

Conventional IUPAC notation is used in nucleotide sequences presented herein, as shown in Table 1, below (see also Cornish-Bowden A, Nucleic Acids Res. 1985 May 10;

13(9):3021-30, incorporated by reference herein). It should be noted, however, that "T" denotes "Thymine or Uracil" in those instances where a sequence may be encoded by either DNA or RNA, for example in gRNA targeting domains.

TABLE 1

| IUPAC nucleic acid notation | |
|---|---|
| Character | Base |
| A | Adenine |
| T | Thymine or Uracil |
| G | Guanine |
| C | Cytosine |
| U | Uracil |
| K | G or T/U |
| M | A or C |
| R | A or G |
| Y | C or T/U |
| S | C or G |
| W | A or T/U |
| B | C, G or T/U |
| V | A, C or G |
| H | A, C or T/U |
| D | A, G or T/U |
| N | A, C, G or T/U |

The terms "protein," "peptide" and "polypeptide" are used interchangeably to refer to a sequential chain of amino acids linked together via peptide bonds. The terms include individual proteins, groups or complexes of proteins that associate together, as well as fragments or portions, variants, derivatives and analogs of such proteins. Peptide sequences are presented herein using conventional notation, beginning with the amino or N-terminus on the left, and proceeding to the carboxyl or C-terminus on the right. Standard one-letter or three-letter abbreviations can be used.

Overview

In general terms, this disclosure concerns genome editing systems, including, but not limited to, transiently active genome editing systems, comprising RNA-guided nucleases and gRNAs that are targeted to specific, usually cellular, DNA sequences. The gRNAs used in these genome editing systems are referred to throughout this disclosure as "one-shot guide RNAs" or ogRNAs, to distinguish them from governing guide RNAs that are specifically targeted to nucleic acid sequences encoding RNA-guided nucleases such as Cas9. In the various embodiments of this disclosure, the nucleic acids encoding genome editing systems are modified to introduce sites recognized by ogRNAs, allowing them to function as ggRNAs without altering their ability to recognize the specific cellular sequences they have been designed to target. As such, in certain embodiments, the genome editing system can edit the endogenous target locus as well as the nucleic acid encoding the RNA-guided nuclease. FIG. 1A is a diagram illustrating a SaCas9-gRNA complex targeting the endogenous cellular locus as well as an engineered Cas9 sequence comprising an ogRNA target sequence in a viral vector.

Figure 1B:
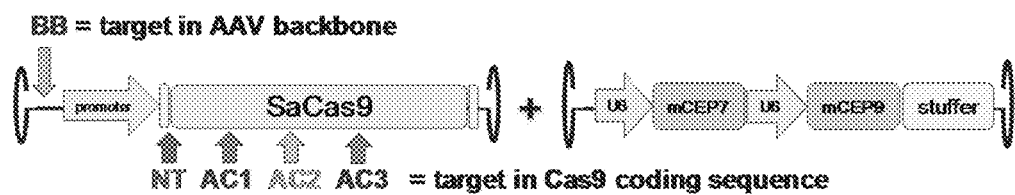
FIG. 1B is a cartoon diagram depicting a 2-vector system in which engineered SaCas9 and gRNAs are encoded on separate viral genomes. Two types of exemplary sites in a recombinant adeno-associated virus (AAV) genome into which heterologous cellular sequences can be engineered are marked by arrows.

For economy of presentation, and as illustrated in FIG. 1B, the sites that are introduced into nucleic acids encoding genome editing systems are grouped into (a) sites introduced into nucleic acid vector backbones, e.g. viral genome backbones, and/or (b) sites introduced into RNA-guided nuclease encoding sequences, for example, sequences encoding a Cas9 nuclease. This grouping is not intended to be limiting or binding to any particular theory or model, and (a) and (b) are not mutually exclusive. The introduction of ogRNA target sites into sequences encoding genome editing systems or vectors containing such sequences has several advantages over other self-inactivation strategies. For one thing, the introduction of an ogRNA target site into such nucleic acids allows self-inactivating genome editing systems to be designed and implemented without the need for a separate ggRNA. This in turn permits self-inactivating genome editing systems to be packaged in comparatively less space to facilitate, for example, a self-inactivating system comprising multiple gRNAs to be packaged in a single vector (a "one-shot" configuration) such as an AAV vector with a packaging limit of about 4.7 kb. Another advantage is a potential improvement in the predictability of the behavior of the ogRNA relative to ggRNA systems due to, for example, the elimination of variation due to differences in expression or cutting efficiency between a genomically-targeted gRNA and a ggRNA. Further advantages of the embodiments of this disclosure will be evident to those of skill in the art. In certain embodiments, sites introduced into the RNA-guided nuclease do not alter the nuclease activity of the RNA-guided nuclease as compared to the wild-type protein. In certain embodiments, the engineered RNA guided-nuclease has at least about 80%, about 85%, about 90%, about 95%, or about 99% nuclease activity of the wild-type protein.

Turning first to the introduction of engineered sequences into vector backbones, it will be understood by those of skill in the art that many vector nucleic acids, such as plasmids, artificial chromosomes, and/or recombinant viral vector genomes, comprise "backbone" sequences that do not encode RNA-guided nucleases. By engineering one or more ogRNA target sites into these backbone sequences, the genome editing system incorporating the ogRNA can recognize and alter the vector, for example by forming single- or double-strand breaks, point mutations, or other modifications as described in greater detail below. This alteration, in turn, can reduce or eliminate transcription of one or more components of the genome editing system and thereby limit the activity of the genome editing system.

An ogRNA target site, whether it is incorporated into a vector backbone or an RNA-guided nuclease coding sequence, will generally comprise a 16-24 nucleotide sequence (a "protospacer" sequence) that is complementary to a targeting domain sequence (or "spacer", 16-24 nucleotide in length) of the ogRNA; the protospacer is adjacent to a Protospacer Adjacent Motif (or "PAM") that is, generally, between 3 and 6 nucleotides in length depending on the species of RNA-guided nuclease used. Certain examples in this disclosure focus on target sites for use with *S. aureus* Cas9, which recognizes an NNGRRT or NNGRRV PAM that is immediately 3' of the protospacer sequence as visualized on the "top" or "complementary" strand. Without limiting the foregoing, an exemplary *S. aureus* ogRNA target site can be 22-30 nucleotides in length, comprising a 16-24 nucleic acid sequence in the eukaryotic gene and a 6 nucleotide PAM that is recognized by the *S. aureus* Cas9.

One-shot guide RNA target sites can be engineered into vector backbones in any suitable position, though it may be advantageous in certain cases to position ogRNA target sites in proximity to sites or elements that (a) are required for the stability of the vector in vivo, (b) that will lose function, rather than gain function, when disrupted by, e.g. an indel; and/or (c) that are required for the expression of functional RNA-guided nuclease. These sites or elements may include, without limitation, promoter sequences for gRNAs and/or RNA-guided nucleases; inverted terminal repeats, gRNA coding sequences, etc.

In certain embodiments where the ogRNA target site is introduced into a nucleic acid vector backbone, the target site is located within or adjacent to the promoter sequence of a gRNA and/or a RNA-guided nuclease. In certain embodiments, the target site is located upstream of a transcription start site of the promoter sequence, e.g., 0 bp, about 1 bp, about 10 bp, about 50 bp, about 100 bp, about 200 bp, about 500 bp, about 1000 bp, or any intermediate distance or ranges thereof upstream of the transcription start site. In certain embodiments, the target site is located downstream of a transcription start site of the promoter sequence, e.g., 0 bp, about 1 bp, about 10 bp, about 50 bp, about 100 bp, about 200 bp, about 500 bp, about 1000 bp, or any intermediate distance or ranges thereof downstream of the transcription start site. In certain embodiments, the target site comprises a transcription start site.

In certain embodiments where the ogRNA target site is introduced into a nucleic acid vector backbone, the target site is located within or adjacent to a 5' untranslated region (5' UTR) of a RNA-guided nuclease. In certain embodiments, the target site is located upstream of a translation start site of the promoter sequence, e.g., 0 bp, about 1 bp, about 10 bp, about 50 bp, about 100 bp, about 200 bp, about 500 bp, about 1000 bp, or any intermediate distance or ranges thereof upstream of the translation start site. In certain embodiments, the target site is located within or adjacent to a 3' untranslated region (3' UTR) of a RNA-guided nuclease. In certain embodiments, the target site is located downstream of a translation stop codon (e.g., TGA, TAA and TAG), e.g., 0 bp, about 1 bp, about 10 bp, about 50 bp, about 100 bp, about 200 bp, about 500 bp, about 1000 bp, or any intermediate distance or ranges thereof downstream of the translation stop site.

Table 2, below, includes one exemplary AAV backbone into which a target site (denoted by N's) is engineered near the 5' end (c.157insN$_{19-30}$)

TABLE 2

Exemplary in-backbone target sequence

[SEQ ID NO: 1]
TTGGCCACTCCCTCTCTGCGCGCTCGCTCGCTCACTGAGGCCGGGCGACCAAAGGTCGCCCGACGCCCGG

GCTTTGCCCGGGCGGCCTCAGTGAGCGAGCGAGCGCGCAGAGAGGGAGTGGCCAACTCCATCACTAGGGG

TTCCTCAGATCTGAATTNNNNNNNNNNNNNNNNNNNNNNNNNNNNNNCTAGCGCTTAAGTCGCGCATTGATTAT

TGACTAGTTATTAATAGTAATCAATTACGGGGTCATTAGTTCATAGCCCATATATGGAGTTCCGCGTTAC

ATAACTTACGGTAAATGGCCCGCCTGGCTGACCGCCCAACGACCCCCGCCCATTGACGTCAATAATGACG

TATGTTCCCATAGTAACGCCAATAGGGACTTTCCATTGACGTCAATGGGTGGACTATTTACGGTAAACTG

TABLE 2-continued

Exemplary in-backbone target sequence

CCCACTTGGCAGTACATCAAGTGTATCATATGCCAAGTACGCCCCCTATTGACGTCAATGACGGTAAATG

GCCCGCCTGGCATTATGCCCAGTACATGACCTTATGGGACTTTCCTACTTGGCAGTACATCTACGTATTA

GTCATCGCTATTACCATGGTGATGCGGTTTTGGCAGTACATCAATGGGCGTGGATAGCGGTTTGACTCAC

GGGGATTTCCAAGTCTCCACCCCATTGACGTCAATGGGAGTTTGTTTTGGCACCAAAATCAACGGGACTT

TCCAAAATGTCGTAACAACTCCGCCCCATTGACGCAAATGGGCGGTAGGCGTGTACGGTGGGAGGTCTAT

ATAAGCAGAGCTGGTTTAGTGAACCGTCAGATCCGCTAGAGATCCGCTCTAGAGGATCCGGTACTCGAGG

AACTGAAAAACCAGAAAGTTAACTGGTAAGTTTAGTCTTTTTGTCTTTTATTTCAGGTCCCGGATCCGGT

GGTGGTGCAAATCAAAGAACTGCTCCTCAGTGGATGTTGCCTTTACTTCTAGGCCTGTACGGAAGTGTTA

CGCGGCCGCCACCATGGGACCGAAGAAAAAGCGCAAGGTCGAAGCGTCCATGAAAAGGAACTACATTCTG

GGGCTGGACATCGGGATTACAAGCGTGGGGTATGGGATTATTGACTATGAAACAAGGGACGTGATCGACG

CAGGCGTCAGACTGTTCAAGGAGGCCAACGTGGAAAACAATGAGGGACGGAGAAGCAAGAGGGGAGCCAG

GCGCCTGAAACGACGGAGAAGGCACAGAATCCAGAGGGTGAAGAAACTGCTGTTCGATTACAACCTGCTG

ACCGACCATTCTGAGCTGAGTGGAATTAATCCTTATGAAGCCAGGGTGAAAGGCCTGAGTCAGAAGCTGT

CAGAGGAAGAGTTTTCCGCAGCTCTGCTGCACCTGGCTAAGCGCCGAGGAGTGCATAACGTCAATGAGGT

GGAAGAGGACACCGGCAACGAGCTGTCTACAAAGGAACAGATCTCACGCAATAGCAAAGCTCTGGAAGAG

AAGTATGTCGCAGAGCTGCAGCTGGAACGGCTGAAGAAAGATGGCGAGGTGAGAGGGTCAATTAATAGGT

TCAAGACAAGCGACTACGTCAAAGAAGCCAAGCAGCTGCTGAAAGTGCAGAAGGCTTACCACCAGCTGGA

TCAGAGCTTCATCGATACTTATATCGACCTGCTGGAGACTCGGAGAACCTACTATGAGGGACCAGGAGAA

GGGAGCCCCTTCGGATGGAAAGACATCAAGGAATGGTACGAGATGCTGATGGGACATTGCACCTATTTTC

CAGAAGAGCTGAGAAGCGTCAAGTACGCTTATAACGCAGATCTGTACAACGCCCTGAATGACCTGAACAA

CCTGGTCATCACCAGGGATGAAAACGAGAAACTGGAATACTATGAGAAGTTCCAGATCATCGAAAACGTG

TTTAAGCAGAAGAAAAAGCCTACACTGAAACAGATTGCTAAGGAGATCCTGGTCAACGAAGAGGACATCA

AGGGCTACCGGGTGACAAGCACTGGAAAACCAGAGTTCACCAATCTGAAAGTGTATCACGATATTAAGGA

CATCACAGCACGGAAAGAAATCATTGAGAACGCCGAACTGCTGGATCAGATTGCTAAGATCCTGACTATC

TACCAGAGCTCCGAGGACATCCAGGAAGAGCTGACTAACCTGAACAGCGAGCTGACCCAGGAAGAGATCG

AACAGATTAGTAATCTGAAGGGGTACACCGGAACACACAACCTGTCCCTGAAAGCTATCAATCTGATTCT

GGATGAGCTGTGGCATACAAACGACAATCAGATTGCAATCTTTAACCGGCTGAAGCTGGTCCCAAAAAAG

GTGGACCTGAGTCAGCAGAAAGAGATCCCAACCACACTGGTGGACGATTTCATTCTGTCACCCGTGGTCA

AGCGGAGCTTCATCCAGAGCATCAAAGTGATCAACGCCATCATCAAGAAGTACGGCCTGCCCAATGATAT

CATTATCGAGCTGGCTAGGGAGAAGAACAGCAAGGACGCACAGAAGATGATCAATGAGATGCAGAAACGA

AACCGGCAGACCAATGAACGCATTGAAGAGATTATCCGAACTACCGGGAAAGAGAACGCAAAGTACCTGA

TTGAAAAAATCAAGCTGCACGATATGCAGGAGGGAAAGTGTCTGTATTCTCTGGAGGCCATCCCCCTGGA

GGACCTGCTGAACAATCCATTCAACTACGAGGTCGATCATATTATCCCCAGAAGCGTGTCCTTCGACAAT

TCCTTTAACAACAAGGTGCTGGTCAAGCAGGAAGAGAACTCTAAAAAGGGCAATAGGACTCCTTTCCAGT

ACCTGTCTAGTTCAGATTCCAAGATCTCTTACGAAACCTTTAAAAAGCACATTCTGAATCTGGCCAAAGG

AAAGGGCCGCATCAGCAAGACCAAAAAGGAGTACCTGCTGGAAGAGCGGGACATCAACAGATTCTCCGTC

CAGAAGGATTTTATTAACCGGAATCTGGTGGACACAAGATACGCTACTCGCGGCCTGATGAATCTGCTGC

GATCCTATTTCCGGGTGAACAATCTGGATGTGAAAGTCAAGTCCATCAACGGCGGGTTCACATCTTTTCT

GAGGCGCAAATGGAAGTTTAAAAAGGAGCGCAACAAAGGGTACAAGCACCATGCCGAAGATGCTCTGATT

TABLE 2-continued

Exemplary in-backbone target sequence

ATCGCAAATGCCGACTTCATCTTTAAGGAGTGGAAAAAGCTGGACAAAGCCAAGAAAGTGATGGAGAACC

AGATGTTCGAAGAGAAGCAGGCCGAATCTATGCCCGAAATCGAGACAGAACAGGAGTACAAGGAGATTTT

CATCACTCCTCACCAGATCAAGCATATCAAGGATTTCAAGGACTACAAGTACTCTCACCGGGTGGATAAA

AAGCCCAACAGAGAGCTGATCAATGACACCCTGTATAGTACAAGAAAAGACGATAAGGGGAATACCCTGA

TTGTGAACAATCTGAACGGACTGTACGACAAAGATAATGACAAGCTGAAAAAGCTGATCAACAAAAGTCC

CGAGAAGCTGCTGATGTACCACCATGATCCTCAGACATATCAGAAACTGAAGCTGATTATGGAGCAGTAC

GGCGACGAGAAGAACCCACTGTATAAGTACTATGAAGAGACTGGGAACTACCTGACCAAGTATAGCAAAA

AGGATAATGGCCCCGTGATCAAGAAGATCAAGTACTATGGGAACAAGCTGAATGCCCATCTGGACATCAC

AGACGATTACCCTAACAGTCGCAACAAGGTGGTCAAGCTGTCACTGAAGCCATACAGATTCGATGTCTAT

CTGGACAACGGCGTGTATAAATTTGTGACTGTCAAGAATCTGGATGTCATCAAAAAGGAGAACTACTATG

AAGTGAATAGCAAGTGCTACGAAGAGGCTAAAAAGCTGAAAAAGATTAGCAACCAGGCAGAGTTCATCGC

CTCCTTTTACAACAACGACCTGATTAAGATCAATGGCGAACTGTATAGGGTCATCGGGGTGAACAATGAT

CTGCTGAACCGCATTGAAGTGAATATGATTGACATCACTTACCGAGAGTATCTGGAAAACATGAATGATA

AGCGCCCCCCTCGAATTATCAAAACAATTGCCTCTAAGACTCAGAGTATCAAAAAGTACTCAACCGACAT

TCTGGGAAACCTGTATGAGGTGAAGAGCAAAAAGCACCCTCAGATTATCAAAAAGGGCGGATCCCCCAAG

AAGAAGAGGAAAGTCTCGAGCGACTACAAAGACCATGACGGTGATTATAAAGATCATGACATCGATTACA

AGGATGACGATGACAAGTAGCAATAAAGGATCGTTTATTTTCATTGGAAGCGTGTGTTGGTTTTTGATC

AGGCGCGTCCAAGCTTGCATGCTGGGGAGAGATCTAGGAACCCCTAGTGATGGAGTTGGCCACTCCCTCT

CTGCGCGCTCGCTCGCTCACTGAGGCCGCCCGGGCAAAGCCCGGGCGTCGGGCGACCTTTGGTCGCCCGG

CCTCAGTGAGCGAGCGAGCGCGCAGAGAGGGAGTGGCCAA

While the exemplary backbone sequence of Table 2 includes a single target site, this disclosure also encompasses backbones into which 2, 3, 4, 5 or more identical or non-identical target sequences are engineered into the vector. Additionally, it will be appreciated by those of skill in the art that certain sequences within the vector backbone may be similar to portions of the target site, and that these sites may be easily modified to create target sites. For example, there can be multiple PAMs within the vector backbone, and the sequence immediately 5' (as visualized on the complementary or top strand) can be modified to differ by 0, 1, 2, 3 or more nucleotides from the protospacer sequence recognized by the ogRNA. Alternatively, a PAM sequence may be introduced into a sequence encoding a gRNA targeting domain for example by modifying the residues of the gRNA immediately 3' of the targeting domain. In certain embodiments, an isolated nucleic acid encoding a Cas9 protein having a eukaryotic sequence can share at least 80% (e.g. 80%, 85%, 90%, 95%, 96%, 97%, 98%, 99% or greater identity) sequence identity with SEQ ID NO: 1. In certain embodiments, an isolated nucleic acid encoding a Cpf1 protein having a eukaryotic sequence can share at least 80% (e.g. 80%, 85%, 90%, 95%, 96%, 97%, 98%, 99% or greater identity) sequence identity with SEQ ID NO: 14.

Figure 3A:
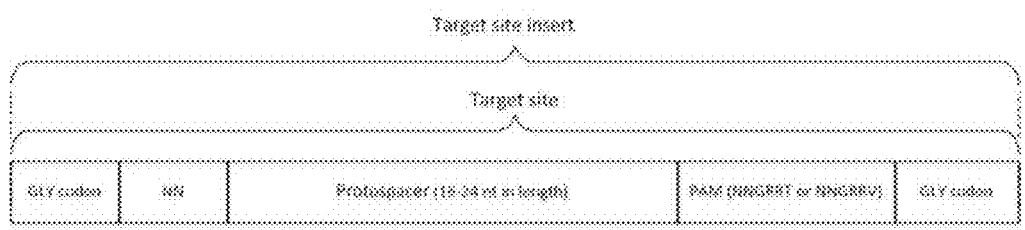
FIGS. 3A-3C are schematic graphs showing exemplary peptide-encoding inserts incorporating heterologous cellular sequences.
Figure 3B:
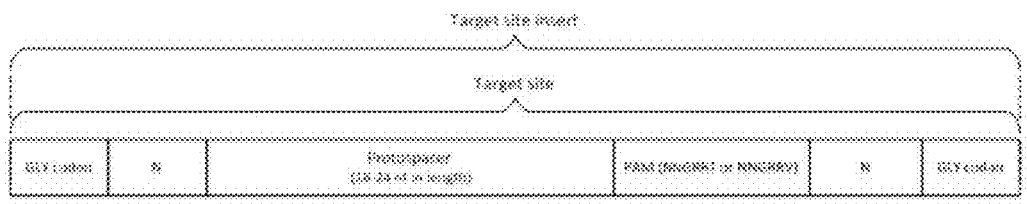
Figure 3C:
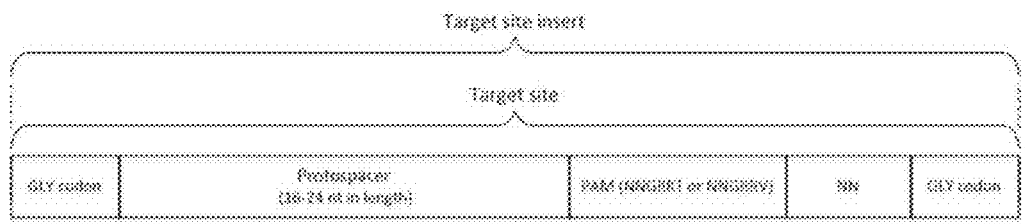

Turning next to systems in which a target site is introduced into a sequence encoding an RNA-guided nuclease, this disclosure provides certain engineered S. aureus Cas9 proteins that are encoded by DNA sequences comprising target sites as described above. Short (e.g. 24-42 base pair, or 8-13 amino-acid) sequences comprising such target sites are referred to as "inserts" when they are implemented in Cas9-coding sequences and/or engineered Cas9 proteins, whether they are inserted into the sequence, or replace a portion of the sequence. FIGS. 3A-3C are schematic graphs showing exemplary peptide-encoding inserts incorporating heterologous cellular sequences.

Skilled artisans will appreciate that the design criteria for inserts include certain conditions that are not necessarily applicable to target sites in the "backbone" sequence of a DNA vector. For one thing, the length of the insert in certain embodiments is divisible by three to avoid the introduction of a frameshift mutation that may affect the function of the engineered RNA-guided nuclease. In instances where genomic target sites have a length that is not divisible by three, one or two additional nucleotides are added to the insert as necessary to preserve the reading frame of the coding sequence comprising the insert.

Figure 2:
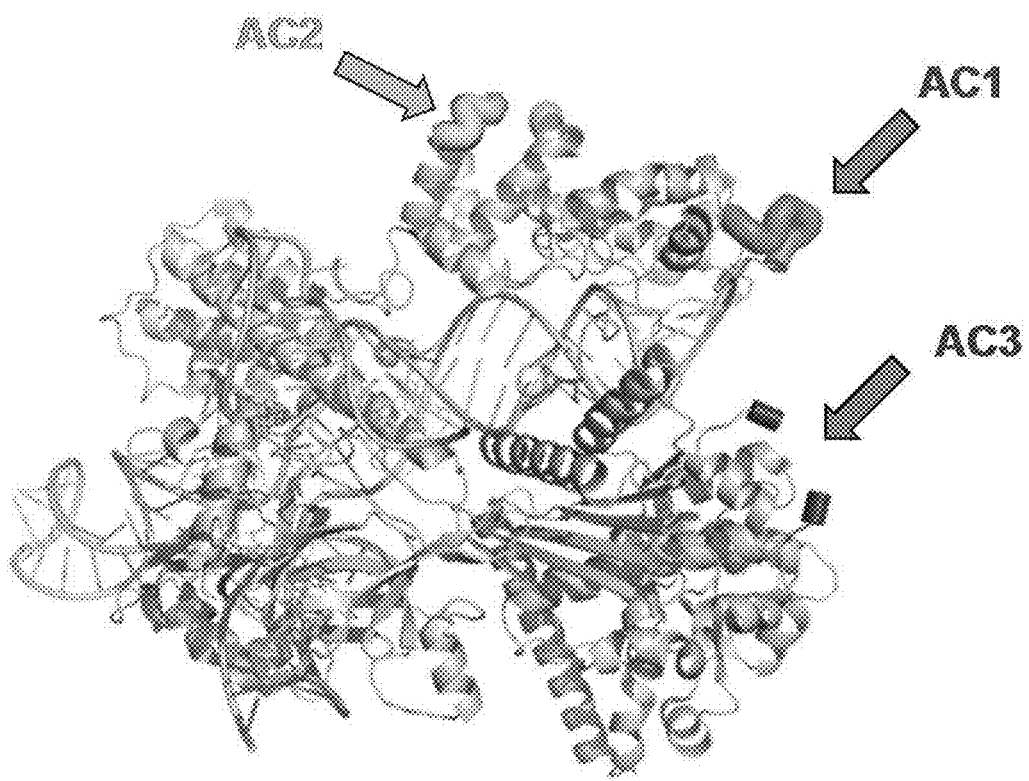
FIG. 2 is a ribbon diagram depicting an S. aureus Cas9 protein. Exemplary regions which can be encoded by engineered heterologous sequences are identified by arrows.

Another design criterion that is met by certain embodiments of this disclosure is minimal disruption of the structure of the engineered protein comprising the insert. This requirement is met in some instances by (a) locating the insert in a region of the nuclease protein where the addition of amino acids is well tolerated, and/or (b) selecting inserts that will tend not to disrupt the structure of the surrounding protein. These two design elements are dealt with in turn:

With respect to the location of the insert, FIGS. 1B and 2 depict four exemplary sites (AC1, AC2, AC3, NT) in the S. aureus Cas9 protein into which an insert is added in various embodiments of this disclosure, e.g. E271_N272insGX$_6$_

10G, L371_N372insGX6-10G, Q737_A738insGX6-10G, and/or at or near the N-terminus (NT). The peptide sequences corresponding to each of these positions are presented in Table 3 below. In the table, residues within the insert are denoted by X. The sequences presented include 10-12-amino acid inserts for clarity, however, the insert can have any suitable length.

In certain embodiments, an insert "at or near the N-terminus" is positioned within about 20 amino acid residues from the first amino acid residue of an RNA-guided nuclease (e.g., Cas9 or Cpf1) peptide. In certain embodiments, an insert at or near the N-terminus is positioned at about 0, about 1, about 2, about 3, about 4, about 5, about 6, about 7, about 8, about 9, about 10, about 11, about 12, about 13, about 14, about 15, about 16, about 17, about 18, about 19, or about 20 amino acid residues from the first amino acid residue of an RNA-guided nuclease (e.g., Cas9 or Cpf1) peptide. In certain embodiments, an insert at or near the N-terminus is positioned upstream of the first amino acid residue of an RNA-guided nuclease (e.g., Cas9 or Cpf1) peptide. In certain embodiments, an insert at or near the N-terminus is positioned downstream of the first amino acid residue of an RNA-guided nuclease (e.g., Cas9 or Cpf1) peptide. In certain embodiments, an insert at or near the N-terminus is positioned between a nuclear localization sequence (NLS) and the coding sequence for the RNA-guided nuclease peptide. In certain embodiments, the NLS comprises a peptide sequence set forth in SEQ ID NO: 12 GPKKKRKVEAS [SEQ ID NO: 12].

In certain embodiments, an insert at or near the N-terminus is positioned within about 9 amino acid residues from the first amino acid residue of a Cas9 peptide. In certain embodiments, an insert at or near the N-terminus is positioned at about 0, about 1, about 2, about 3, about 4, about 5, about 6, about 7, about 8, about 9 amino acid residues from the first amino acid residue of a Cas9 peptide. In certain embodiments, an insert at or near the N-terminus is positioned within about 20 amino acid residues from the first amino acid residue of a Cpf1 peptide. In certain embodiments, an insert at or near the N-terminus is positioned at about 0, about 1, about 2, about 3, about 4, about 5, about 6, about 7, about 8, about 9, about 10, about 11, about 12, about 13, about 14, about 15, about 16, about 17, about 18, about 19, or about 20 amino acid residues from the first amino acid residue of a Cpf1 peptide.

In certain embodiments, the insert can comprise a translational start codon (i.e., ATG). In certain embodiments, the translational start codon (i.e., ATG) is in-frame with the RNA-guided nuclease coding sequence. In certain embodiments, an insert at or near the N-terminus of the RNA-guided nuclease coding sequence is positioned between a translational start codon (i.e., ATG) and the RNA-guided nuclease coding sequence.

Additionally, skilled artisans will appreciate that RNA-guided nuclease sequences (e.g., Cas9 or Cpf1 protein sequences) may be modified in ways that do not disrupt the operation of the ogRNA, and that these sequences may be modified to have 1, 2, 3, 4, 5, 6, 7, 8, 9, 10 or more amino acid changes. Said another way, in certain embodiments, sequences will have more than 95% sequence identity to the corresponding naturally occurring RNA-guided nuclease. In certain embodiments, inserts added in these three exemplary sites do not alter the nuclease activity of the RNA-guided nuclease protein as compared to the wild-type RNA-guided nuclease. In certain embodiments, the RNA-guided nuclease with inserts added in the exemplary sites will have at least about 40%, about 50%, about 60%, about 70%, about 80%, about 85%, about 90%, about 95%, or about 99% nuclease activity of the wild-type RNA-guided nuclease.

TABLE 3

Exemplary engineered Cas9 proteins

| | |
|---|---|
| Sample *S. aureus* Cas9 peptide sequence | MKRNYILGLDIGITSVGYGIIDYETRDVIDAGVRLFKEANVENNEGRRSKRGARRLKRRRRHRIQRVK KLLFDYNLLTDHSELSGINPYEARVKGLSQKLSEEEFSAALLHLAKRRGVHNVNEVEEDTGNELSTKE QISRNSKALEEKYVAELQLERLKKDGEVRGSINRFKTSDYVKEAKQLLKVQKAYHQLDQSFIDTYIDL LETRRTYYEGPGEGSPFGWKDIKEWYEMLMGHCTYFPEELRSVKYAYNADLYNALNDLNNLVITRDEN EKLEYYEKFQIIENVFKQKKKPTLKQIAKEILVNEEDIKGYRVISIGKPEFTNLKVYHDIKDITARKE IIENAELLDQIAKILTIYQSSEDIQEELTNLNSELTQEEIEQISNLKGYTGTHNLSLKAINLILDELW HTNDNQIAIFNRLKLVPKKVDLSQQKEIPTTLVDDFILSPVVKRSFIQSIKVINAIIKKYGLPNDIII ELAREKNSKDAQKMINEMQKRNRQTNERIEEIIRTTGKENAKYLIEKIKLHDMQEGKCLYSLEAIPLE DLLNNPFNYEVDHIIPRSVSFDNSFNNKVLVKQEENSKKGNRTPFQYLSSSDSKISYETFKKHILNLA KGKGRISKTKKEYLLEERDINRFSVQKDFINRNLVDTRYATRGLMNLLRSYFRVNNLDVKVKSINGGF TSFLRRKWKFKKERNKGYKHHAEDALIIANADFIFKEWKKLDKAKKVMENQMFEEKQAESMPEIETEQ EYKEIFITPHQIKHIKDFKDYKYSHRVDKKPNRELINDTLYSTRKDDKGNTLIVNNLNGLYDKDNDKL KKLINKSPEKLLMYHHDPQTYQKLKLIMEQYGDEKNPLYKYYEETGNYLIKYSKKDNGPVIKKIKYYG NKLNAHLDITDDYPNSRNKVVKLSLKPYRFDVYLDNGVYKFVTVKNLDVIKKENYYEVNSKCYEEAKK LKKISNQAEFIASFYNNDLIKINGELYRVIGVNNDLLNRIEVNMIDITYREYLENMNDKRPPRIIKTI ASKTQSIKKYSTDILGNLYEVKSKKHPQIIKKG [SEQ ID NO: 2] |
| Position 1 E271_N272insGX6-10G | MKRNYILGLDIGITSVGYGIIDYETRDVIDAGVRLFKEANVENNEGRRSKRGARRLKRRRRHRIQRVK KLLFDYNLLTDHSELSGINPYEARVKGLSQKLSEEEFSAALLHLAKRRGVHNVNEVEEDTGNELSTKE QISRNSKALEEKYVAELQLERLKKDGEVRGSINRFKTSDYVKEAKQLLKVQKAYHQLDQSFIDTYIDL LETRRTYYEGPGEGSPFGWKDIKEWYEMLMGHCTYFPEELRSVKYAYNADLYNALNDLNNLVITRDEX XXXXXXXXXXXNEKLEYYEKFQIIENVFKQKKKPTLKQIAKEILVNEEDIKGYRVTSTGKPEFTNLKV YHDIKDITARKEIIENAELLDQIAKILTIYQSSEDIQEELTNLNSELTQEEIEQISNLKGYTGTHNLS LKAINLILDELWHTNDNQIAIFNRLKLVPKKVDLSQQKEIPTTLVDDFILSPVVKRSFIQSIKVINAI IKKYGLPNDIIIELAREKNSKDAQKMINEMQKRNRQTNERIEEIIRTTGKENAKYLIEKIKLHDMQEG KCLYSLEAIPLEDLLNNPFNYEVDHIIPRSVSFDNSFNNKVLVKQEENSKKGNRTPFQYLSSSDSKIS YETFKKHILNLAKGKGRISKIKKEYLLEERDINRFSVQKDFINRNLVDTRYATRGLMNLLRSYFRVNN LDVKVKSINGGFTSFLRRKWKFKKERNKGYKHHAEDALIIANADFIFKEWKKLDKAKKVMENQMFEEK QAESMPEIETEQEYKEIFITPHQIKHIKDFKDYKYSHRVDKKPNRELINDTLYSTRKDDKGNTLIVNN LNGLYDKDNDKLKKLINKSPEKLLMYHHDPQTYQKLKLIMEQYGDEKNPLYKYYEEIGNYLIKYSKKD NGPVIKKIKYYGNKLNAHLDITDDYPNSRNKVVKLSLKPYRFDVYLDNGVYKFVTVKNLDVIKKENYY EVNSKCYEEAKKLKKISNQAEFIASFYNNDLIKINGELYRVIGVNNDLLNRIEVNMIDITYREYLENM NDKRPPRIIKTIASKTQSIKKYSTDILGNLYEVKSKKHPQIIKKG [SEQ ID NO: 3] |

TABLE 3-continued

Exemplary engineered Cas9 proteins

| | |
|---|---|
| Position 2<br>L371_N372insGX$_{6-10}$G | MKRNYILGLDIGITSVGYGIIDYETRDVIDAGVRLFKEANVENNEGRRSKRGARRLKRRRRHRIQRVK<br>KLLFDYNLLTDHSELSGINPYEARVKGLSQKLSEEEFSAALLHLAKRRGVHNVEVEEDTGNELSTKE<br>QISRNSKALEEKYVAELQLERLKKDGEVRGSINREKTSDYVKEAKQLLKVQKAYHQLDQSFIDTYIDL<br>LETRRTYYEGPGEGSPFGWKDIKEWYEMLMGHCTYFPEELRSVKYAYNADLYNALNDLNNLVITRDEN<br>EKLEYYEKFQIIENVFKQKKKPILKQIAKEILVNEEDIKGYRVISIGKPEFTNLKVYHDIKDITARKE<br>IIENAELLDQIAKILTIYQSSEDIQEELTNLXXXXXXXXXXXXNSELTQEEIEQISNLKGYTGTHNLS<br>LKAINLILDELWHTNDNQIAIENRLKLVPKKVDLSQQKEIPTTLVDDFILSPVVKRSFIQSIKVINAI<br>IKKYGLPNDIIIELAREKNSKDAQKMINEMQKRNRQTNERIEEIIRTTGKENAKYLIEKIKLHDMQEG<br>KCLYSLEAIPLEDLLNNPFNYEVDHIIPRSVSFDNSFNNKVLVKQEENSKKGNRTPFQYLSSSDSKIS<br>YETFKKHILNLAKGKGRISKTKKEYLLEERDINRFSVQKDFINRNLVDTRYATRGLMNLLRSYFRVNN<br>LDVKVKSINGGFTSFLRRKWKFKKERNKGYKHHAEDALIIANADFIFKEWKKLDKAKKVMENQMFEEK<br>QAESMPEIETEQEYKEIFITPHQIKHIKDFKDYKYSHRVDKKPNRELINDTLYSTRKDDKGNTLIVNN<br>LNGLYDKDNDKLKKLINKSPEKLLMYHHDPQTYQKLKLIMEQYGDEKNPLYKYYEETGNYLTKYSKKD<br>NGPVIKKIKYYGNKLNAHLDITDDYPNSRNKVVKLSLKPYRFDVYLDNGVYKFVTVKNLDVIKKENYY<br>EVNSKCYEEAKKLKKISNQAEFIASFYNNDLIKINGELYRVIGVNNDLLNRIEVNMIDITYREYLENM<br>NDKRPPRIIKTIASKTQSIKKYSTDILGNLYEVKSKKHPQIIKKG [SEQ ID NO: 4] |
| Position 3<br>Q737_A738insGX$_{6-10}$G | MKRNYILGLDIGITSVGYGIIDYETRDVIDAGVRLFKEANVENNEGRRSKRGARRLKRRRRHRIQRVK<br>KLLFDYNLLTDHSELSGINPYEARVKGLSQKLSEEEFSAALLHLAKRRGVHNVEVEEDTGNELSTKE<br>QISRNSKALEEKYVAELQLERLKKDGEVRGSINRFKTSDYVKEAKQLLKVQKAYHQLDQSFIDTYIDL<br>LETRRTYYEGPGEGSPFGWKDIKEWYEMLMGHCTYFPEELRSVKYAYNADLYNALNDLNNLVITRDEN<br>EKLEYYEKFQIIENVFKQKKKPTLKQIAKEILVNEEDIKGYRVTSTGKPEFTNLKVYHDIKDITARKE<br>IIENAELLDQIAKILTIYQSSEDIQEELTNLNSELTQEEIEQISNLKGYTGTHNLSLKAINLILDELW<br>HTNDNQIAIFNRLKLVPKKVDLSQQKEIPTTLVDDFILSPVVKRSFIQSIKVINAIIKKYGLPNDIII<br>ELAREKNSKDAQKMINEMQKRNRQTNERIEEIIRTTGKENAKYLIEKIKLHDMQEGKCLYSLEAIPLE<br>DLLNNPFNYEVDHIIPRSVSFDNSFNNKVLVKQEENSKKGNRTPFQYLSSSDSKISYETFKKHILNLA<br>KGKGRISKTKKEYLLEERDINRFSVQKDFINRNLVDTRYATRGLMNLLRSYFRVNNLDVKVKSINGGF<br>TSFLRRKWKFKKERNKGYKHHAEDALIIANADFIFKEWKKLDKAKKVMENQMFEEKQXXXXXXXXXXXX<br>XAESMPEIETEQEYKEIFITPHQIKHIKDFKDYKYSHRVDKKPNRELINDTLYSTRKDDKGNTLIVNN<br>LNGLYDKDNDKLKKLINKSPEKLLMYHHDPQTYQKLKLIMEQYGDEKNPLYKYYEETGNYLTKYSKKD<br>NGPVIKKIKYYGNKLNAHLDITDDYPNSRNKVVKLSLKPYRFDVYLDNGVYKFVTVKNLDVIKKENYY<br>EVNSKCYEEAKKLKKISNQAEFIASFYNNDLIKINGELYRVIGVNNDLLNRIEVNMIDITYREYLENM<br>NDKRPPRIIKTIASKTQSIKKYSTDILGNLYEVKSKKHPQIIKKG [SEQ ID NO: 5] |
| Position NT | MGPKKKRKVEASXXXXXXXXXXXX<u>MKRNYILGLDIGITSVGYGIIDYETRDVIDAGVRLFKEANVENNEG<br>RRSKRGARRLKRRRRHRIQRVKKLLFDYNLLTDHSELSGINPYEARVKGLSQKLSEEEFSAALLHLAK<br>RRGVHNVEVEEDTGNELSTKEQISRNSKALEEKYVAELQLERLKKDGEVRGSINREKTSDYVKEAKQ<br>LLKVQKAYHQLDQSFIDTYIDLLETRRTYYEGPGEGSPFGWKDIKEWYEMLMGHCTYFPEELRSVKYA<br>YNADLYNALNDLNNLVITRDENEKLEYYEKFQIIENVFKQKKKPTLKQIAKEILVNEEDIKGYRVTST<br>GKPEFTNLKVYHDIKDITARKEIIENAELLDQIAKILTIYQSSEDIQEELTNLNSELTQEEIEQISNL<br>KGYTGTHNLSLKAINLILDELWHTNDNQIAIFNRLKLVPKKVDLSQQKEIPTTLVDDFILSPVVKRSF<br>IQSIKVINAIIKKYGLPNDIIIELAREKNSKDAQKMINEMQKRNRQTNERIEEIIRTTGKENAKYLIE<br>KIKLHDMQEGKCLYSLEAIPLEDLLNNPFNYEVDHIIPRSVSFDNSFNNKVLVKQEENSKKGNRTPFQ<br>YLSSSDSKISYETFKKHILNLAKGKGRISKTKKEYLLEERDINRFSVQKDFINRNLVDTRYATRGLMN<br>LLRSYFRVNNLDVKVKSINGGFTSFLRRKWKFKKERNKGYKHHAEDALIIANADFIFKEWKKLDKAKK<br>VMENQMFEEKQAESMPEIETEQEYKEIFITPHQIKHIKDFKDYKYSHRVDKKPNRELINDTLYSTRKD<br>DKGNTLIVNNLNGLYDKDNDKLKKLINKSPEKLLMYHHDPQTYQKLKLIMEQYGDEKNPLYKYYEETG<br>NYLTKYSKKDNGPVIKKIKYYGNKLNAHLDITDDYPNSRNKVVKLSLKPYRFDVYLDNGVYKFVTVKN<br>LDVIKKENYYEVNSKCYEEAKKLKKISNQAEFIASFYNNDLIKINGELYRVIGVNNDLLNRIEVNMID<br>ITYREYLENMNDKRPPRIIKTIASKTQSIKKYSTDILGNLYEVKSKKHPQIIKKG [SEQ ID<br>NO: 10]</u> |

The engineered Cas9 proteins presented in Table 3 are encoded by the exemplary nucleic acids sequences listed in Table 4. In the table, the nucleotides within the insert are denoted by N, and insert positions corresponding to amino acid positions 1-3 are c.813_814insN$_{27-36}$, c.1113_1114insN$_{27-36}$, and c.2211_2212insN$_{27-36}$, respectively.

TABLE 4

Exemplary nucleic acid sequences encoding engineered Cas9 proteins

| | |
|---|---|
| Sample codon-optimized<br>S. aureus Cas9 sequence | ATGAAAAGGAACTACATTCTGGGGCTGGACATCGGGATTACAAGCGTGGGGTATGGGATTATTGACTA<br>TGAAACAAGGGACGTGATCGACGCAGGCGTCAGACTGTTCAAGGAGGCCAACGTGGAAAACAATGAGG<br>GACGGAGAAGCAAGAGGGGAGCCAGGCGCCTGAAACGACGGAGAAGGCACAGAATCCAGAGGGTGAAG<br>AAACTGCTGTTCGATTACAACCTGCTGACCGACCATTCTGAGCTGAGTGGAATTAATCCTTATGAAGC<br>CAGGGTGAAAGGCCTGAGTCAGAAGCTGTCAGAGGAAGAGTTTTCCGCAGCTCTGCTGCACCTGGCTA<br>AGCGCCGAGGAGTGCATAACGTCAATGAGGTGGAAGAGGACACCGGCAACGAGCTGTCTACAAAGGAA<br>CAGATCTCACGCAATAGCAAAGCTCTGGAAGAGAAGTATGTCGCAGAGCTGCAGCTGGAACGGCTGAA<br>GAAAGATGGCGAGGTGAGAGGGTCAATTAATAGGTTCAAGACAAGCGACTACGTCAAAGAAGCCAAGC<br>AGCTGCTGAAAGTGCAGAAGGCTTACCACCAGCTGGATCAGAGCTTCATCGATACTTATATCGACCTG<br>CTGGAGACTCGGAGAACCTACTATGAGGGACCAGGAGAAGGGAGCCCCTTCGGATGGAAAGACATCAA |

TABLE 4-continued

Exemplary nucleic acid sequences encoding engineered Cas9 proteins

|  |  |
|---|---|
|  | GGAATGGTACGAGATGCTGATGGGACATTGCACCTATTTTCCAGAAGAGCTGAGAAGCGTCAAGTACG<br>CTTATAACGCAGATCTGTACAACGCCCTGAATGACCTGAACAACCTGGTCATCACCAGGGATGAAAAC<br>GAGAAACTGGAATACTATGAGAAGTTCCAGATCATCGAAAACGTGTTTAAGCAGAAGAAAAAGCCTAC<br>ACTGAAACAGATTGCTAAGGAGATCCTGGTCAACGAAGAGGACATCAAGGGCTACCGGGTGACAAGCA<br>CTGGAAAACCAGAGTTCACCAATCTGAAAGTGTATCACGATATTAAGGACATCACAGCACGGAAAGAA<br>ATCATTGAGAACGCCGAACTGCTGGATCAGATTGCTAAGATCCTGACTATCTACCAGAGCTCCGAGGA<br>CATCCAGGAAGAGCTGACTAACCTGAACAGCGAGCTGACCCAGGAAGAGATCGAACAGATTAGTAATC<br>TGAAGGGGTACACCGGAACACACAACCTGTCCCTGAAAGCTATCAATCTGATTCTGGATGAGCTGTGG<br>CATACAAACGACAATCAGATTGCAATCTTTAACCGGCTGAAGCTGGTCCCAAAAAAGGTGGACCTGAG<br>TCAGCAGAAAGAGATCCCAACCACACTGGTGGACGATTTCATTCTGTCACCCGTGGTCAAGCGGAGCT<br>TCATCCAGAGCATCAAAGTGATCAACGCCATCATCAAGAAGTACGGCCTGCCCAATGATATCATTATC<br>GAGCTGGCTAGGGAGAAGAACAGCAAGGACGCACAGAAGATGATCAATGAGATGCAGAAACGAAACCG<br>GCAGACCAATGAACGCATTGAAGAGATTATCCGAACTACCGGGAAAGAGAACGCAAAGTACCTGATTG<br>AAAAAATCAAGCTGCACGATATGCAGGAGGGAAAGTGTCTGTATTCTCTGGAGGCCATCCCCCTGGAG<br>GACCTGCTGAACAATCCATTCAACTACGAGGTCGATCATATTATCCCCAGAAGCGTGTCCTTCGACAA<br>TTCCTTTAACAACAAGGTGCTGGTCAAGCAGGAAGAGAACTCTAAAAAGGGCAATAGGACTCCTTTCC<br>AGTACCTGTCTAGTTCAGATTCCAAGATCTCTTACGAAACCTTTAAAAAGCACATTCTGAATCTGGCC<br>AAAGGAAAGGGCCGCATCAGCAAGACCAAAAAGGAGTACCTGCTGGAAGAGCGGGACATCAACGATT<br>CTCCGTCCAGAAGGATTTTATTAACCGGAATCTGGTGGACACAAGATACGCTACTCGCGGCCTGATGA<br>ATCTGCTGCGATCCCTATTTCCGGGTGAACAATCTGGATGTGAAAGTCAAGTCCATCAACGGCGGGTTC<br>ACATCTTTTCTGAGGCGCAAATGGAAGTTTAAAAAGGAGCGCAACAAAGGGTACAAGCACCATGCCGA<br>AGATGCTCTGATTATCGCAAATGCCGACTTCATCTTTAAGGAGTGGAAAAAGCTGGACAAAGCCAAGA<br>AAGTGATGGAGAACCAGATGTTCGAAGAGAAGCAGGCCGAATCTATGCCCGAAATCGAGACAGAACAG<br>GAGTACAAGGAGATTTTCATCACTCCTCACCAGATCAAGCATATCAAGGATTTCAAGGACTACAAGTA<br>CTCTCACCGGGTGGATAAAAGCCCAACAGAGAGCTGATCAATGACACCCTGTATAGTACAAGAAAAG<br>ACGATAAGGGGAATACCCTGATTGTGAACAATCTGAACGGACTGTACGACAAAGATAATGACAAGCTG<br>AAAAAGCTGATCAACAAAAGTCCCGAGAAGCTGCTGATGTACCACCATGATCCTCAGACATATCAGAA<br>ACTGAAGCTGATTATGGAGCAGTACGGCGACGAGAAGAACCCACTGTATAAGTACTATGAAGAGACTG<br>GGAACTACCTGACCAAGTATAGCAAAAAGGATAATGGCCCCGTGATCAAGAAGATCAAGTACTATGGG<br>AACAAGCTGAATGCCCATCTGGACATCACAGACGATTACCCTAACAGTCGCAACAAGGTGGTCAAGCT<br>GTCACTGAAGCCATACAGATTCGATGTCTATCTGGACAACGGCGTGTATAAATTTGTGACTGTCAAGA<br>ATCTGGATGTCATCAAAAAGGAGAACTACTATGAAGTGAATAGCAAGTGCTACGAAGAGGCTAAAAAG<br>CTGAAAAAGATTAGCAACCAGGCAGAGTTCATCGCCTCCTTTTACAACAACGACCTGATTAAGATCAA<br>TGGCGAACTGTATAGGGTCATCGGGGTGAACAATGATCTGCTGAACCGCATTGAAGTGAATATGATTG<br>ACATCACTTACCGAGAGTATCTGGAAAACATGAATGATAAGCGCCCCCCTCGAATTATCAAAACAATT<br>GCCTCTAAGACTCAGAGTATCAAAAAGTACTCAACCGACATTCTGGGAAACCTGTATGAGGTGAAGAG<br>CAAAAAGCACCCTCAGATTATCAAAAAGGGC [SEQ ID NO: 6] |
| Position 1<br>c.813_814insN$_{27-36}$ | ATGAAAAGGAACTACATTCTGGGGCTGGACATCGGGATTACAAGCGTGGGGTATGGGATTATTGACTA<br>TGAAACAAGGGACGTGATCGACGCAGGCGTCAGACTGTTCAAGGAGGCCAACGTGGAAAACAATGAGG<br>GACGGAGAAGCAAGAGGGGAGCCAGGCGCCTGAAACGACGGAGAAGGCACAGAATCCAGAGGGTGAAG<br>AAACTGCTGTTCGATTACAACCTGCTGACCGACCATTCTGAGCTGAGTGGAATTAATCCTTATGAAGC<br>CAGGGTGAAAGGCCTGAGTCAGAAGCTGTCAGAGGAAGAGTTTTCCGCAGCTCTGCTGCACCTGGCTA<br>AGCGCCGAGGAGTGCATAACGTCAATGAGGTGGAAGAGGACACCGGCAACGAGCTGTCTACAAAGGAA<br>CAGATCTCACGCAATAGCAAAGCTCTGGAAGAGAAGTATGTCGCAGAGCTGCAGCTGGAACGGCTGAA<br>GAAAGATGGCGAGGTGAGAGGGTCAATTAATAGGTTCAAGACAAGCGACTACGTCAAAGAAGCCAAGC<br>AGCTGCTGAAAGTGCAGAAGGCTTACCACCAGCTGGATCAGAGCTTCATCGATACTTATATCGACCTG<br>CTGGAGACTCGGAGAAACCTACTATGAGGGACCAGGAGAAGGGACCCCCTTTGGATGGAAAGACATCAA<br>GGAATGGTACGAGATGCTGATGGGACATTGCACCTATTTTCCAGAAGAGCTGAGAAGCGTCAAGTACG<br>CTTATAACGCAGATCTGTACAACGCCCTGAATGACCTGAACAACCTGGTCATCACCAGGGATGAANNN<br>NNNNNNNNNNNNNNNNNNNNNNNNNNNNNNNNNAACGAGAAACTGGAATACTATGAGAAGTTCCAGAT<br>CATCGAAAACGTGTTTAAGCAGAAGAAAAAGCCTACACTGAAACAGATTGCTAAGGAGATCCTGGTCA<br>ACGAAGAGGACATCAAGGGCTACCGGGTGACAAGCACTGGAAAACCAGAGTTCACCAATCTGAAAGTG<br>TATCACGATATTAAGGACATCACAGCACGGAAAGAAATCATTGAGAACGCCGAACTGCTGGATCAGAT<br>TGCTAAGATCCTGACTATCTACCAGAGCTCCGAGGACATCCAGGAAGAGCTGACTAACCTGAACAGCG<br>AGCTGACCCAGGAAGAGATCGAACAGATTAGTAATCTGAAGGGGTACACCGGAACACACAACCTGTCC<br>CTGAAAGCTATCAATCTGATTCTGGATGAGCTGTGGCATACAAACGACAATCAGATTGCAATCTTTAA<br>CCGGCTGAAGCTGGTCCCAAAAAAGGTGGACCTGAGTCAGCAGAAAGAGATCCCAACCACACTGGTGG<br>ACGATTTCATTCTGTCACCCGTGGTCAAGCGGAGCTTCATCCAGAGCATCAAAGTGATCAACGCCATC<br>ATCAAGAAGTACGGCCTGCCCAATGATATCATTATCGAGCTGGCTAGGGAGAAGAACAGCAAGGACGC<br>ACAGAAGATGATCAATGAGATGCAGAAACGAAACCGGCAGACCAATGAACGCATTGAAGAGATTATCC<br>GAACTACCGGGAAAGAGAACGCAAAGTACCTGATTGAAAAAATCAAGCTGCACGATATGCAGGAGGGA<br>AAGTGTCTGTATTCTCTGGAGGCCATCCCCCTGGAGGACCTGCTGAACAATCCATTCAACTACGAGGT<br>CGATCATATTATCCCCAGAAGCGTGTCCTTCGACAATTCCTTTAACAACAAGGTGCTGGTCAAGCAGG<br>AAGAGAACTCTAAAAAGGGCAATAGGACTCCTTTCCAGTACCTGTCTAGTTCAGATTCCAAGATCTCT<br>TACGAAACCTTTAAAAAGCACATTCTGAATCTGGCCAAAGGAAAGGGCCGCATCAGCAAGACCAAAAA<br>GGAGTACCTGCTGGAAGAGCGGGACATCAACAGATTCTCCGTCCAGAAGGATTTTATTAACCGGAATC<br>TGGTGGACACAAGATACGCTACTCGCGGCCTGATGAATCTGCTGCGATCCTATTTCCGGGTGAACAAT<br>CTGGATGTGAAAGTCAAGTCCATCAACGGCGGGTTCACATCTTTTCTGAGGCGCAAATGGAAGTTTAA<br>AAAGGAGCGCAACAAAGGGTACAAGCACCATGCCGAAGATGCTCTGATTATCGCAAATGCCGACTTCA<br>TCTTTAAGGAGTGGAAAAAGCTGGACAAAGCCAAGAAAGTGATGGAGAACCAGATGTTCGAAGAGAAG<br>CAGGCCGAATCTATGCCCGAAATCGAGACAGAACAGGAGTACAAGGAGATTTTCATCACTCCTCACCA<br>GATCAAGCATATCAAGGATTTCAAGGACTACAAGTACTCTCACCGGGTGGATAAAAGCCCAACAGAGA<br>GCTGATCAATGACACCCTGTATAGTACAAGAAAAGACGATAAGGGGAATACCCTGATTGTGAACAAT<br>CTGAACGGACTGTACGACAAAGATAATGACAAGCTGAAAAAGCTGATCAACAAAAGTCCCGAGAAGCT<br>GCTGATGTACCACCATGATCCTCAGACATATCAGAAACTGAAGCTGATTATGGAGCAGTACGGCGACG<br>AGAAGAACCCACTGTATAAGTACTATGAAGAGACTGGGAACTACCTGACCAAGTATAGCAAAAAGGAT<br>AATGGCCCCGTGATCAAGAAGATCAAGTACTATGGGAACAAGCTGAATGCCCATCTGGACATCACAGA |

TABLE 4-continued

Exemplary nucleic acid sequences encoding engineered Cas9 proteins

| | |
|---|---|
| | CGATTACCCTAACAGTCGCAACAAGGTGGTCAAGCTGTCACTGAAGCCATACAGATTCGATGTCTATC<br>TGGACAACGGCGTGTATAAATTTGTGACTGTCAAGAATCTGGATGTCATCAAAAAGGAGAACTACTAT<br>GAAGTGAATAGCAAGTGCTACGAAGAGGCTAAAAAGCTGAAAAAGATTAGCAACCAGGCAGAGTTCAT<br>CGCCTCCTTTTACAACAACGACCTGATTAAGATCAATGGCGAACTGTATAGGGTCATCGGGGTGAACA<br>ATGATCTGCTGAACCGCATTGAAGTGAATATGATTGACATCACTTACCGAGAGTATCTGGAAAACATG<br>AATGATAAGCGCCCCCCTCGAATTATCAAAACAATTGCCTCTAAGACTCAGAGTATCAAAAAGTACTC<br>AACCGACATTCTGGGAAACCTGTATGAGGTGAAGAGCAAAAAGCACCCTCAGATTATCAAAAAGGGC<br>[SEQ ID NO: 7] |
| Position 2<br>c.1113_1114insN$_{27-36}$ | ATGAAAAGGAACTACATTCTGGGGCTGGACATCGGGATTACAAGCGTGGGGTATGGGATTATTGACTA<br>TGAAACAAGGGACGTGATCGACGCAGGCGTCAGACTGTTCAAGGAGGCCAACGTGGAAAACAATGAGG<br>GACGGAGAAGCAAGAGGGGAGCCAGGCGCCTGAAACGACGGAGAAGGCACAGAATCCAGAGGGTGAAG<br>AAACTGCTGTTCGATTACAACCTGCTGACCGACCATTCTGAGCTGAGTGGAATTAATCCTTATGAAGC<br>CAGGGTGAAAGGCCTGAGTCAGAAGCTGTCAGAGGAAGAGTTTTCCGCAGCTCTGCTGCACCTGGCTA<br>AGCGCCGAGGAGTGCATAACGTCAATGAGGTGGAAGAGGACACCGGCAACGAGCTGTCTACAAAGGAA<br>CAGATCTCACGCAATAGCAAAGCTCTGGAAGAGAAGTATGTCGCAGAGCTGCAGCTGGAACGGCTGAA<br>GAAAGATGGCGAGGTGAGAGGGTCAATTAATAGGTTCAAGACAAGCGACTACGTCAAAGAAGCCAAGC<br>AGCTGCTGAAAGTGCAGAAGGCTTACCACCAGCTGGATCAGAGCTTCATCGATACTTATATCGACCTG<br>CTGGAGACTCGGAGAACCTACTATGAGGGACCAGGAGAAGGGAGCCCCTTCGGATGGAAAGACATCAA<br>GGAATGGTACGAGATGCTGATGGGACATTGCACCTATTTTCCAGAAGAGCTGAGAAGCGTCAAGTACG<br>CTTATAACGCAGATCTGTACAACGCCCTGAATGACCTGAACAACCTGGTCATCACCAGGGATGAAAAC<br>GAGAAACTGGAATACTATGAGAAGTTCCAGATCATCGAAAACGTGTTTAAGCAGAAGAAAAAGCCTAC<br>ACTGAAACAGATTGCTAAGGAGATCCTGGTCAACGAAGAGGACATCAAGGGCTACCGGGTGACAAGCA<br>CTGGAAAACCAGAGTTCACCAATCTGAAAGTGTATCACGATATTAAGGACATCACAGCACGGAAAGAA<br>ATCATTGAGAACGCCGAACTGCTGGATCAGATTGCTAAGATCCTGACTATCTACCAGAGCTCCGAGGA<br>CATCCAGGAAGAGCTGACTAACCTGNNNNNNNNNNNNNNNNNNNNNNNNNNNNNNNNNNNAACAGCG<br>AGCTGACCCAGGAAGAGATCGAACAGATTAGTAATCTGAAGGGGTACACCGGAACACACAACCTGTCC<br>CTGAAAGCTATCAATCTGATTCTGGATGAGCTGTGGCATACAAACGACAATCAGATTGCAATCTTTAA<br>CCGGCTGAAGCTGGTCCCAAAAAAGGTGGACCTGAGTCAGCAGAAAGAGATCCCAACCACACTGGTGG<br>ACGATTTCATTCTGTCACCCGTGGTCAAGCGGAGCTTCATCCAGAGCATCAAAGTGATCAACGCCATC<br>ATCAAGAAGTACGGCCTGCCCAATGATATCATTATCGAGCTGGCTAGGGAGAAGAACAGCAAGGACGC<br>ACAGAAGATGATCAATGAGATGCAGAAACGAAACCGGCAGAACAATGAACGCATTGAAGAGATTATCC<br>GAACTACCGGGAAAGAGAACGCAAAGTACCTGATTGAAAAAATCAAGCTGCACGATATGCAGGAGGGA<br>AAGTGTCTGTATTCTCTGGAGGCCATCCCCCTGGAGGACCTGCTGAACAATCCATTCAACTACGAGGT<br>CGATCATATTATCCCCAGAAGCGTGTCCTTCGACAATTCCTTTAACAACAAGGTGCTGGTCAAGCAGG<br>AAGAGAACTCTAAAAAGGGCAATAGGACTCCTTTCCAGTACCTGTCTAGTTCAGATTCCAAGATCTCT<br>TACGAAACCTTTAAAAAGCACATTCTGAATCTGGCCAAAGGAAAGGGCCGCATCAGCAAGACCAAAAA<br>GGAGTACCTGCTGGAAGAGCGGGACATCAACAGATTCTCCGTCCAGAAGGATTTTATTAACCGGAATC<br>TGGTGGACACAAGATACGCTACTCGCGGCCTGATGAATCTGCTGCGATCCTATTTCCGGGTGAACAAT<br>CTGGATGTGAAAGTCAAGTCCATCAACGGCGGGTTCACATCTTTTCTGAGGCGCAAATGGAAGTTTAA<br>AAAGGAGCGCAACAAAGGGTACAAGCACCATGCCGAAGATGCTCTGATTATCGCAAATGCCGACTTCA<br>TCTTTAAGGAGTGGAAAAAGCTGGACAAAGCCAAGAAAGTGATGGAGAACCAGATGTTCGAAGAGAAG<br>CAGGCCGAATCTATGCCCGAAATCGAGACAGAACAGGAGTACAAGGAGATTTTCATCACTCCTCACCA<br>GATCAAGCATATCAAGGATTTCAAGGACTACAAGTACTCTCACCGGGTGGATAAAAAGCCCAACAGAG<br>AGCTGATCAATGACACCCTGTATAGTACAAGAAAAGACGATAAGGGGAATACCCTGATTGTGAACAAT<br>CTGAACGGACTGTACGACAAAGATAATGACAAGCTGAAAAAGCTGATCAACAAAAGTCCCGAGAAGCT<br>GCTGATGTACCACCATGATCCTCAGACATATCAGAAACTGAAGCTGATTATGGAGCAGTACGGCGACG<br>AGAAGAACCCACTGTATAAGTACTATGAAGAGACTGGGAACTACCTGACCAAGTATAGCAAAAAGGAT<br>AATGGCCCCGTGATCAAGAAGATCAAGTACTATGGGAACAAGCTGAATGCCCATCTGGACATCACAGA<br>CGATTACCCTAACAGTCGCAACAAGGTGGTCAAGCTGTCACTGAAGCCATACAGATTCGATGTCTATC<br>TGGACAACGGCGTGTATAAATTTGTGACTGTCAAGAATCTGGATGTCATCAAAAAGGAGAACTACTAT<br>GAAGTGAATAGCAAGTGCTACGAAGAGGCTAAAAAGCTGAAAAAGATTAGCAACCAGGCAGAGTTCAT<br>CGCCTCCTTTTACAACAACGACCTGATTAAGATCAATGGCGAACTGTATAGGGTCATCGGGGTGAACA<br>ATGATCTGCTGAACCGCATTGAAGTGAATATGATTGACATCACTTACCGAGAGTATCTGGAAAACATG<br>AATGATAAGCGCCCCCCTCGAATTATCAAAACAATTGCCTCTAAGACTCAGAGTATCAAAAAGTACTC<br>AACCGACATTCTGGGAAACCTGTATGAGGTGAAGAGCAAAAAGCACCCTCAGATTATCAAAAAGGGC<br>[SEQ ID NO: 8] |
| Position 3<br>c.2211_2212insN$_{27-36}$ | ATGAAAAGGAACTACATTCTGGGGCTGGACATCGGGATTACAAGCGTGGGGTATGGGATTATTGACTA<br>TGAAACAAGGGACGTGATCGACGCAGGCGTCAGACTGTTCAAGGAGGCCAACGTGGAAAACAATGAGG<br>GACGGAGAAGCAAGAGGGGAGCCAGGCGCCTGAAACGACGGAGAAGGCACAGAATCCAGAGGGTGAAG<br>AAACTGCTGTTCGATTACAACCTGCTGACCGACCATTCTGAGCTGAGTGGAATTAATCCTTATGAAGC<br>CAGGGTGAAAGGCCTGAGTCAGAAGCTGTCAGAGGAAGAGTTTTCCGCAGCTCTGCTGCACCTGGCTA<br>AGCGCCGAGGAGTGCATAACGTCAATGAGGTGGAAGAGGACACCGGCAACGAGCTGTCTACAAAGGAA<br>CAGATCTCACGCAATAGCAAAGCTCTGGAAGAGAAGTATGTCGCAGAGCTGCAGCTGGAACGGCTGAA<br>GAAAGATGGCGAGGTGAGAGGGTCAATTAATAGGTTCAAGACAAGCGACTACGTCAAAGAAGCCAAGC<br>AGCTGCTGAAAGTGCAGAAGGCTTACCACCAGCTGGATCAGAGCTTCATCGATACTTATATCGACCTG<br>CTGGAGACTCGGAGAACCTACTATGAGGGACCAGGAGAAGGGAGCCCCTTCGGATGAAAGACATCAA<br>GGAATGGTACGAGATGCTGATGGGACATTGCACCTATTTTCCAGAAGAGCTGAGAAGCGTCAAGTACG<br>CTTATAACGCAGATCTGTACAACGCCCTGAATGACCTGAACAACCTGGTCATCACCAGGGATGAAAAC<br>GAGAAACTGGAATACTATGAGAAGTTCCAGATCATCGAAAACGTGTTTAAGCAGAAGAAAAAGCCTAC<br>ACTGAAACAGATTGCTAAGGAGATCCTGGTCAACGAAGAGGACATCAAGGGCTACCGGGTGACAAGCA<br>CTGGAAAACCAGAGTTCACCAATCTGAAAGTGTATCACGATATTAAGGACATCACAGCACGGAAAGAA<br>ATCATTGAGAACGCCGAACTGCTGGATCAGATTGCTAAGATCCTGACTATCTACCAGAGCTCCGAGGA<br>CATCCAGGAAGAGCTGACTAACCTGAACAGCGAGCTGACCCAGGAAGAGATCGAACAGATTAGTAATC<br>TGAAGGGGTACACCGGAACACACAACCTGTCCCTGAAAGCTATCAATCTGATTCTGGATGAGCTGTGG<br>CATACAAACGACAATCAGATTGCAATCTTTAACCGGCTGAAGCTGGTCCCAAAAAAGGTGGACCTGAG<br>TCAGCAGAAAGAGATCCCAACCACACTGGTGGACGATTTCATTCTGTCACCCGTGGTCAAGCGGAGCT |

TABLE 4-continued

Exemplary nucleic acid sequences encoding engineered Cas9 proteins

TCATCCAGAGCATCAAAGTGATCAACGCCATCATCAAGAAGTACGGCCTGCCCAATGATATCATTATC
GAGCTGGCTAGGGAGAAGAACAGCAAGGACGCACAGAAGATGATCAATGAGATGCAGAAACGAAACCG
GCAGACCAATGAACGCATTGAAGAGATTATCCGAACTACCGGGAAAGAGAACGCAAAGTACCTGATTG
AAAAAATCAAGCTGCACGATATGCAGGAGGGAAAGTGTCTGTATTCTCTGGAGGCCATCCCCCTGGAG
GACCTGCTGAACAATCCATTCAACTACGAGGTCGATCATATTATCCCCAGAAGCGTGTCCTTCGACAA
TTCCTTTAACAACAAGGTGCTGGTCAAGCAGGAAGAGAACTCTAAAAAGGGCAATAGGACTCCTTTCC
AGTACCTGTCTAGTTCAGATTCCAAGATCTCTTACGAAACCTTTAAAAAGCACATTCTGAATCTGGCC
AAAGGAAAGGGCCGCATCAGCAAGACCAAAAAGGAGTACCTGCTGGAAGAGCGGGACATCAACAGATT
CTCCGTCCAGAAGGATTTTATTAACCGGAATCTGGTGGACACAAGATACGCTACTCGCGGCCTGATGA
ATCTGCTGCGATCCTATTTCCGGGTGAACAATCTGGATGTGAAAGTCAAGTCCATCAACGGCGGGTTC
ACATCTTTTCTGAGGCGCAAATGGAAGTTTAAAAAGGAGCGCAACAAAAGGGTACAAGCACCATGCCGA
AGATGCTCTGATTATCGCAAATGCCGACTTCATCTTTAAGGAGTGGAAAAAGCTGGACAAAGCCAAGA
AAGTGATGGAGAACCAGATGTTCGAAGAGAAGCAG**NNNNNNNNNNNNNNNNNNNNNNNNNNNNNNN
NNN**GCCGAATCTATGCCCGAAATCGAGACAGAACAGGAGTACAAGGAGATTTTCATCACTCCTCACCA
GATCAAGCATATCAAGGATTTCAAGGACTACAAGTACTCTCACCGGGTGGATAAAAAGCCCAACAGAG
AGCTGATCAATGACACCCTGTATAGTACAAGAAAAGACGATAAGGGGAATACCCTGATTGTGAACAAT
CTGAACGGACTGTACGACAAAGATAATGACAAGCTGAAAAAGCTGATCAACAAAAGTCCCGAGAAGCT
GCTGATGTACCACCATGATCCTCAGACATATCAGAAACTGAAGCTGATTATGGAGCAGTACGGCGACG
AGAAGAACCCACTGTATAAGTACTATGAAGAGACTGGGAACTACCTGACCAAGTATAGCAAAAAGGAT
AATGGCCCCGTGATCAAGAAGATCAAGTACTATGGGAACAAGCTGAATGCCCATCTGGACATCACAGA
CGATTACCCTAACAGTCGCAACAAGGTGGTCAAGCTGTCACTGAAGCCATACAGATTCGATGTCTATC
TGGACAACGGCGTGTATAAATTTGTGACTGTCAAGAATCTGGATGTCATCAAAAAGGAGAACTACTAT
GAAGTGAATAGCAAGTGCTACGAAGAGGCTAAAAAGCTGAAAAAGATTAGCAACCAGGCAGAGTTCAT
CGCCTCCTTTTACAACAACGACCTGATTAAGATCAATGGCGAACTGTATAGGGTCATCGGGGTGAACA
ATGATCTGCTGAACCGCATTGAAGTGAATATGATTGACATCACTTACCGAGAGTATCTGGAAAACATG
AATGATAAGCGCCCCCCTCGAATTATCAAAACAATTGCCTCTAAGACTCAGAGTATCAAAAAGTACTC
AACCGACATTCTGGGAAACCTGTATGAGGTGAAGAGCAAAAAGCACCCTCAGATTATCAAAAAGGGC
[SEQ ID NO: 9]

Position NT    ATGGGACCGAAGAAAAAGCGCAAGGTCGAAGCGTCCNNNNNNNNNNNNNNNNNNNNNNNNNNNNNNNAT
GAAAAGGAACTACATTCTGGGGCTGGACATCGGGATTACAAGCGTGGGGTATGGGATTATTGACTATG
AAACAAGGGACGTGATCGACGCAGGCGTCAGACTGTTCAAGGAGGCCAACGTGGAAAACAATGAGGGA
CGGAGAAGCAAGAGGGGAGCCAGGCGCCTGAAACGACGGAGAAGGCACAGAATCCAGAGGGTGAAGAA
ACTGCTGTTCGATTACAACCTGCTGACCGACCATTCTGAGCTGAGTGGAATTAATCCTTATGAAGCCA
GGGTGAAAGGCCTGAGTCAGAAGCTGTCAGAGGAAGAGTTTTCCGCAGCTCTGCTGCACCTGGCTAAG
CGCCGAGGAGTGCATAACGTCAATGAGGTGGAAGAGGACACCGGCAACGAGCTGTCTACAAAGGAACA
GATCTCACGCAATAGCAAAGCTCTGGAAGAGAAGTATGTCGCAGAGCTGCAGCTGGAACGGCTGAAGA
AGATGGCGAGGTGAGAGGGTCAATTAATAGGTTCAAGACAAGCGACTACGTCAAAGAAGCCAAGCAG
CTGCTGAAAGTGCAGAAGGCTTACCACCAGCTGGATCAGAGCTTCATCGATACTTATATCGACCTGCT
GGAGACTCGGAGAACCTACTATGAGGGACCAGGAGAAGGGAGCCCCTTCGGATGGAAAGACATCAAGG
AATGGTACGAGATGCTGATGGGACATTGCACCTATTTTCCAGAAGAGCTGAGAAGCGTCAAGTACGCT
TATAACGCAGATCTGTACAACGCCCTGAATGACCTGAACAACCTGGTCATCACCAGGGATGAAAACGA
GAAACTGGAATACTATGAGAAGTTCCAGATCATCGAAAACGTGTTTAAGCAGAAGAAAAAGCCTACAC
TGAAACAGATTGCTAAGGAGATCCTGGTCAACGAAGAGGACATCAAGGGCTACCGGGTGACAAGCACT
GGAAAACCAGAGTTCACCAATCTGAAAGTGTATCACGATATTAAGGACATCACAGCACGGAAAGAAAT
CATTGAGAACGCCGAACTGCTGGATCAGATTGCTAAGATCCTGACTATCTACCAGAGCTCCGAGGACA
TCCAGGAAGAGCTGACTAACCTGAACAGCGAGCTGACCCAGGAAGAGATCGAACAGATTAGTAATCTG
AAGGGGTACACCGGAACACACACAACCTGTCCCGAAAGCTATCAATCTGATTCTGGATGAGCTGTGGCA
TACAAACGACAATCAGATTGCAATCTTTAACCGGCTGAAGCTGGTCCCAAAAAAGGTGGACCTGAGTC
AGCAGAAAGAGATCCCAACCACACTGGTGGACGATTTCATTCTGTCACCCGTGGTCAAGCGGAGCTTC
ATCCAGAGCATCAAAGTGATCAACGCCATCATCAAGAAGTACGGCCTGCCCAATGATATCATTATCGA
GCTGGCTAGGGAGAAGAACAGCAAGGACGCACAGAAGATGATCAATGAGATGCAGAAACGAAACCGGC
AGACCAATGAACGCATTGAAGAGATTATCCGAACTACCGGGAAAGAGAACGCAAAGTACCTGATTGAA
AAAATCAAGCTGCACGATATGCAGGAGGGAAAGTGTCTGTATTCTCTGGAGGCCATCCCCCTGGAGGA
CCTGCTGAACAATCCATTCAACTACGAGGTCGATCATATTATCCCCAGAAGCGTGTCCTTCGACAATT
CCTTTAACAACAAGGTGCTGGTCAAGCAGGAAGAGAACTCTAAAAAGGGCAATAGGACTCCTTTCCAG
TACCTGTCTAGTTCAGATTCCAAGATCTCTTACGAAACCTTTAAAAAGCACATTCTGAATCTGGCCAA
AGGAAAGGGCCGCATCAGCAAGACCAAAAAGGAGTACCTGCTGGAAGAGCGGGACATCAACAGATTCT
CCGTCCAGAAGGATTTTATTAACCGGAATCTGGTGGACACAAGATACGCTACTCGCGGCCTGATGAAT
CTGCTGCGATCCTATTTCCGGGTGAACAATCTGGATGTGAAAGTCAAGTCCATCAACGGCGGGTTCAC
ATCTTTTCTGAGGCGCAAATGGAAGTTTAAAAAGGAGCGCAACAAAAGGGTACAAGCACCATGCCGAA
GATGCTCTGATTATCGCAAATGCCGACTTCATCTTTAAGGAGTGGAAAAAGCTGGACAAAGCCAAGAA
AGTGATGGAGAACCAGATGTTCGAAGAGAAGCAGGCCGAATCTATGCCCGAAATCGAGACAGAACAGGA
GTACAAGGAGATTTTCATCACTCCTCACCAGATCAAGCATATCAAGGATTTCAAGGACTACAAGTACT
CTCACCGGGTGGATAAAAAGCCCAACAGAGAGCTGATCAATGACACCCTGTATAGTACAAGAAAAGAC
GATAAGGGGAATACCCTGATTGTGAACAATCTGAACGGACTGTACGACAAAGATAATGACAAGCTGAA
AAAGCTGATCAACAAAAGTCCCGAGAAGCTGCTGATGTACCACCATGATCCTCAGACATATCAGAAAC
TGAAGCTGATTATGGAGCAGTACGGCGACGAGAAGAACCCACTGTATAAGTACTATGAAGAGACTGGG
AACTACCTGACCAAGTATAGCAAAAAGGATAATGGCCCCGTGATCAAGAAGATCAAGTACTATGGGAA
CAAGCTGAATGCCCATCTGGACATCACAGACGATTACCCTAACAGTCGCAACAAGGTGGTCAAGCTGT
CACTGAAGCCATACAGATTCGATGTCTATCTGGACAACGGCGTGTATAAATTTGTGACTGTCAAGAAT
CTGGATGTCATCAAAAAGGAGAACTACTATGAAGTGAATAGCAAGTGCTACGAAGAGGCTAAAAAGCT
GAAAAAGATTAGCAACCAGGCAGAGTTCATCGCCTCCTTTTACAACAACGACCTGATTAAGATCAATG
GCGAACTGTATAGGGTCATCGGGGTGAACAATGATCTGCTGAACCGCATTGAAGTGAATATGATTGAC
ATCACTTACCGAGAGTATCTGGAAAACATGAATGATAAGCGCCCCCCTCGAATTATCAAAACAATTGC
CTCTAAGACTCAGAGTATCAAAAAGTACTCAACCGACATTCTGGGAAACCTGTATGAGGTGAAGAGCA
AAAAGCACCCTCAGATTATCAAAAAGGGC [SEQ ID NO: 11]

In certain embodiments, the RNA-guided nuclease is Cpf1. In certain embodiments, the amino acid sequence of a Cpf1 protein is set forth in SEQ ID NO: 13. In certain embodiments, the Cpf1 protein can comprise an insertion such as a $GX_{6-10}G$ insertion. In certain embodiments, the insertion (relative to SEQ ID NO: 13) is positioned between amino acid positions 147 and 148, anywhere between amino acid positions 484 and 492, anywhere between amino acid positions 568 and 590, anywhere between amino acid positions 795 and 855, anywhere between amino acid positions 1131 and 1140, or anywhere between amino acid positions 1160 and 1173. In certain embodiments, the insertion is positioned at or near the N-terminus of a Cpf1 peptide. In certain embodiments, the amino acid sequence of the Cpf1 protein comprising the insertion has at least 95% sequence identity (e.g. 95%, 96%, 97%, 98%, 99% or greater identity) to SEQ ID NO: 13.

[SEQ ID NO: 13]
MTQFEGFTNLYQVSKTLRFELIPQGKTLKHIQEQGFIEEDKARNDHYKELK

PIIDRIYKTYADQCLQLVQLDWENLSAAIDSYRKEKTEETRNALIEEQATY

RNAIHDYFIGRTDNLTDAINKRHAEIYKGLFKAELFNGKVLKQLGTVTTTE

HENALLRSFDKFTTYFSGFYENRKNVFSAEDISTAIPHRIVQDNFPKFKEN

CHIFTRLITAVPSLREHFENVKKAIGIFVSTSIEEVFSFPFYNQLLTQTQI

DLYNQLLGGISREAGTEKIKGLNEVLNLAIQKNDETAHIIASLPHRFIPLF

KQILSDRNTLSFILEEFKSDEEVIQSFCKYKTLLRNENVLETAEALFNELN

SIDLTHIFISHKKLETISSALCDHWDTLRNALYERRISELTGKITKSAKEK

VQRSLKHEDINLQEIISAAGKELSEAFKQKTSEILSHAHAALDQPLPTTLK

KQEEKEILKSQLDSLLGLYHLLDWFAVDESNEVDPEFSARLTGIKLEMEPS

LSFYNKARNYATKKPYSVEKFKLNFQMPTLASGWDVNKEKNNGAILFVKNG

LYYLGIMPKQKGRYKALSFEPTEKTSEGFDKMYYDYFPDAAKMIPKCSTQL

KAVTAHFQTHTTPILLSNNFIEPLEITKEIYDLNNPEKEPKKFQTAYAKKT

GDQKGYREALCKWIDFTRDFLSKYTKTTSIDLSSLRPSSQYKDLGEYYAEL

NPLLYHISFQRIAEKEIMDAVETGKLYLFQIYNKDFAKGHHGKPNLHTLYW

TGLFSPENLAKTSIKLNGQAELFYRPKSRMKRMAHRLGEKMLNKKLKDQKT

PIPDTLYQELYDYVNHRLSHDLSDEARALLPNVITKEVSHEIIKDRRFTSD

KFFFHVPITLNYQAANSPSKFNQRVNAYLKEHPETPIIGIDRGERNLIYIT

VIDSTGKILEQRSLNTIQQFDYQKKLDNREKERVAARQAWSVVGTIKDLKQ

GYLSQVIHEIVDLMIHYQAVVVLANLNFGFKSKRTGIAEKAVYQQFEKMLI

DKLNCLVLKDYPAEKVGGVLNPYQLTDQFTSFAKMGTQSGFLFYVPAPYTS

KIDPLTGFVDPFVWKTIKNHESRKHFLEGFDFLHYDVKTGDFILHFKMNRN

LSFQRGLPGFMPAWDIVFEKNETQFDAKGTPFIAGKRIVPVIENHRFTGRY

RDLYPANELIALLEEKGIVFRDGSNILPKLLENDDSHAIDTMVALIRSVLQ

MRNSNAATGEDYINSPVRDLNGVCFDSRFQNPEWPMDADANGAYHIALKGQ

LLLNHLKESKDLKLQNGISNQDWLAYIQELRN

In certain embodiments, an isolated nucleic acid sequence encoding a Cpf1 protein is set forth in SEQ ID NO: 14. In certain embodiments, the isolated Cpf1 nucleic acid can comprise an insertion such as an N24-36 insertion. In certain embodiments, the insertion (relative to SEQ ID NO: 14) is positioned between nucleic acid positions 441 and 442, anywhere between nucleic acid positions 1452 and 1474, anywhere between nucleic acid positions 1704 and 1768, anywhere between nucleic acid positions 2385 and 2563, anywhere between nucleic acid positions 3393 and 3418, or anywhere between nucleic acid positions 3480 and 3517. In certain embodiments, the insertion does not alter the reading frame of the isolated Cpf1 nucleic acid. In certain embodiments, the insertion is positioned at or near the N-terminus of a Cpf1 peptide. In certain embodiments, the nucleic acid sequence of the Cpf1 protein comprising the insertion has at least 95% (e.g. 95%, 96%, 97%, 98%, 99% or greater identity) sequence identity to SEQ ID NO: 14. Isolated nucleic acids according to this aspect of this disclosure are optionally incorporated into vectors such as plasmids, viral vectors, naked DNA vectors, etc. In some instances, an adeno-associated virus (AAV) vector incorporates isolated nucleic acids according to this aspect of the disclosure. In certain embodiments, a target site for the gRNA is within the vector backbone. The vectors can be used to alter both a cellular endogenous target gene and the RNA-guided nuclease expression.

[SEQ ID NO: 14]
ATGACACAGTTCGAGGGCTTTACCAACCTGTATCAGGTGAGCAAGACACTG

CGGTTTGAGCTGATCCCACAGGGCAAGACCCTGAAGCACATCCAGGAGCAG

GGCTTCATCGAGGAGGACAAGGCCCGCAATGATCACTACAAGGAGCTGAAG

CCCATCATCGATCGGATCTACAAGACCTATGCCGACCAGTGCCTGCAGCTG

GTGCAGCTGGATTGGGAGAACCTGAGCGCCGCCATCGACTCCTATAGAAAG

GAGAAACCGAGGAGACAAGGAACGCCCTGATCGAGGAGCAGGCCACATAT

CGCAATGCCATCCACGACTACTTCATCGGCCGGACAGACAACCTGACCGAT

GCCATCAATAAGAGACACGCCGAGATCTACAAGGGCCTGTTCAAGGCCGAG

CTGTTTAATGGCAAGGTGCTGAAGCAGCTGGGCACCGTGACCACAACCGAG

CACGAGAACGCCCTGCTGCGGAGCTTCGACAAGTTTACAACCTACTTCTCC

GGCTTTTATGAGAACAGGAAGAACGTGTTCAGCGCCGAGGATATCAGCACA

GCCATCCCACACCGCATCGTGCAGGACAACTTCCCCAAGTTTAAGGAGAAT

TGTCACATCTTCACACGCCTGATCACCGCCGTGCCCAGCCTGCGGGAGCAC

TTTGAGAACGTGAAGAAGGCCATCGGCATCTTCGTGAGCACCTCCATCGAG

GAGGTGTTTTCCTTCCCTTTTTATAACCAGCTGCTGACACAGACCCAGATC

GACCTGTATAACCAGCTGCTGGGAGGAATCTCTCGGGAGGCAGGCACCGAG

AAGATCAAGGGCCTGAACGAGGTGCTGAATCTGGCCATCCAGAAGAATGAT

GAGACAGCCCACATCATCGCCTCCCTGCCACACAGATTCATCCCCCTGTTT

AAGCAGATCCTGTCCGATAGGAACACCCTGTCTTTCATCCTGGAGGAGTTT

AAGAGCGACGAGGAAGTGATCCAGTCCTTCTGCAAGTACAAGACACTGCTG

AGAAACGAGAACGTGCTGGAGACAGCCGAGGCCCTGTTTAACGAGCTGAAC

AGCATCGACCTGACACACATCTTCATCAGCCACAAGAAGCTGGAGACAATC

AGCAGCGCCCTGTGCGACCACTGGGATACACTGAGGAATGCCCTGTATGAG

CGGAGAATCTCCGAGCTGACAGGCAAGATCACCAAGTCTGCCAAGGAGAAG

GTGCAGCGCAGCCTGAAGCACGAGGATATCAACCTGCAGGAGATCATCTCT

GCCGCAGGCAAGGAGCTGAGCGAGGCCTTCAAGCAGAAAACCAGCGAGATC

```
CTGTCCCACGCACACGCCGCCCTGGATCAGCCACTGCCTACAACCCTGAAG
AAGCAGGAGGAGAAGGAGATCCTGAAGTCTCAGCTGGACAGCCTGCTGGGC
CTGTACCACCTGCTGGACTGGTTTGCCGTGGATGAGTCCAACGAGGTGGAC
CCCGAGTTCTCTGCCCGGCTGACCGGCATCAAGCTGGAGATGGAGCCTTCT
CTGAGCTTCTACAACAAGGCCAGAAATTATGCCACCAAGAAGCCCTACTCC
GTGGAGAAGTTCAAGCTGAACTTTCAGATGCCTACACTGGCCTCTGGCTGG
GACGTGAATAAGGAGAAGAACAATGGCGCCATCCTGTTTGTGAAGAACGGC
CTGTACTATCTGGGCATCATGCCAAAGCAGAAGGGCAGGTATAAGGCCCTG
AGCTTCGAGCCCACAGAGAAAACCAGCGAGGGCTTTGATAAGATGTACTAT
GACTACTTCCCTGATGCCGCCAAGATGATCCCAAAGTGCAGCACCCAGCTG
AAGGCCGTGACAGCCCACTTTCAGACCCACACAACCCCCATCCTGCTGTCC
AACAATTTCATCGAGCCTCTGGAGATCACAAAGGAGATCTACGACCTGAAC
AATCCTGAGAAGGAGCCAAAGAAGTTTCAGACAGCCTACGCCAAGAAACC
GGCGACCAGAAGGGCTACAGAGAGGCCCTGTGCAAGTGGATCGACTTCACA
AGGGATTTTCTGTCCAAGTATACCAAGACAACCTCTATCGATCTGTCTAGC
CTGCGGCCATCCTCTCAGTATAAGGACCTGGGCGAGTACTATGCCGAGCTG
AATCCCCTGCTGTACCACATCAGCTTCCAGAGAATCGCCGAGAAGGAGATC
ATGGATGCCGTGGAGACAGGCAAGCTGTACCTGTTCCAGATCTATAACAAG
GACTTTGCCAAGGGCCACCACGGCAAGCCTAATCTGCACACACTGTATTGG
ACCGGCCTGTTTTCTCCAGAGAACCTGGCCAAGACAAGCATCAAGCTGAAT
GGCCAGGCCGAGCTGTTCTACCGCCCTAAGTCCAGGATGAAGAGGATGGCA
CACCGGCTGGGAGAGAAGATGCTGAACAAGAAGCTGAAGGATCAGAAAACC
CCAATCCCCGACACCCTGTACCAGGAGCTGTACGACTATGTGAATCACAGA
CTGTCCCACGACCTGTCTGATGAGGCCAGGGCCCTGCTGCCCAACGTGATC
ACCAAGGAGGTGTCTCACGAGATCATCAAGGATAGGCGCTTTACCAGCGAC
AAGTTCTTTTTCCACGTGCCTATCACACTGAACTATCAGGCCGCCAATTCC
CCATCTAAGTTCAACCAGAGGGTGAATGCCTACCTGAAGGAGCACCCCGAG
ACACCTATCATCGGCATCGATCGGGGCGAGAGAAACCTGATCTATATCACA
GTGATCGACTCCACCGGCAAGATCCTGGAGCAGCGGAGCCTGAACACCATC
CAGCAGTTTGATTACCAGAAGAAGCTGGACAACAGGGAGAAGGAGAGGGTG
GCAGCAAGGCAGGCCTGGTCTGTGGTGGGCACAATCAAGGATCTGAAGCAG
GGCTATCTGAGCCAGGTCATCCACGAGATCGTGGACCTGATGATCCACTAC
CAGGCCGTGGTGGTGCTGGCGAACCTGAATTTCGGCTTTAAGAGCAAGAGG
ACCGGCATCGCCGAGAAGGCCGTGTACCAGCAGTTCGAGAAGATGCTGATC
GATAAGCTGAATTGCCTGGTGCTGAAGGACTATCCAGCAGAGAAAGTGGGA
GGCGTGCTGAACCCATACCAGCTGACAGACCAGTTCACCTCCTTTGCCAAG
ATGGGCACCCAGTCTGGCTTCCTGTTTTACGTGCCTGCCCCATATACATCT
AAGATCGATCCCCTGACCGGCTTCGTGGACCCCTTCGTGTGGAAAACCATC
AAGAATCACGAGAGCCGCAAGCACTTCCTGGAGGGCTTCGACTTTCTGCAC
TACGACGTGAAAACCGGCGACTTCATCCTGCACTTTAAGATGAACAGAAAT

CTGTCCTTCCAGAGGGGCCTGCCCGGCTTTATGCCTGCATGGGATATCGTG
TTCGAGAAGAACGAGACACAGTTTGACGCCAAGGGCACCCCTTTCATCGCC
GGCAAGAGAATCGTGCCAGTGATCGAGAATCACAGATTCACCGGCAGATAC
CGGGACCTGTATCCTGCCAACGAGCTGATCGCCCTGCTGGAGGAGAAGGGC
ATCGTGTTCAGGGATGGCTCCAACATCCTGCCAAAGCTGCTGGAGAATGAC
GATTCTCACGCCATCGACACCATGGTGGCCCTGATCCGCAGCGTGCTGCAG
ATGCGGAACTCCAATGCCGCCACAGGCGAGGACTATATCAACAGCCCCGTG
CGCGATCTGAATGGCGTGTGCTTCGACTCCCGGTTTCAGAACCCAGAGTGG
CCCATGGACGCCGATGCCAATGGCGCCTACCACATCGCCCTGAAGGGCCAG
CTGCTGCTGAATCACCTGAAGGAGAGCAAGGATCTGAAGCTGCAGAACGGC
ATCTCCAATCAGGACTGGCTGGCCTACATCCAGGAGCTGCGCAAC
```

Skilled artisans will be aware that the exemplary sequences presented herein may be modified in ways that do not affect the operating principles of the genome editing systems they embody. Accordingly, modified nucleotide or amino acid sequences that are truncated, fused to other sequences, or otherwise modified to have >50%, >60%, >70%, >80%, >85%, >90%, >91%, >92%, >93%, >94%, >95%, >96%, >97%, >98% or >99% sequence identity relative to the sequences presented herein are within the scope of this disclosure. So too are amino acid or nucleic acid sequences differing by 1, 2, 3, 4, 5, 6, 7, 8, 9, 10, 15, 20 or more residues from the sequences presented herein.

Turning next to the selection of inserts that will minimize disruption of nuclease structure, many of the inserts within the scope of this disclosure have been engineered to satisfy one or more of the following requirements: (i) the insert includes, at its 3' and 5' ends, 3-nucleotide codons for glycine or another small, flexible residue (e.g., alanine or valine), and encodes an amino acid sequence such as: G-[X]$_{6-10}$-G, where "X" denotes any amino acid, subject to the constraints set forth here; (ii) the insert does not introduce a stop codon, splice donor or acceptor, or other undesirable domain in the coding sequence; (iii) X is characterized by a hydrophilicity or hydrophobicity that will not disrupt the folding of the engineered protein or its final structure (e.g. phenylalanine); and (iv) X is not bulky (e.g. tryptophan), and is not a cysteine, proline or other amino acid that could disrupt the structure of the Cas9 by introducing a bend or causing steric interference with the surrounding protein, forming a sulfur bridge, etc.

In certain cases, inserts according to this disclosure can be generated according to the following heuristic:

1. For a target site (protospacer and PAM) within a cellular gene target of interest, identify all possible amino acid sequences that may be encoded by the target site sequence in all six possible reading frames;

2. Discard any nucleotide sequence reading frames that do not meet the design criteria set forth above (e.g., that encode a stop codon, or that encode peptides that would likely disrupt the structure of the surrounding protein due to hydrophobicity, bulk, etc.;

3. For each nucleotide sequence that is not discarded in step 2,
   a. add glycine codons to the 3' and 5' ends of the target site,
   b. if necessary, insert on the 5' end of the sequence between the glycine codon and the target site, one or two nucleotides to shift the target site sequence into a desired reading frame; and c. if necessary, insert, on the 3' end of the sequence between the target site and the glycine codon, one or two nucleotides to keep the 3' glycine codon and the subsequent peptide sequence in frame.

It should be noted that the inserts of the present disclosure are broadly compatible with RNA-guided nucleases, including without limitation Cas9, Cpf1, and other Class 2 nucleases and the various orthologs thereof, and nucleic acids encoding the same. In certain embodiments, the RNA-guided nuclease is Cas9. In certain embodiments, the RNA-guided nuclease is Cpf1. While certain examples of this disclosure focus on the use of inserts to regulate expression of S. aureus Cas9, the skilled artisan will appreciate that an insert of this disclosure may be adapted for use with other nucleases or orthologs. By way of example, an insert may be adapted for use in another nuclease or ortholog by (i) selecting an appropriate target site comprising a PAM sequence recognized by the nuclease or ortholog, and (ii) selecting an insertion site that is within a peptide loop that is (a) located on a surface of the nuclease protein, and/or (b) predicted to tolerate the insertion of the insert without alterations in folding or structure.

In use, the engineered nucleic acids according to this disclosure simultaneously provide a template for transcription and expression of genome editing system components and a substrate for cleavage or other editing by genome editing systems once expressed. In many (though not necessarily all) embodiments, cleavage of the engineered nucleic acid decreases or eliminates expression of one or more genome editing system components encoded by the engineered nucleic acid. Alternatively, or additionally, cleavage of the engineered nucleic acids can result in the formation of indel mutations that decrease the function of the genome editing system components. These outcomes, in turn, can provide a temporal limit to the genome editing activity caused by delivery of the engineered nucleic acids as compared to non-engineered nucleotides encoding similar components. For example, where a nucleic acid vector encoding a RNA-guided nuclease and gRNA under the control of constitutive promoters would be expected to drive ongoing, constitutive genome editing activity, the inclusion of an ogRNA target site in the same vector (whether in the backbone or the RNA-guided nuclease coding sequence) will result in a limited period of high expression of system components and a transient peak in genome editing activity, which will decrease as copies of the vector within each cell are cleaved and inactivated, over a period of hours, days, or weeks. It will be clear to the skilled artisan that temporal limitation of genome editing activity using the transiently active genome editing systems described herein can be advantageous in certain settings, for instance to limit the potential for off-target cutting, or to limit any potential cellular response to the genome editing system components.

In certain embodiments, the activity of the RNA-guided nuclease can be modulated via the nature of the ogRNA target sequence inserted into either the vector backbone or the RNA-guided nuclease coding sequence. For example, if the ogRNA target sequence comprises a consensus PAM sequence, the RNA-guided nuclease will edit the nucleic acid encoding the RNA-guided nuclease at a higher efficiency than a target sequence comprising a sub-optimal PAM. Accordingly, if a consensus PAM sequence is employed, expression of the RNA-guided nuclease will reflect a burst dose, while if a sub-optimal PAM sequence is employed, expression of the RNA-guided nuclease will reflect an extended dose. Exemplary consensus and sub-optimal PAM sequences for S. aureus Cas9 are listed in Table 5.

TABLE 5

Consensus and sub-optimal S. aureus Cas9 PAM sequences

| PAM | Description |
| --- | --- |
| NNGRRT | Consensus S. aureus PAM |
| NNGYRT | Sub-optimal PAM - substitute Y at R1 |
| NNGRYT | Sub-optimal PAM - substitute Y at R2 |
| NNGYYT | Sub-optimal PAM - substitutions at R1, R2 |
| NNGRRV | Sub-optimal PAM - substitution of V for T |
| NNGYRV | Sub-optimal PAM - substitutions at R1, T |
| NNGRYV | Sub-optimal PAM - substitutions at R2, T |
| NNHRRT | Sub-optimal PAM - substitution of H for G |
| NNHYRT | Sub-optimal PAM - substitution of H for G, R1 |
| NNHRYT | Sub-optimal PAM - substitution of H for G, R2 |
| NNHRRV | Sub-optimal PAM - substitution of H for G, V for T |
| NNHYRV | Sub-optimal PAM - substitution of H for G, R1, V for T |
| NNHRYV | Sub-optimal PAM - substitution of H for G, R2, V for T |
| NNHYYV | Sub-optimal PAM - substitution of H for G, R1, R2, V for T |

This overview has focused on a handful of exemplary embodiments that illustrate the principles of certain engineered nucleic acid vectors and engineered RNA-guided nucleases. For clarity, however, this disclosure encompasses modifications and variations that will be evident to those of skill in the art. For example, editing of the nucleic acid encoding the RNA-guided nuclease and the nuclei acid encoding the cellular endogenous target gene, as described herein, can be simultaneous or concomitant, however there is not necessarily a temporal restriction of such editing. With that in mind, the following disclosure is intended to illustrate the operating principles of genome editing systems more generally. What follows should not be understood as limiting, but rather illustrative of certain principles of genome editing systems, which, in combination with the instant disclosure, will inform those of skill in the art about additional implementations of and modifications that are within the scope of this disclosure.

Genome Editing Systems

The term "genome editing system" refers to any system having RNA-guided DNA editing activity. Genome editing systems of the present disclosure include at least two components adapted from naturally occurring CRISPR systems: a guide RNA (gRNA) and an RNA-guided nuclease. These two components form a complex that is capable of associating with a specific nucleic acid sequence and editing the DNA in or around that nucleic acid sequence, for instance by making one or more of a single strand break (an SSB or nick), a double strand break (a DSB) and/or a point mutation. In certain embodiments, the genome editing system is a transiently active genome editing system. In certain embodiments, the genome editing system can alter both a cellular endogenous target gene and the RNA-guided-nuclease expression. In certain embodiments, the gRNA/RNA-guided nuclease complex can cleave both the nucleic acid encoding the RNA-guided nuclease and the nucleic acid encoding the cellular endogenous target gene.

Naturally occurring CRISPR systems are organized evolutionarily into two classes and five types (Makarova et al. Nat Rev Microbiol. 2011 June; 9(6): 467-477 (Makarova), incorporated by reference herein), and while genome editing systems of the present disclosure may adapt components of any type or class of naturally occurring CRISPR system, the embodiments presented herein are generally adapted from Class 2, and type II or V CRISPR systems. Class 2 systems, which encompass types II and V, are characterized by relatively large, multidomain RNA-guided nuclease proteins (e.g., Cas9 or Cpf1) and one or more guide RNAs (e.g., a crRNA and, optionally, a tracrRNA) that form ribonucleoprotein (RNP) complexes that associate with (i.e. target) and cleave specific loci complementary to a targeting (or spacer) sequence of the crRNA. Genome editing systems according to the present disclosure similarly target and edit cellular DNA sequences, but differ significantly from CRISPR systems occurring in nature. For example, the unimolecular guide RNAs described herein do not occur in nature, and both guide RNAs and RNA-guided nucleases according to this disclosure may incorporate any number of non-naturally occurring modifications.

Genome editing systems can be implemented (e.g. administered or delivered to a cell or a subject) in a variety of ways, and different implementations may be suitable for distinct applications. For instance, a genome editing system is implemented, in certain embodiments, as a protein/RNA complex (a ribonucleoprotein, or RNP), which can be included in a pharmaceutical composition that optionally includes a pharmaceutically acceptable carrier and/or an encapsulating agent, such as a lipid or polymer micro- or nano-particle, micelle, liposome, etc. In certain embodiments, a genome editing system is implemented as one or more nucleic acids encoding the RNA-guided nuclease and guide RNA components described above (optionally with one or more additional components); in certain embodiments, the genome editing system is implemented as one or more vectors comprising such nucleic acids, for instance a viral vector such as an adeno-associated virus; and in certain embodiments, the genome editing system is implemented as a combination of any of the foregoing. Additional or modified implementations that operate according to the principles set forth herein will be apparent to the skilled artisan and are within the scope of this disclosure.

It should be noted that the genome editing systems of the present disclosure can be targeted to a single specific nucleotide sequence, or may be targeted to—and capable of editing in parallel—two or more specific nucleotide sequences through the use of two or more guide RNAs. The use of multiple gRNAs is referred to as "multiplexing" throughout this disclosure, and can be employed to target multiple, unrelated target sequences of interest, or to form multiple SSBs or DSBs within a single target domain and, in some cases, to generate specific edits within such target domain. For example, International Patent Publication No. WO 2015/138510 by Maeder et al. (Maeder), which is incorporated by reference herein, describes a genome editing system for correcting a point mutation (C.2991+1655A to G) in the human CEP290 gene that results in the creation of a cryptic splice site, which in turn reduces or eliminates the function of the gene. The genome editing system of Maeder utilizes two guide RNAs targeted to sequences on either side of (i.e. flanking) the point mutation, and forms DSBs that flank the mutation. This, in turn, promotes deletion of the intervening sequence, including the mutation, thereby eliminating the cryptic splice site and restoring normal gene function.

As another example, WO 2016/073990 by Cotta-Ramusino, et al. ("Cotta-Ramusino"), incorporated by reference herein, describes a genome editing system that utilizes twogRNAs in combination with a Cas9 nickase (a Cas9 that makes a single strand nick such as S. pyogenes D10A), an arrangement termed a "dual-nickase system." The dual-nickase system of Cotta-Ramusino is configured to make two nicks on opposite strands of a sequence of interest that are offset by one or more nucleotides, which nicks combine to create a double strand break having an overhang (5' in the case of Cotta-Ramusino, though 3' overhangs are also possible). The overhang, in turn, can facilitate homology directed repair events in some circumstances. And, as another example, WO 2015/070083 by Palestrant et al. ("Palestrant", incorporated by reference herein) describes a gRNA targeted to a nucleotide sequence encoding Cas9 (referred to as a "governing RNA"), which can be included in a genome editing system comprising one or more additional gRNAs to permit transient expression of a Cas9 that might otherwise be constitutively expressed, for example in some virally transduced cells. These multiplexing applications are intended to be exemplary, rather than limiting, and the skilled artisan will appreciate that other applications of multiplexing are generally compatible with the genome editing systems described here.

Genome editing systems can, in some instances, form double strand breaks that are repaired by cellular DNA double-strand break mechanisms such as NHEJ or HDR. These mechanisms are described throughout the literature, for example by Davis & Maizels, PNAS, 111(10):E924-932, Mar. 11, 2014 (Davis) (describing Alt-HDR); Frit et al. DNA Repair 17(2014) 81-97 (Frit) (describing Alt-NHEJ); and Iyama and Wilson III, DNA Repair (Amst.) 2013-August; 12(8): 620-636 (Iyama) (describing canonical HDR and NHEJ pathways generally).

Where genome editing systems operate by forming DSBs, such systems optionally include one or more components that promote or facilitate a particular mode of double-strand break repair or a particular repair outcome. For instance, Cotta-Ramusino also describes genome editing systems in which a single-stranded oligonucleotide "donor template" is added; the donor template is incorporated into a target region of cellular DNA that is cleaved by the genome editing system, and can result in a change in the target sequence.

In certain embodiments, genome editing systems modify a target sequence, or modify expression of a gene in or near the target sequence, without causing single- or double-strand breaks. For example, a genome editing system may include an RNA-guided nuclease fused to a functional domain that acts on DNA, thereby modifying the target sequence or its expression. As one example, an RNA-guided nuclease can be connected to (e.g. fused to) a cytidine deaminase functional domain, and may operate by generating targeted C-to-A substitutions. Exemplary nuclease/deaminase fusions are described in Komor et al. Nature 533, 420-424 (19 May 2016) ("Komor"), which is incorporated by reference. Alternatively, a genome editing system may utilize a cleavage-inactivated (i.e. a "dead") nuclease, such as a dead Cas9 (dCas9), and may operate by forming stable complexes on one or more targeted regions of cellular DNA, thereby interfering with functions involving the targeted region(s) including, without limitation, mRNA transcription, chromatin remodeling, etc.

Guide RNA (gRNA) Molecules

The terms "guide RNA" and "gRNA" refer to any nucleic acid that promotes the specific association (or "targeting") of an RNA-guided nuclease such as a Cas9 or a Cpf1 to a target sequence such as a genomic or episomal sequence in a cell. gRNAs can be unimolecular (comprising a single RNA molecule, and referred to alternatively as chimeric), or modular (comprising more than one, and typically two, separate RNA molecules, such as a crRNA and a tracrRNA, which are usually associated with one another, for instance by duplexing). gRNAs and their component parts are described throughout the literature, for instance in Briner et al. (Molecular Cell 56(2), 333-339, Oct. 23, 2014 (Briner), which is incorporated by reference), and in Cotta-Ramusino.

In bacteria and archaea, type II CRISPR systems generally comprise an RNA-guided nuclease protein such as Cas9, a CRISPR RNA (crRNA) that includes a 5' region that is complementary to a foreign sequence, and a trans-activating crRNA (tracrRNA) that includes a 5' region that is complementary to, and forms a duplex with, a 3' region of the crRNA. While not intending to be bound by any theory, it is thought that this duplex facilitates the formation of—and is necessary for the activity of—the Cas9/gRNA complex. As type II CRISPR systems were adapted for use in gene editing, it was discovered that the crRNA and tracrRNA could be joined into a single unimolecular or chimeric guide RNA, for instance, but not by way of limitation, by means of a four nucleotide (e.g. GAAA) "tetraloop" or "linker" sequence bridging complementary regions of the crRNA (at its 3' end) and the tracrRNA (at its 5' end). (Mali et al. Science. 2013 Feb. 15; 339(6121): 823-826 ("Mali"); Jiang et al. Nat Biotechnol. 2013 March; 31(3): 233-239 ("Jiang"); and Jinek et al., 2012 Science August 17; 337 (6096): 816-821 ("Jinek"), all of which are incorporated by reference herein.)

Guide RNAs, whether unimolecular or modular, include a "targeting domain" that is fully or partially complementary to a target domain within a target sequence, such as a DNA sequence in the genome of a cell where editing is desired. Targeting domains are referred to by various names in the literature, including without limitation "guide sequences" (Hsu et al., Nat Biotechnol. 2013 September; 31(9): 827-832, ("Hsu"), incorporated by reference herein), "complementarity regions" (Cotta-Ramusino), "spacers" (Briner) and generically as "crRNAs" (Jiang). Irrespective of the names they are given, targeting domains are typically 10-30 nucleotides in length, and in certain embodiments are 16-24 nucleotides in length (for instance, 16, 17, 18, 19, 20, 21, 22, 23 or 24 nucleotides in length), and are at or near the 5' terminus of in the case of a Cas9 gRNA, and at or near the 3' terminus in the case of a Cpf1 gRNA.

In addition to the targeting domains, gRNAs typically (but not necessarily, as discussed below) include a plurality of domains that may influence the formation or activity of gRNA/Cas9 complexes. For instance, as mentioned above, the duplexed structure formed by first and secondary complementarity domains of a gRNA (also referred to as a repeat:anti-repeat duplex) interacts with the recognition (REC) lobe of Cas9 and can mediate the formation of Cas9/gRNA complexes. (Nishimasu et al., Cell 156, 935-949, Feb. 27, 2014 (Nishimasu 2014) and Nishimasu et al., Cell 162, 1113-1126, Aug. 27, 2015 (Nishimasu 2015), both incorporated by reference herein). It should be noted that the first and/or second complementarity domains may contain one or more poly-A tracts, which can be recognized by RNA polymerases as a termination signal. The sequence of the first and second complentarity domains are, therefore, optionally modified to eliminate these tracts and promote the complete in vitro transcription of gRNAs, for instance through the use of A-G swaps as described in Briner, or A-U swaps. These and other similar modifications to the first and second complementarity domains are within the scope of the present disclosure.

Along with the first and second complementarity domains, Cas9 gRNAs typically include two or more additional duplexed regions that are involved in nuclease activity in vivo but not necessarily in vitro. (Nishimasu 2015). A first stem-loop one near the 3' portion of the second complementarity domain is referred to variously as the "proximal domain," (Cotta-Ramusino) "stem loop 1" (Nishimasu 2014 and 2015) and the "nexus" (Briner). One or more additional stem loop structures are generally present near the 3' end of the gRNA, with the number varying by species: *S. pyogenes* gRNAs typically include two 3' stem loops (for a total of four stem loop structures including the repeat:anti-repeat duplex), while *S. aureus* and other species have only one (for a total of three stem loop structures). A description of conserved stem loop structures (and gRNA structures more generally) organized by species is provided in Briner.

While the foregoing description has focused on gRNAs for use with Cas9, it should be appreciated that other RNA-guided nucleases have been (or may in the future be) discovered or invented which utilize gRNAs that differ in some ways from those described to this point. For instance, Cpf1 ("CRISPR from *Prevotella* and *Franciscella* 1") is a recently discovered RNA-guided nuclease that does not require a tracrRNA to function. (Zetsche et al., 2015, Cell 163, 759-771 Oct. 22, 2015 (Zetsche I), incorporated by reference herein). A gRNA for use in a Cpf1 genome editing system generally includes a targeting domain and a complementarity domain (alternately referred to as a "handle"). It should also be noted that, in gRNAs for use with Cpf1, the targeting domain is usually present at or near the 3' end, rather than the 5' end as described above in connection with Cas9 gRNAs (the handle is at or near the 5' end of a Cpf1 gRNA).

Those of skill in the art will appreciate, however, that although structural differences may exist between gRNAs from different prokaryotic species, or between Cpf1 and Cas9 gRNAs, the principles by which gRNAs operate are generally consistent. Because of this consistency of operation, gRNAs can be defined, in broad terms, by their targeting domain sequences, and skilled artisans will appreciate that a given targeting domain sequence can be incorporated in any suitable gRNA, including a unimolecular or modular gRNA, or a gRNA that includes one or more chemical modifications and/or sequential modifications (substitutions, additional nucleotides, truncations, etc.). Thus, for economy of presentation in this disclosure, gRNAs may be described solely in terms of their targeting domain sequences.

More generally, skilled artisans will appreciate that some aspects of the present disclosure relate to systems, methods and compositions that can be implemented using multiple RNA-guided nucleases. For this reason, unless otherwise specified, the term gRNA should be understood to encompass any suitable gRNA that can be used with any RNA-guided nuclease, and not only those gRNAs that are compatible with a particular species of Cas9 or Cpf1. By way of illustration, the term gRNA can, in certain embodiments, include a gRNA for use with any RNA-guided nuclease occurring in a Class 2 CRISPR system, such as a type II or type V or CRISPR system, or an RNA-guided nuclease derived or adapted therefrom.

gRNA Design

Methods for selection and validation of target sequences as well as off-target analyses have been described previously, e.g., in Mali; Hsu; Fu et al., 2014 Nat biotechnol 32(3): 279-84, Heigwer et al., 2014 Nat methods 11(2):122-3; Bae et al. (2014) Bioinformatics 30(10): 1473-5; and Xiao A et al. (2014) Bioinformatics 30(8): 1180-1182. Each of these references is incorporated by reference herein. As a non-limiting example, gRNA design can involve the use of a software tool to optimize the choice of potential target sequences corresponding to a user's target sequence, e.g., to minimize total off-target activity across the genome. While off-target activity is not limited to cleavage, the cleavage efficiency at each off-target sequence can be predicted, e.g., using an experimentally-derived weighting scheme. These and other guide selection methods are described in detail in Maeder and Cotta-Ramusino.

gRNA Modifications

The activity, stability, or other characteristics of gRNAs can be altered through the incorporation of certain modifications. As one example, transiently expressed or delivered nucleic acids can be prone to degradation by, e.g., cellular nucleases. Accordingly, the gRNAs described herein can contain one or more modified nucleosides or nucleotides which introduce stability toward nucleases. While not wishing to be bound by theory it is also believed that certain modified gRNAs described herein can exhibit a reduced innate immune response when introduced into cells. Those of skill in the art will be aware of certain cellular responses commonly observed in cells, e.g., mammalian cells, in response to exogenous nucleic acids, particularly those of viral or bacterial origin. Such responses, which can include induction of cytokine expression and release and cell death, may be reduced or eliminated altogether by the modifications presented herein.

Certain exemplary modifications discussed in this section can be included at any position within a gRNA sequence including, without limitation at or near the 5' end (e.g., within 1-10, 1-5, or 1-2 nucleotides of the 5' end) and/or at or near the 3' end (e.g., within 1-10, 1-5, or 1-2 nucleotides of the 3' end). In some cases, modifications are positioned within functional motifs, such as the repeat-anti-repeat duplex of a Cas9 gRNA, a stem loop structure of a Cas9 or Cpf1 gRNA, and/or a targeting domain of a gRNA.

As one example, the 5' end of a gRNA can include a eukaryotic mRNA cap structure or cap analog (e.g., a G(5')ppp(5')G cap analog, a m7G(5')ppp(5')G cap analog, or a 3'-O-Me-m7G(5')ppp(5')G anti reverse cap analog (ARCA)), as shown below:

nosine polymerase (e.g., *E. coli* Poly(A)Polymerase), or in vivo by means of a polyadenylation sequence, as described in Maeder.

It should be noted that the modifications described herein can be combined in any suitable manner, e.g. a gRNA, whether transcribed in vivo from a DNA vector, or in vitro transcribed gRNA, can include either or both of a 5' cap structure or cap analog and a 3' polyA tract.

Guide RNAs can be modified at a 3' terminal U ribose. For example, the two terminal hydroxyl groups of the U ribose can be oxidized to aldehyde groups and a concomitant opening of the ribose ring to afford a modified nucleoside as shown below:

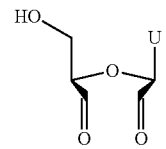

wherein "U" can be an unmodified or modified uridine.

The 3' terminal U ribose can be modified with a 2'3' cyclic phosphate as shown below:

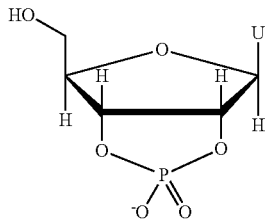

wherein "U" can be an unmodified or modified uridine.

Guide RNAs can contain 3' nucleotides which can be stabilized against degradation, e.g., by incorporating one or more of the modified nucleotides described herein. In certain

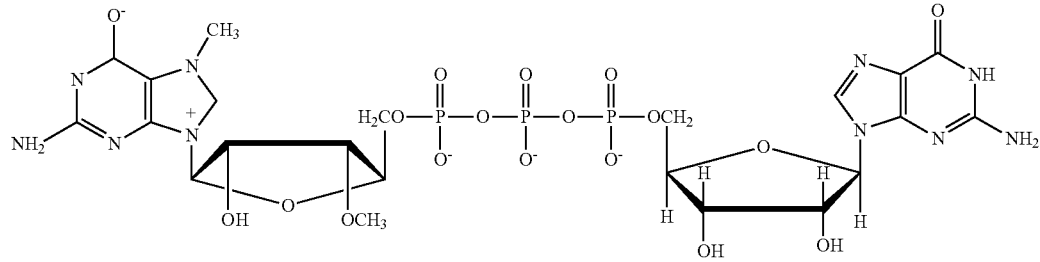

The cap or cap analog can be included during either chemical synthesis or in vitro transcription of the gRNA.

Along similar lines, the 5' end of the gRNA can lack a 5' triphosphate group. For instance, in vitro transcribed gRNAs can be phosphatase-treated (e.g., using calf intestinal alkaline phosphatase) to remove a 5' triphosphate group.

Another common modification involves the addition, at the 3' end of a gRNA, of a plurality (e.g., 1-10, 10-20, or 25-200) of adenine (A) residues referred to as a polyA tract. The polyA tract can be added to a gRNA during chemical synthesis, following in vitro transcription using a polyadeembodiments, uridines can be replaced with modified uridines, e.g., 5-(2-amino)propyl uridine, and 5-bromo uridine, or with any of the modified uridines described herein; adenosines and guanosines can be replaced with modified adenosines and guanosines, e.g., with modifications at the 8-position, e.g., 8-bromo guanosine, or with any of the modified adenosines or guanosines described herein.

In certain embodiments, sugar-modified ribonucleotides can be incorporated into the gRNA, e.g., wherein the 2' OH-group is replaced by a group selected from H, —OR, —R (wherein R can be, e.g., alkyl, cycloalkyl, aryl, aralkyl, heteroaryl or sugar), halo, —SH, —SR (wherein R can be, e.g., alkyl, cycloalkyl, aryl, aralkyl, heteroaryl or sugar), amino (wherein amino can be, e.g., $NH_2$; alkylamino, dialkylamino, heterocyclyl, arylamino, diarylamino, heteroarylamino, diheteroarylamino, or amino acid); or cyano (—CN). In certain embodiments, the phosphate backbone can be modified as described herein, e.g., with a phosphothioate (PhTx) group. In certain embodiments, one or more of the nucleotides of the gRNA can each independently be a modified or unmodified nucleotide including, but not limited to 2'-sugar modified, such as, 2'-O-methyl, 2'-O-methoxyethyl, or 2'-Fluoro modified including, e.g., 2'-F or 2'-O-methyl, adenosine (A), 2'-F or 2'-O-methyl, cytidine (C), 2'-F or 2'-O-methyl, uridine (U), 2'-F or 2'-O-methyl, thymidine (T), 2'-F or 2'-O-methyl, guanosine (G), 2'-O-methoxyethyl-5-methyluridine (Teo), 2'-O-methoxyethyladenosine (Aeo), 2'-O-methoxyethyl-5-methylcytidine (m5Ceo), and any combinations thereof.

Guide RNAs can also include "locked" nucleic acids (LNA) in which the 2' OH-group can be connected, e.g., by a C1-6 alkylene or C1-6 heteroalkylene bridge, to the 4' carbon of the same ribose sugar. Any suitable moiety can be used to provide such bridges, include without limitation methylene, propylene, ether, or amino bridges; O-amino (wherein amino can be, e.g., $NH_2$; alkylamino, dialkylamino, heterocyclyl, arylamino, diarylamino, heteroarylamino, or diheteroarylamino, ethylenediamine, or polyamino) and aminoalkoxy or $O(CH_2)_n$-amino (wherein amino can be, e.g., $NH_2$; alkylamino, dialkylamino, heterocyclyl, arylamino, diarylamino, heteroarylamino, or diheteroarylamino, ethylenediamine, or polyamino).

In certain embodiments, a gRNA can include a modified nucleotide which is multicyclic (e.g., tricyclo; and "unlocked" forms, such as glycol nucleic acid (GNA) (e.g., R-GNA or S-GNA, where ribose is replaced by glycol units attached to phosphodiester bonds), or threose nucleic acid (TNA, where ribose is replaced with α-L-threofuranosyl-(3'→2')).

Generally, gRNAs include the sugar group ribose, which is a 5-membered ring having an oxygen. Exemplary modified gRNAs can include, without limitation, replacement of the oxygen in ribose (e.g., with sulfur (S), selenium (Se), or alkylene, such as, e.g., methylene or ethylene); addition of a double bond (e.g., to replace ribose with cyclopentenyl or cyclohexenyl); ring contraction of ribose (e.g., to form a 4-membered ring of cyclobutane or oxetane); ring expansion of ribose (e.g., to form a 6- or 7-membered ring having an additional carbon or heteroatom, such as for example, anhydrohexitol, altritol, mannitol, cyclohexanyl, cyclohexenyl, and morpholino that also has a phosphoramidate backbone). Although the majority of sugar analog alterations are localized to the 2' position, other sites are amenable to modification, including the 4' position. In certain embodiments, a gRNA comprises a 4'-S, 4'-Se or a 4'-C-aminomethyl-2'-O-Me modification.

In certain embodiments, deaza nucleotides, e.g., 7-deaza-adenosine, can be incorporated into the gRNA. In certain embodiments, O- and N-alkylated nucleotides, e.g., N6-methyl adenosine, can be incorporated into the gRNA. In certain embodiments, one or more or all of the nucleotides in a gRNA are deoxynucleotides.

RNA-Guided Nucleases

RNA-guided nucleases according to the present disclosure include, but are not limited to, naturally-occurring Class 2 CRISPR nucleases such as Cas9, and Cpf1, as well as other nucleases derived or obtained therefrom. In functional terms, RNA-guided nucleases are defined as those nucleases that: (a) interact with (e.g. complex with) a gRNA; and (b) together with the gRNA, associate with, and optionally cleave or modify, a target region of a DNA that includes (i) a sequence complementary to the targeting domain of the gRNA and, optionally, (ii) an additional sequence referred to as a "protospacer adjacent motif," or "PAM," which is described in greater detail below. As the following examples will illustrate, RNA-guided nucleases can be defined, in broad terms, by their PAM specificity and cleavage activity, even though variations may exist between individual RNA-guided nucleases that share the same PAM specificity or cleavage activity. Skilled artisans will appreciate that some aspects of the present disclosure relate to systems, methods and compositions that can be implemented using any suitable RNA-guided nuclease having a certain PAM specificity and/or cleavage activity. For this reason, unless otherwise specified, the term RNA-guided nuclease should be understood as a generic term, and not limited to any particular type (e.g. Cas9 vs. Cpf1), species (e.g. S. pyogenes vs. S. aureus) or variation (e.g. full-length vs. truncated or split; naturally-occurring PAM specificity vs. engineered PAM specificity, etc.) of RNA-guided nuclease.

The PAM sequence takes its name from its sequential relationship to the "protospacer" sequence that is complementary to gRNA targeting domains (or "spacers"). Together with protospacer sequences, PAM sequences define target regions or sequences for specific RNA-guided nuclease/gRNA combinations.

Various RNA-guided nucleases may require different sequential relationships between PAMs and protospacers. In general, Cas9s recognize PAM sequences that are 3' of the protospacer as visualized on the bottom or non-complementary strand:

```
5'-------------[protospacer]----3'    complementary

3'--------[PAM]----------------5'     non-
                                      complementary
```

Cpf1, on the other hand, generally recognizes PAM sequences that are 5' of the protospacer as visualized on the bottom or non-complementary strand:

```
5'---------[protospacer]--------3'    complementary

3'---------------------[PAM]---5'     non-
                                      complementary
```

In addition to recognizing specific sequential orientations of PAMs and protospacers, RNA-guided nucleases can also recognize specific PAM sequences. S. aureus Cas9, for instance, recognizes a PAM sequence of NNGRRT or NNGRRV, wherein the N residues are immediately 3' of the region recognized by the gRNA targeting domain. S. pyogenes Cas9 recognizes NGG PAM sequences. And F. novicida Cpf1 recognizes a TTN PAM sequence. PAM sequences have been identified for a variety of RNA-guided nucleases, and a strategy for identifying novel PAM sequences has been described by Shmakov et al., 2015, Molecular Cell 60, 385-397, Nov. 5, 2015. It should also be noted that engineered RNA-guided nucleases can have PAM specificities that differ from the PAM specificities of reference molecules (for instance, in the case of an engineered RNA-guided nuclease, the reference molecule may be the naturally occurring variant from which the RNA-guided nuclease is derived, or the naturally occurring variant having the greatest amino acid sequence homology to the engineered RNA-guided nuclease).

In addition to their PAM specificity, RNA-guided nucleases can be characterized by their DNA cleavage activity: naturally-occurring RNA-guided nucleases typically form DSBs in target nucleic acids, but engineered variants have been produced that generate only SSBs (discussed above) Ran & Hsu, et al., Cell 154(6), 1380-1389, Sep. 12, 2013 (Ran), incorporated by reference herein), or that do not cut at all.

Cas9

Crystal structures have been determined for *S. pyogenes* Cas9 (Jinek 2014), and for *S. aureus* Cas9 in complex with a unimolecular guide RNA and a target DNA (Nishimasu 2014; Anders 2014; and Nishimasu 2015).

A naturally occurring Cas9 protein comprises two lobes: a recognition (REC) lobe and a nuclease (NUC) lobe; each of which comprise particular structural and/or functional domains. The REC lobe comprises an arginine-rich bridge helix (BH) domain, and at least one REC domain (e.g. a REC1 domain and, optionally, a REC2 domain). The REC lobe does not share structural similarity with other known proteins, indicating that it is a unique functional domain. While not wishing to be bound by any theory, mutational analyses suggest specific functional roles for the BH and REC domains: the BH domain appears to play a role in gRNA:DNA recognition, while the REC domain is thought to interact with the repeat:anti-repeat duplex of the gRNA and to mediate the formation of the Cas9/gRNA complex.

The NUC lobe comprises a RuvC domain, an HNH domain, and a PAM-interacting (PI) domain. The RuvC domain shares structural similarity to retroviral integrase superfamily members and cleaves the non-complementary (i.e. bottom) strand of the target nucleic acid. It may be formed from two or more split RuvC motifs (such as RuvC I, RuvC II, and RuvC III in *S. pyogenes* and *S. aureus*). The HNH domain, meanwhile, is structurally similar to FINN endonuclease motifs, and cleaves the complementary (i.e. top) strand of the target nucleic acid. The PI domain, as its name suggests, contributes to PAM specificity.

While certain functions of Cas9 are linked to (but not necessarily fully determined by) the specific domains set forth above, these and other functions may be mediated or influenced by other Cas9 domains, or by multiple domains on either lobe. For instance, in *S. pyogenes* Cas9, as described in Nishimasu 2014, the repeat:antirepeat duplex of the gRNA falls into a groove between the REC and NUC lobes, and nucleotides in the duplex interact with amino acids in the BH, PI, and REC domains. Some nucleotides in the first stem loop structure also interact with amino acids in multiple domains (PI, BH and REC1), as do some nucleotides in the second and third stem loops (RuvC and PI domains).

Cpf1

The crystal structure of *Acidaminococcus* sp. Cpf1 in complex with crRNA and a double-stranded (ds) DNA target including a TTTN PAM sequence has been solved by Yamano et al. (Cell. 2016 May 5; 165(4): 949-962 (Yamano), incorporated by reference herein). Cpf1, like Cas9, has two lobes: a REC (recognition) lobe, and a NUC (nuclease) lobe. The REC lobe includes REC1 and REC2 domains, which lack similarity to any known protein structures. The NUC lobe, meanwhile, includes three RuvC domains (RuvC-I, -II and -III) and a BH domain. However, in contrast to Cas9, the Cpf1 REC lobe lacks an HNH domain, and includes other domains that also lack similarity to known protein structures: a structurally unique PI domain, three Wedge (WED) domains (WED-I, -II and -III), and a nuclease (Nuc) domain.

While Cas9 and Cpf1 share similarities in structure and function, it should be appreciated that certain Cpf1 activities are mediated by structural domains that are not analogous to any Cas9 domains. For instance, cleavage of the complementary strand of the target DNA appears to be mediated by the Nuc domain, which differs sequentially and spatially from the HNH domain of Cas9. Additionally, the non-targeting portion of Cpf1 gRNA (the handle) adopts a pseudoknot structure, rather than a stem loop structure formed by the repeat:antirepeat duplex in Cas9 gRNAs.

Modifications of RNA-Guided Nucleases

The RNA-guided nucleases described above have activities and properties that can be useful in a variety of applications, but the skilled artisan will appreciate that RNA-guided nucleases can also be modified in certain instances, to alter cleavage activity, PAM specificity, or other structural or functional features.

Turning first to modifications that alter cleavage activity, mutations that reduce or eliminate the activity of domains within the NUC lobe have been described above. Exemplary mutations that may be made in the RuvC domains, in the Cas9 HNH domain, or in the Cpf1 Nuc domain are described in Ran and Yamano, as well as in Cotta-Ramusino. In general, mutations that reduce or eliminate activity in one of the two nuclease domains result in RNA-guided nucleases with nickase activity, but it should be noted that the type of nickase activity varies depending on which domain is inactivated. As one example, inactivation of a RuvC domain of a Cas9 will result in a nickase that cleaves the complementary or top strand as shown below (where C denotes the site of cleavage):

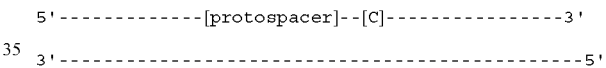

On the other hand, inactivation of a Cas9 HNH domain results in a nickase that cleaves the bottom or non-complementary strand:

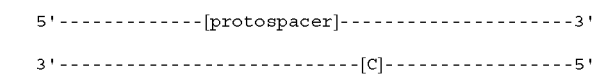

Modifications of PAM specificity relative to naturally occurring Cas9 reference molecules have been described by Kleinstiver et al. for both *S. pyogenes* (Kleinstiver et al., Nature. 2015 Jul. 23; 523(7561):481-5 (Kleinstiver I) and *S. aureus* (Kleinstiver et al., Nat Biotechnol. 2015 December; 33(12): 1293-1298 (Klienstiver II)). Kleinstiver et al. have also described modifications that improve the targeting fidelity of Cas9 (Nature, 2016 Jan. 28; 529, 490-495 (Kleinstiver III)). Each of these references is incorporated by reference herein.

RNA-guided nucleases have been split into two or more parts, as described by Zetsche et al. (Nat Biotechnol. 2015 February; 33(2):139-42 (Zetsche II), incorporated by reference), and by Fine et al. (Sci Rep. 2015 Jul. 1; 5:10777 (Fine), incorporated by reference).

RNA-guided nucleases can be, in certain embodiments, size-optimized or truncated, for instance via one or more deletions that reduce the size of the nuclease while still retaining gRNA association, target and PAM recognition, and cleavage activities. In certain embodiments, RNA guided nucleases are bound, covalently or non-covalently, to another polypeptide, nucleotide, or other structure, optionally by means of a linker. Exemplary bound nucleases and linkers are described by Guilinger et al., Nature Biotechnology 32, 577-582 (2014), which is incorporated by reference for all purposes herein.

RNA-guided nucleases also optionally include a tag, such as, but not limited to, a nuclear localization signal to facilitate movement of RNA-guided nuclease protein into the nucleus. In certain embodiments, the RNA-guided nuclease can incorporate C- and/or N-terminal nuclear localization signals. Nuclear localization sequences are known in the art and are described in Maeder and elsewhere.

The foregoing list of modifications is intended to be exemplary in nature, and the skilled artisan will appreciate, in view of the instant disclosure, that other modifications may be possible or desirable in certain applications. For brevity, therefore, exemplary systems, methods and compositions of the present disclosure are presented with reference to particular RNA-guided nucleases, but it should be understood that the RNA-guided nucleases used may be modified in ways that do not alter their operating principles. Such modifications are within the scope of the present disclosure.

Nucleic Acids Encoding RNA-Guided Nucleases

Nucleic acids encoding RNA-guided nucleases, e.g., Cas9, Cpf1 or functional fragments thereof, are provided herein. Exemplary nucleic acids encoding RNA-guided nucleases have been described previously (see, e.g., Cong 2013; Wang 2013; Mali 2013; Jinek 2012).

In some cases, a nucleic acid encoding an RNA-guided nuclease can be a synthetic nucleic acid sequence. For example, the synthetic nucleic acid molecule can be chemically modified. In certain embodiments, an mRNA encoding an RNA-guided nuclease will have one or more (e.g., all) of the following properties: it can be capped; polyadenylated; and substituted with 5-methylcytidine and/or pseudouridine.

Synthetic nucleic acid sequences can also be codon optimized, e.g., at least one non-common codon or less-common codon has been replaced by a common codon. For example, the synthetic nucleic acid can direct the synthesis of an optimized messenger mRNA, e.g., optimized for expression in a mammalian expression system, e.g., described herein. Examples of codon optimized Cas9 coding sequences are presented in Cotta-Ramusino.

In addition, or alternatively, a nucleic acid encoding an RNA-guided nuclease may comprise a nuclear localization sequence (NLS). Nuclear localization sequences are known in the art.

Functional Analysis of Candidate Molecules

Candidate RNA-guided nucleases, gRNAs, and complexes thereof, can be evaluated by standard methods known in the art. See, e.g. Cotta-Ramusino. The stability of RNP complexes may be evaluated by differential scanning fluorimetry, as described below.

Differential Scanning Fluorimetry (DSF)

The thermostability of ribonucleoprotein (RNP) complexes comprising gRNAs and RNA-guided nucleases can be measured via DSF. The DSF technique measures the thermostability of a protein, which can increase under favorable conditions such as the addition of a binding RNA molecule, e.g., a gRNA.

A DSF assay can be performed according to any suitable protocol, and can be employed in any suitable setting, including without limitation (a) testing different conditions (e.g. different stoichiometric ratios of gRNA:RNA-guided nuclease protein, different buffer solutions, etc.) to identify optimal conditions for RNP formation; and (b) testing modifications (e.g. chemical modifications, alterations of sequence, etc.) of an RNA-guided nuclease and/or a gRNA to identify those modifications that improve RNP formation or stability. One readout of a DSF assay is a shift in melting temperature of the RNP complex; a relatively high shift suggests that the RNP complex is more stable (and may thus have greater activity or more favorable kinetics of formation, kinetics of degradation, or another functional characteristic) relative to a reference RNP complex characterized by a lower shift. When the DSF assay is deployed as a screening tool, a threshold melting temperature shift may be specified, so that the output is one or more RNPs having a melting temperature shift at or above the threshold. For instance, the threshold can be 5-10° C. (e.g. 5°, 6°, 7°, 8°, 9°, 10°) or more, and the output may be one or more RNPs characterized by a melting temperature shift greater than or equal to the threshold.

Two non-limiting examples of DSF assay conditions are set forth below:

To determine the best solution to form RNP complexes, a fixed concentration (e.g. 2 µM) of Cas9 in water+10× SYPRO Orange® (Life Technologies cat#S-6650) is dispensed into a 384 well plate. An equimolar amount of gRNA diluted in solutions with varied pH and salt is then added. After incubating at room temperature for 10' and brief centrifugation to remove any bubbles, a Bio-Rad CFX384™ Real-Time System C1000 Touch™ Thermal Cycler with the Bio-Rad CFX Manager software is used to run a gradient from 20° C. to 90° C. with a 1° C. increase in temperature every 10 seconds.

The second assay consists of mixing various concentrations of gRNA with fixed concentration (e.g. 2 µM) Cas9 in optimal buffer from assay 1 above and incubating (e.g. at RT for 10') in a 384 well plate. An equal volume of optimal buffer+10×SYPRO Orange® (Life Technologies cat#S-6650) is added and the plate sealed with Microseal® B adhesive (MSB-1001). Following brief centrifugation to remove any bubbles, a Bio-Rad CFX384™ Real-Time System C1000 Touch™ Thermal Cycler with the Bio-Rad CFX Manager software is used to run a gradient from 20° C. to 90° C. with a 1° C. increase in temperature every 10 seconds.

Genome Editing Strategies

The genome editing systems described above are used, in various embodiments of the present disclosure, to generate edits in (i.e. to alter) targeted regions of DNA within or obtained from a cell. Various strategies are described herein to generate particular edits, and these strategies are generally described in terms of the desired repair outcome, the number and positioning of individual edits (e.g. SSBs or DSBs), and the target sites of such edits.

Genome editing strategies that involve the formation of SSBs or DSBs are characterized by repair outcomes including: (a) deletion of all or part of a targeted region; (b) insertion into or replacement of all or part of a targeted region; or (c) interruption of all or part of a targeted region. This grouping is not intended to be limiting, or to be binding to any particular theory or model, and is offered solely for economy of presentation. Skilled artisans will appreciate that the listed outcomes are not mutually exclusive and that some repairs may result in other outcomes. The description of a particular editing strategy or method should not be understood to require a particular repair outcome unless otherwise specified.

Replacement of a targeted region generally involves the replacement of all or part of the existing sequence within the targeted region with a homologous sequence, for instance through gene correction or gene conversion, two repair outcomes that are mediated by HDR pathways. HDR is promoted by the use of a donor template, which can be single-stranded or double-stranded, as described in greater detail below. Single- or double-stranded templates can be exogenous, in which case they will promote gene correction, or they can be endogenous (e.g. a homologous sequence within the cellular genome), to promote gene conversion. Exogenous templates can have asymmetric overhangs (i.e. the portion of the template that is complementary to the site of the DSB may be offset in a 3' or 5' direction, rather than being centered within the donor template), for instance as described by Richardson et al. (Nature Biotechnology 34, 339-344 (2016), (Richardson), incorporated by reference). In instances where the template is single-stranded, it can correspond to either the complementary (top) or non-complementary (bottom) strand of the targeted region.

Gene conversion and gene correction are facilitated, in some cases, by the formation of one or more nicks in or around the targeted region, as described in Ran and Cotta-Ramusino. In some cases, a dual-nickase strategy is used to form two offset SSBs that, in turn, form a single DSB having an overhang (e.g. a 5' overhang).

Interruption and/or deletion of all or part of a targeted sequence can be achieved by a variety of repair outcomes. As one example, a sequence can be deleted by simultaneously generating two or more DSBs that flank a targeted region, which is then excised when the DSBs are repaired, as is described in Maeder for the LCA10 mutation. As another example, a sequence can be interrupted by a deletion generated by formation of a double strand break with single-stranded overhangs, followed by exonucleolytic processing of the overhangs prior to repair.

One specific subset of target sequence interruptions is mediated by the formation of an indel within the targeted sequence, where the repair outcome is typically mediated by NHEJ pathways (including Alt-NHEJ). NHEJ is referred to as an "error prone" repair pathway because of its association with indel mutations. In some cases, however, a DSB is repaired by NHEJ without alteration of the sequence around it (a so-called "perfect" or "scarless" repair); this generally requires the two ends of the DSB to be perfectly ligated. Indels, meanwhile, are thought to arise from enzymatic processing of free DNA ends before they are ligated that adds and/or removes nucleotides from either or both strands of either or both free ends.

Because the enzymatic processing of free DSB ends may be stochastic in nature, indel mutations tend to be variable, occurring along a distribution, and can be influenced by a variety of factors, including the specific target site, the cell type used, the genome editing strategy used, etc. It is possible to draw limited generalizations about indel formation: deletions formed by repair of a single DSB are most commonly in the 1-50 bp range, but can reach greater than 100-200 bp. Insertions formed by repair of a single DSB tend to be shorter and often include short duplications of the sequence immediately surrounding the break site. However, it is possible to obtain large insertions, and in these cases, the inserted sequence has often been traced to other regions of the genome or to plasmid DNA present in the cells.

Indel mutations—and genome editing systems configured to produce indels—are useful for interrupting target sequences, for example, when the generation of a specific final sequence is not required and/or where a frameshift mutation would be tolerated. They can also be useful in settings where particular sequences are preferred, insofar as the certain sequences desired tend to occur preferentially from the repair of an SSB or DSB at a given site. Indel mutations are also a useful tool for evaluating or screening the activity of particular genome editing systems and their components. In these and other settings, indels can be characterized by (a) their relative and absolute frequencies in the genomes of cells contacted with genome editing systems and (b) the distribution of numerical differences relative to the unedited sequence, e.g. ±1, ±2, ±3, etc. As one example, in a lead-finding setting, multiple gRNAs can be screened to identify those gRNAs that most efficiently drive cutting at a target site based on an indel readout under controlled conditions. Guides that produce indels at or above a threshold frequency, or that produce a particular distribution of indels, can be selected for further study and development. Indel frequency and distribution can also be useful as a readout for evaluating different genome editing system implementations or formulations and delivery methods, for instance by keeping the gRNA constant and varying certain other reaction conditions or delivery methods.

Multiplex Strategies

While exemplary strategies discussed above have focused on repair outcomes mediated by single DSBs, genome editing systems according to this disclosure may also be employed to generate two or more DSBs, either in the same locus or in different loci. Strategies for editing that involve the formation of multiple DSBs, or SSBs, are described in, for instance, Cotta-Ramusino.

Donor Template Design

Donor template design is described in detail in the literature, for instance in Cotta-Ramusino. DNA oligomer donor templates (oligodeoxynucleotides or ODNs), which can be single-stranded (ssODNs) or double-stranded (dsODNs), can be used to facilitate HDR-based repair of DSBs, and are particularly useful for introducing alterations into a target DNA sequence, inserting a new sequence into the target sequence, or replacing the target sequence altogether.

Whether single-stranded or double-stranded, donor templates generally include regions that are homologous to regions of DNA within or near (e.g. flanking or adjoining) a target sequence to be cleaved. These homologous regions are referred to here as "homology arms," and are illustrated schematically below:

[5' homology arm]—[replacement sequence]—[3' homology arm].

The homology arms can have any suitable length (including 0 nucleotides if only one homology arm is used), and 3' and 5' homology arms can have the same length, or can differ in length. The selection of appropriate homology arm lengths can be influenced by a variety of factors, such as the desire to avoid homologies or microhomologies with certain sequences such as Alu repeats or other very common elements. For example, a 5' homology arm can be shortened to avoid a sequence repeat element. In other embodiments, a 3' homology arm can be shortened to avoid a sequence repeat element. In some embodiments, both the 5' and the 3' homology arms can be shortened to avoid including certain sequence repeat elements. In addition, some homology arm designs can improve the efficiency of editing or increase the frequency of a desired repair outcome. For example, Richardson et al. Nature Biotechnology 34, 339-344 (2016) (Richardson), which is incorporated by reference, found that the relative asymmetry of 3' and 5' homology arms of single-stranded donor templates influenced repair rates and/or outcomes.

Replacement sequences in donor templates have been described elsewhere, including in Cotta-Ramusino et al. A replacement sequence can be any suitable length (including zero nucleotides, where the desired repair outcome is a deletion), and typically includes one, two, three or more sequence modifications relative to the naturally-occurring sequence within a cell in which editing is desired. One common sequence modification involves the alteration of the naturally-occurring sequence to repair a mutation that is related to a disease or condition of which treatment is desired. Another common sequence modification involves the alteration of one or more sequences that are complementary to, or code for, the PAM sequence of the RNA-guided nuclease or the targeting domain of the gRNA(s) being used to generate an SSB or DSB, to reduce or eliminate repeated cleavage of the target site after the replacement sequence has been incorporated into the target site.

Where a linear ssODN is used, it can be configured to (i) anneal to the nicked strand of the target nucleic acid, (ii) anneal to the intact strand of the target nucleic acid, (iii) anneal to the plus strand of the target nucleic acid, and/or (iv) anneal to the minus strand of the target nucleic acid. An ssODN may have any suitable length, e.g., about, or no more than 150-200 nucleotides (e.g., 150, 160, 170, 180, 190, or 200 nucleotides).

It should be noted that a template nucleic acid can also be a nucleic acid vector, such as a viral genome or circular double-stranded DNA, e.g., a plasmid. Nucleic acid vectors comprising donor templates can include other coding or non-coding elements. For example, a template nucleic acid can be delivered as part of a viral genome (e.g. in an AAV or lentiviral genome) that includes certain genomic backbone elements (e.g. inverted terminal repeats, in the case of an AAV genome) and optionally includes additional sequences coding for a gRNA and/or an RNA-guided nuclease. In certain embodiments, the donor template can be adjacent to, or flanked by, target sites recognized by one or more gRNAs, to facilitate the formation of free DSBs on one or both ends of the donor template that can participate in repair of corresponding SSBs or DSBs formed in cellular DNA using the same gRNAs. Exemplary nucleic acid vectors suitable for use as donor templates are described in Cotta-Ramusino.

Whatever format is used, a template nucleic acid can be designed to avoid undesirable sequences. In certain embodiments, one or both homology arms can be shortened to avoid overlap with certain sequence repeat elements, e.g., Alu repeats, LINE elements, etc.

Target Cells

Genome editing systems according to this disclosure can be used to manipulate or alter a cell, e.g., to edit or alter a target nucleic acid. The manipulating can occur, in various embodiments, in vivo or ex vivo.

A variety of cell types can be manipulated or altered according to the embodiments of this disclosure, and in some cases, such as in vivo applications, a plurality of cell types are altered or manipulated, for example by delivering genome editing systems according to this disclosure to a plurality of cell types. In other cases, however, it may be desirable to limit manipulation or alteration to a particular cell type or types. For instance, it can be desirable in some instances to edit a cell with limited differentiation potential or a terminally differentiated cell, such as a photoreceptor cell in the case of Maeder, in which modification of a genotype is expected to result in a change in cell phenotype. In other cases, however, it may be desirable to edit a less differentiated, multipotent or pluripotent, stem or progenitor cell. By way of example, the cell may be an embryonic stem cell, induced pluripotent stem cell (iPSC), hematopoietic stem/progenitor cell (HSPC), or other stem or progenitor cell type that differentiates into a cell type of relevance to a given application or indication.

As a corollary, the cell being altered or manipulated is, variously, a dividing cell or a non-dividing cell, depending on the cell type(s) being targeted and/or the desired editing outcome.

When cells are manipulated or altered ex vivo, the cells can be used (e.g. administered to a subject) immediately, or they can be maintained or stored for later use. Those of skill in the art will appreciate that cells can be maintained in culture or stored (e.g. frozen in liquid nitrogen) using any suitable method known in the art.

Implementation of Genome Editing Systems: Delivery, Formulations, and Routes of Administration As discussed above, the genome editing systems of this disclosure can be implemented in any suitable manner, meaning that the components of such systems, including without limitation the RNA-guided nuclease, gRNA, and optional donor template nucleic acid, can be delivered, formulated, or administered in any suitable form or combination of forms that results in the transduction, expression or introduction of a genome editing system and/or causes a desired repair outcome in a cell, tissue or subject. Tables 6 and 7 set forth several, non-limiting examples of genome editing system implementations. Those of skill in the art will appreciate, however, that these listings are not comprehensive, and that other implementations are possible. With reference to Table 6 in particular, the table lists several exemplary implementations of a genome editing system comprising a single gRNA and an optional donor template. However, genome editing systems according to this disclosure can incorporate multiple gRNAs, multiple RNA-guided nucleases, and other components such as proteins, and a variety of implementations will be evident to the skilled artisan based on the principles illustrated in the table. In the table, [N/A] indicates that the genome editing system does not include the indicated component.

TABLE 6

Genome Editing System Components

| RNA-guided Nuclease | gRNA | Donor Template | Comments |
|---|---|---|---|
| Protein | RNA | [N/A] | An RNA-guided nuclease protein complexed with a gRNA molecule (an RNP complex) |
| Protein | RNA | DNA | An RNP complex as described above plus a single-stranded or double-stranded donor template. |
| Protein | DNA | [N/A] | An RNA-guided nuclease protein plus gRNA transcribed from DNA. |
| Protein | DNA | DNA | An RNA-guided nuclease protein plus gRNA-encoding DNA and a separate DNA donor template. |
| Protein | DNA | | An RNA-guided nuclease protein and a single DNA encoding both a gRNA and a donor template. |
| | DNA | | A DNA or DNA vector encoding an RNA-guided nuclease, a gRNA and a donor template. |
| DNA | DNA | [N/A] | Two separate DNAs, or two separate DNA vectors, encoding the RNA-guided nuclease and the gRNA, respectively. |
| DNA | DNA | DNA | Three separate DNAs, or three separate DNA vectors, encoding the RNA-guided nuclease, the gRNA and the donor template, respectively. |
| DNA | | [N/A] | A DNA or DNA vector encoding an RNA-guided nuclease and a gRNA |
| DNA | | DNA | A first DNA or DNA vector encoding an RNA-guided nuclease and a gRNA, and a second DNA or DNA vector encoding a donor template. |

TABLE 6-continued

Genome Editing System Components

| RNA-guided Nuclease | gRNA | Donor Template | Comments |
|---|---|---|---|
| DNA | DNA | | A first DNA or DNA vector encoding an RNA-guided nuclease and second DNA or DNA vector encoding a gRNA and a donor template. |
| | DNA | DNA | A first DNA or DNA vector encoding an RNA-guided nuclease and a donor template, and a second DNA or DNA vector encoding a gRNA |
| | DNA | RNA | A DNA or DNA vector encoding an RNA-guided nuclease and a donor template, and a gRNA |
| RNA | [N/A] | | An RNA or RNA vector encoding an RNA-guided nuclease and comprising a gRNA |
| RNA | | DNA | An RNA or RNA vector encoding an RNA-guided nuclease and comprising a gRNA, and a DNA or DNA vector encoding a donor template. |

Table 7 summarizes various delivery methods for the components of genome editing systems, as described herein. Again, the listing is intended to be exemplary rather than limiting.

TABLE 7

| Delivery Vector/Mode | | Delivery into Non-Dividing Cells | Duration of Expression | Genome Integration | Type of Molecule Delivered |
|---|---|---|---|---|---|
| Physical (e.g., electroporation, particle gun, Calcium Phosphate transfection, cell compression or squeezing) | | YES | Transient | NO | Nucleic Acids and Proteins |
| Viral | Retrovirus | NO | Stable | YES | RNA |
| | Lentivirus | YES | Stable | YES/NO with modifications | RNA |
| | Adenovirus | YES | Transient | NO | DNA |
| | Adeno-Associated Virus (AAV) | YES | Stable | NO | DNA |
| | Vaccinia Virus | YES | Very Transient | NO | DNA |
| | Herpes Simplex Virus | YES | Stable | NO | DNA |
| Non-Viral | Cationic Liposomes | YES | Transient | Depends on what is delivered | Nucleic Acids and Proteins |
| | Polymeric Nanoparticles | YES | Transient | Depends on what is delivered | Nucleic Acids and Proteins |
| Biological Non-Viral Delivery Vehicles | Attenuated Bacteria | YES | Transient | NO | Nucleic Acids |
| | Engineered Bacteriophages | YES | Transient | NO | Nucleic Acids |
| | Mammalian Virus-like Particles | YES | Transient | NO | Nucleic Acids |
| | Biological liposomes: Erythrocyte Ghosts and Exosomes | YES | Transient | NO | Nucleic Acids |

Nucleic Acid-Based Delivery of Genome Editing Systems

Nucleic acids encoding the various elements of a genome editing system according to the present disclosure can be administered to subjects or delivered into cells by art-known methods or as described herein. For example, RNA-guided nuclease-encoding and/or gRNA-encoding DNA, as well as donor template nucleic acids can be delivered by, e.g., vectors (e.g., viral or non-viral vectors), non-vector based methods (e.g., using naked DNA or DNA complexes), or a combination thereof.

Nucleic acids encoding genome editing systems or components thereof can be delivered directly to cells as naked DNA or RNA, for instance by means of transfection or electroporation, or can be conjugated to molecules (e.g., N-acetylgalactosamine) promoting uptake by the target cells (e.g., erythrocytes, HSCs). Nucleic acid vectors, such as the vectors summarized in Table 7, can also be used.

Nucleic acid vectors can comprise one or more sequences encoding genome editing system components, such as an RNA-guided nuclease, a gRNA and/or a donor template. A vector can also comprise a sequence encoding a signal peptide (e.g., for nuclear localization, nucleolar localization, or mitochondrial localization), associated with (e.g., inserted into or fused to) a sequence coding for a protein. As one example, a nucleic acid vectors can include a Cas9 coding sequence that includes one or more nuclear localization sequences (e.g., a nuclear localization sequence from SV40).

The nucleic acid vector can also include any suitable number of regulatory/control elements, e.g., promoters, enhancers, introns, polyadenylation signals, Kozak consensus sequences, or internal ribosome entry sites (IRES). These elements are well known in the art, and are described in Cotta-Ramusino.

Nucleic acid vectors according to this disclosure include recombinant viral vectors. Exemplary viral vectors are set forth in Table 7, and additional suitable viral vectors and their use and production are described in Cotta-Ramusino. Other viral vectors known in the art can also be used. In addition, viral particles can be used to deliver genome editing system components in nucleic acid and/or peptide form. For example, "empty" viral particles can be assembled to contain any suitable cargo. Viral vectors and viral particles can also be engineered to incorporate targeting ligands to alter target tissue specificity.

In addition to viral vectors, non-viral vectors can be used to deliver nucleic acids encoding genome editing systems according to the present disclosure. One important category of non-viral nucleic acid vectors are nanoparticles, which can be organic or inorganic. Nanoparticles are well known in the art, and are summarized in Cotta-Ramusino. Any suitable nanoparticle design can be used to deliver genome editing system components or nucleic acids encoding such components. For instance, organic (e.g. lipid and/or polymer) nanoparticles can be suitable for use as delivery vehicles in certain embodiments of this disclosure. Exemplary lipids for use in nanoparticle formulations, and/or gene transfer are shown in Table 8, and Table 9 lists exemplary polymers for use in gene transfer and/or nanoparticle formulations.

TABLE 8

Lipids Used for Gene Transfer

| Lipid | Abbreviation | Feature |
|---|---|---|
| 1,2-Dioleoyl-sn-glycero-3-phosphatidylcholine | DOPC | Helper |
| 1,2-Dioleoyl-sn-glycero-3-phosphatidylethanolamine | DOPE | Helper |
| Cholesterol | | Helper |
| N-[1-(2,3-Dioleyloxy)propyl]N,N,N-trimethylammonium chloride | DOTMA | Cationic |
| 1,2-Dioleoyloxy-3-trimethylammonium-propane | DOTAP | Cationic |
| Dioctadecylamidoglycylspermine | DOGS | Cationic |
| N-(3-Aminopropyl)-N,N-dimethyl-2,3-bis(dodecyloxy)-1-propanaminium bromide | GAP-DLRIE | Cationic |
| Cetyltrimethylammonium bromide | CTAB | Cationic |
| 6-Lauroxyhexyl ornithinate | LHON | Cationic |
| 1-(2,3-Dioleoyloxypropyl)-2,4,6-trimethylpyridinium | 2Oc | Cationic |
| 2,3-Dioleyloxy-N-[2(sperminecarboxamido-ethyl]-N,N-dimethyl-1-propanaminium trifluoroacetate | DOSPA | Cationic |
| 1,2-Dioleyl-3-trimethylammonium-propane | DOPA | Cationic |
| N-(2-Hydroxyethyl)-N,N-dimethyl-2,3-bis(tetradecyloxy)-1-propanaminium bromide | MDRIE | Cationic |
| Dimyristooxypropyl dimethyl hydroxyethyl ammonium bromide | DMRI | Cationic |
| 3β-[N-(N′,N′-Dimethylaminoethane)-carbamoyl]cholesterol | DC-Chol | Cationic |
| Bis-guanidium-tren-cholesterol | BGTC | Cationic |
| 1,3-Diodeoxy-2-(6-carboxy-spermyl)-propylamide | DOSPER | Cationic |
| Dimethyloctadecylammonium bromide | DDAB | Cationic |
| Dioctadecylamidoglicylspermidin | DSL | Cationic |
| rac-[(2,3-Dioctadecyloxypropyl)(2-hydroxyethyl)]-dimethylammonium chloride | CLIP-1 | Cationic |
| rac-[2(2,3-Dihexadecyloxypropyl-oxymethyloxy)ethyl]trimethylammonium bromide | CLIP-6 | Cationic |
| Ethyldimyristoylphosphatidylcholine | EDMPC | Cationic |
| 1,2-Distearyloxy-N,N-dimethyl-3-aminopropane | DSDMA | Cationic |
| 1,2-Dimyristoyl-trimethylammonium propane | DMTAP | Cationic |
| O,O′-Dimyristyl-N-lysyl aspartate | DMKE | Cationic |
| 1,2-Distearoyl-sn-glycero-3-ethyl-phosphocholine | DSEPC | Cationic |
| N-Palmitoyl D-erythro-sphingosyl carbamoyl-spermine | CCS | Cationic |
| N-t-Butyl-N0-tetradecyl-3-tetradecylaminopropionamidine | diC14-amidine | Cationic |
| Octadecenolyoxy[ethyl-2-heptadecenyl-3 hydroxyethyl]imidazolinium chloride | DOTIM | Cationic |
| N1-Cholesteryloxycarbonyl-3,7-diazanonane-1,9-diamine | CDAN | Cationic |
| 2-(3-[Bis(3-amino-propyl)-amino]propylamino)-N-ditetradecylcarbamoylme-ethyl-acetamide | RPR209120 | Cationic |
| 1,2-dilinoleyloxy-3-dimethylaminopropane | DLinDMA | Cationic |
| 2,2-dilinoleyl-4-dimethylaminoethyl-[1,3]-dioxolane | DLin-KC2-DMA | Cationic |
| dilinoleyl-methyl-4-dimethylaminobutyrate | DLin-MC3-DMA | Cationic |

TABLE 9

Polymers Used for Gene Transfer

| Polymer | Abbreviation |
|---|---|
| Poly(ethylene)glycol | PEG |
| Polyethylenimine | PEI |
| Dithiobis(succinimidylpropionate) | DSP |
| Dimethyl-3,3′-dithiobispropionimidate | DTBP |
| Poly(ethylene imine) biscarbamate | PEIC |
| Poly(L-lysine) | PLL |
| Histidine modified PLL | |
| Poly(N-vinylpyrrolidone) | PVP |
| Poly(propylenimine) | PPI |
| Poly(amidoamine) | PAMAM |
| Poly(amido ethylenimine) | SS-PAEI |
| Triethylenetetramine | TETA |
| Poly(β-aminoester) | |
| Poly(4-hydroxy-L-proline ester) | PHP |
| Poly(allylamine) | |
| Poly(α-[4-aminobutyl]-L-glycolic acid) | PAGA |
| Poly(D,L-lactic-co-glycolic acid) | PLGA |
| Poly(N-ethyl-4-vinylpyridinium bromide) | |
| Poly(phosphazene)s | PPZ |
| Poly(phosphoester)s | PPE |
| Poly(phosphoramidate)s | PPA |
| Poly(N-2-hydroxypropylmethacrylamide) | pHPMA |
| Poly (2-(dimethylamino)ethyl methacrylate) | pDMAEMA |
| Poly(2-aminoethyl propylene phosphate) | PPE-EA |
| Chitosan | |
| Galactosylated chitosan | |
| N-Dodacylated chitosan | |
| Histone | |
| Collagen | |
| Dextran-spermine | D-SPM |

Non-viral vectors optionally include targeting modifications to improve uptake and/or selectively target certain cell types. These targeting modifications can include e.g., cell specific antigens, monoclonal antibodies, single chain antibodies, aptamers, polymers, sugars (e.g., N-acetylgalactosamine (GalNAc)), and cell penetrating peptides. Such vectors also optionally use fusogenic and endosome-destabilizing peptides/polymers, undergo acid-triggered conformational changes (e.g., to accelerate endosomal escape of the cargo), and/or incorporate a stimuli-cleavable polymer, e.g., for release in a cellular compartment. For example, disulfide-based cationic polymers that are cleaved in the reducing cellular environment can be used.

In certain embodiments, one or more nucleic acid molecules (e.g., DNA molecules) other than the components of a genome editing system, e.g., the RNA-guided nuclease component and/or the gRNA component described herein, are delivered. In certain embodiments, the nucleic acid molecule is delivered at the same time as one or more of the components of the genome editing system. In certain embodiments, the nucleic acid molecule is delivered before or after (e.g., less than about 30 minutes, 1 hour, 2 hours, 3 hours, 6 hours, 9 hours, 12 hours, 1 day, 2 days, 3 days, 1 week, 2 weeks, or 4 weeks) one or more of the components of the genome editing system are delivered. In certain embodiments, the nucleic acid molecule is delivered by a different means than one or more of the components of the genome editing system, e.g., the RNA-guided nuclease component and/or the gRNA component, are delivered. The nucleic acid molecule can be delivered by any of the delivery methods described herein. For example, the nucleic acid molecule can be delivered by a viral vector, e.g., an integration-deficient lentivirus, and the RNA-guided nuclease molecule component and/or the gRNA component can be delivered by electroporation, e.g., such that the toxicity caused by nucleic acids (e.g., DNAs) can be reduced. In certain embodiments, the nucleic acid molecule encodes a therapeutic protein, e.g., a protein described herein. In certain embodiments, the nucleic acid molecule encodes an RNA molecule, e.g., an RNA molecule described herein.

Delivery of RNPs and/or RNA Encoding Genome Editing System Components

RNPs (complexes of gRNAs and RNA-guided nucleases, i.e., ribonucleoprotein complexes) and/or RNAs encoding RNA-guided nucleases and/or gRNAs, can be delivered into cells or administered to subjects by art-known methods, some of which are described in Cotta-Ramusino. In vitro, RNA-guided nuclease-encoding and/or gRNA-encoding RNA can be delivered, e.g., by microinjection, electroporation, transient cell compression or squeezing (see, e.g., Lee 2012). Lipid-mediated transfection, peptide-mediated delivery, GalNAc- or other conjugate-mediated delivery, and combinations thereof, can also be used for delivery in vitro and in vivo.

In vitro, delivery via electroporation comprises mixing the cells with the RNA encoding RNA-guided nucleases and/or gRNAs, with or without donor template nucleic acid molecules, in a cartridge, chamber or cuvette and applying one or more electrical impulses of defined duration and amplitude. Systems and protocols for electroporation are known in the art, and any suitable electroporation tool and/or protocol can be used in connection with the various embodiments of this disclosure.

Route of Administration

Genome editing systems, or cells altered or manipulated using such systems, can be administered to subjects by any suitable mode or route, whether local or systemic. Systemic modes of administration include oral and parenteral routes. Parenteral routes include, by way of example, intravenous, intramarrow, intrarterial, intramuscular, intradermal, subcutaneous, intranasal, and intraperitoneal routes. Components administered systemically can be modified or formulated to target, e.g., HSCs, hematopoietic stem/progenitor cells, or erythroid progenitors or precursor cells.

Local modes of administration include, by way of example, intramarrow injection into the trabecular bone or intrafemoral injection into the marrow space, and infusion into the portal vein. In certain embodiments, significantly smaller amounts of the components (compared with systemic approaches) can exert an effect when administered locally (for example, directly into the bone marrow) compared to when administered systemically (for example, intravenously). Local modes of administration can reduce or eliminate the incidence of potentially toxic side effects that may occur when therapeutically effective amounts of a component are administered systemically.

Administration can be provided as a periodic bolus (for example, intravenously) or as continuous infusion from an internal reservoir or from an external reservoir (for example, from an intravenous bag or implantable pump). Components can be administered locally, for example, by continuous release from a sustained release drug delivery device.

In addition, components can be formulated to permit release over a prolonged period of time. A release system can include a matrix of a biodegradable material or a material which releases the incorporated components by diffusion. The components can be homogeneously or heterogeneously distributed within the release system. A variety of release systems can be useful, however, the choice of the appropriate system will depend upon rate of release required by a particular application. Both non-degradable and degradable release systems can be used. Suitable release systems include polymers and polymeric matrices, non-polymeric matrices, or inorganic and organic excipients and diluents such as, but not limited to, calcium carbonate and sugar (for example, trehalose). Release systems may be natural or synthetic. However, synthetic release systems are preferred because generally they are more reliable, more reproducible and produce more defined release profiles. The release system material can be selected so that components having different molecular weights are released by diffusion through or degradation of the material.

Representative synthetic, biodegradable polymers include, for example: polyamides such as poly(amino acids) and poly(peptides); polyesters such as poly(lactic acid), poly(glycolic acid), poly(lactic-co-glycolic acid), and poly (caprolactone); poly(anhydrides); polyorthoesters; polycarbonates; and chemical derivatives thereof (substitutions, additions of chemical groups, for example, alkyl, alkylene, hydroxylations, oxidations, and other modifications routinely made by those skilled in the art), copolymers and mixtures thereof. Representative synthetic, non-degradable polymers include, for example: polyethers such as poly (ethylene oxide), poly(ethylene glycol), and poly(tetramethylene oxide); vinyl polymers-polyacrylates and polymethacrylates such as methyl, ethyl, other alkyl, hydroxyethyl methacrylate, acrylic and methacrylic acids, and others such as poly(vinyl alcohol), poly(vinyl pyrolidone), and poly (vinyl acetate); poly(urethanes); cellulose and its derivatives such as alkyl, hydroxyalkyl, ethers, esters, nitrocellulose, and various cellulose acetates; polysiloxanes; and any chemical derivatives thereof (substitutions, additions of chemical groups, for example, alkyl, alkylene, hydroxylations, oxidations, and other modifications routinely made by those skilled in the art), copolymers and mixtures thereof.

Poly(lactide-co-glycolide) microsphere can also be used. Typically the microspheres are composed of a polymer of lactic acid and glycolic acid, which are structured to form hollow spheres. The spheres can be approximately 15-30 microns in diameter and can be loaded with components described herein.

Multi-Modal or Differential Delivery of Components

Skilled artisans will appreciate, in view of the instant disclosure, that different components of genome editing systems disclosed herein can be delivered together or separately and simultaneously or nonsimultaneously. Separate and/or asynchronous delivery of genome editing system components can be particularly desirable to provide temporal or spatial control over the function of genome editing systems and to limit certain effects caused by their activity.

Different or differential modes as used herein refer to modes of delivery that confer different pharmacodynamic or pharmacokinetic properties on the subject component molecule, e.g., a RNA-guided nuclease molecule, gRNA, template nucleic acid, or payload. For example, the modes of delivery can result in different tissue distribution, different half-life, or different temporal distribution, e.g., in a selected compartment, tissue, or organ.

Some modes of delivery, e.g., delivery by a nucleic acid vector that persists in a cell, or in progeny of a cell, e.g., by autonomous replication or insertion into cellular nucleic acid, result in more persistent expression of and presence of a component. Examples include viral, e.g., AAV or lentivirus, delivery.

By way of example, the components of a genome editing system, e.g., a RNA-guided nuclease and a gRNA, can be delivered by modes that differ in terms of resulting half-life or persistent of the delivered component the body, or in a particular compartment, tissue or organ. In certain embodiments, a gRNA can be delivered by such modes. The RNA-guided nuclease molecule component can be delivered by a mode which results in less persistence or less exposure to the body or a particular compartment or tissue or organ.

More generally, in certain embodiments, a first mode of delivery is used to deliver a first component and a second mode of delivery is used to deliver a second component. The first mode of delivery confers a first pharmacodynamic or pharmacokinetic property. The first pharmacodynamic property can be, e.g., distribution, persistence, or exposure, of the component, or of a nucleic acid that encodes the component, in the body, a compartment, tissue or organ. The second mode of delivery confers a second pharmacodynamic or pharmacokinetic property. The second pharmacodynamic property can be, e.g., distribution, persistence, or exposure, of the component, or of a nucleic acid that encodes the component, in the body, a compartment, tissue or organ.

In certain embodiments, the first pharmacodynamic or pharmacokinetic property, e.g., distribution, persistence or exposure, is more limited than the second pharmacodynamic or pharmacokinetic property.

In certain embodiments, the first mode of delivery is selected to optimize, e.g., minimize, a pharmacodynamic or pharmacokinetic property, e.g., distribution, persistence or exposure.

In certain embodiments, the second mode of delivery is selected to optimize, e.g., maximize, a pharmacodynamic or pharmacokinetic property, e.g., distribution, persistence or exposure.

In certain embodiments, the first mode of delivery comprises the use of a relatively persistent element, e.g., a nucleic acid, e.g., a plasmid or viral vector, e.g., an AAV or lentivirus. As such vectors are relatively persistent product transcribed from them would be relatively persistent.

In certain embodiments, the second mode of delivery comprises a relatively transient element, e.g., an RNA or protein.

In certain embodiments, the first component comprises gRNA, and the delivery mode is relatively persistent, e.g., the gRNA is transcribed from a plasmid or viral vector, e.g., an AAV or lentivirus. Transcription of these genes would be of little physiological consequence because the genes do not encode for a protein product, and the gRNAs are incapable of acting in isolation. The second component, a RNA-guided nuclease molecule, is delivered in a transient manner, for example as mRNA or as protein, ensuring that the full RNA-guided nuclease molecule/gRNA complex is only present and active for a short period of time.

Furthermore, the components can be delivered in different molecular form or with different delivery vectors that complement one another to enhance safety and tissue specificity.

Use of differential delivery modes can enhance performance, safety, and/or efficacy, e.g., the likelihood of an eventual off-target modification can be reduced. Delivery of immunogenic components, e.g., Cas9 molecules, by less persistent modes can reduce immunogenicity, as peptides from the bacterially-derived Cas enzyme are displayed on the surface of the cell by MHC molecules. A two-part delivery system can alleviate these drawbacks.

Differential delivery modes can be used to deliver components to different, but overlapping target regions. The formation active complex is minimized outside the overlap of the target regions. Thus, in certain embodiments, a first component, e.g., a gRNA is delivered by a first delivery mode that results in a first spatial, e.g., tissue, distribution. A second component, e.g., a RNA-guided nuclease molecule is delivered by a second delivery mode that results in a second spatial, e.g., tissue, distribution. In certain embodiments, the first mode comprises a first element selected from a liposome, nanoparticle, e.g., polymeric nanoparticle, and a nucleic acid, e.g., viral vector. The second mode comprises a second element selected from the group. In certain embodiments, the first mode of delivery comprises a first targeting element, e.g., a cell specific receptor or an antibody, and the second mode of delivery does not include that element. In certain embodiments, the second mode of delivery comprises a second targeting element, e.g., a second cell specific receptor or second antibody.

When the RNA-guided nuclease molecule is delivered in a virus delivery vector, a liposome, or polymeric nanoparticle, there is the potential for delivery to and therapeutic activity in multiple tissues, when it may be desirable to only target a single tissue. A two-part delivery system can resolve this challenge and enhance tissue specificity. If the gRNA and the RNA-guided nuclease molecule are packaged in separated delivery vehicles with distinct but overlapping tissue tropism, the fully functional complex is only be formed in the tissue that is targeted by both vectors.

EXAMPLES

The following Examples are merely illustrative and are not intended to limit the scope or content of the invention in any way.

Example 1—Self-Inactivating Design Embeds Target Sites in Vector

An AAV vector system is engineered such that it contains self-inactivating, universally applicable, tunable modules. These modules include the already-targeted endogenous cellular sequence, obviating the need for any additional gRNAs. In addition, these modules can be tuned based on positions within the viral genome, choice of gRNA, or PAM sequence.

The self-inactivating design contains DNA sequences that are identical or nearly identical to that of the endogenous target locus. FIG. 1A is a diagram illustrating a SaCas9 (*S. aureus* Cas9)-gRNA complex targets both an endogenous cellular target and a nucleic acid encoding the SaCas9 in a viral vector.

Target sequences in the AAV are variably positioned, at either a site in the viral backbone or one of four regions in the SaCas9 coding sequences, and contain either canonical or suboptimal PAMs. FIG. 1B is a cartoon diagram depicting a 2-vector system in which engineered SaCas9 and gRNAS are encoded on separate viral genomes. Three types of exemplary sites in an AAV genome into which heterologous cellular sequences can be engineered are marked by arrows. In type (a), the cellular sequence is inserted at a site in the AAV backbone; in type (b), the cellular sequence is inserted at one of four regions (AC1, AC2, AC3, or N-terminal (NT)) in the SaCas9 coding sequence. In certain AAV vectors, the cellular sequences can be inserted at both type (a) and type (b) sites. SaCas9 and gRNAs can also be engineered into a single-vector system.

Example 2—Target Sites in SaCas9 do not Disrupt SaCas9 Nuclease Activity

Figure 4A:
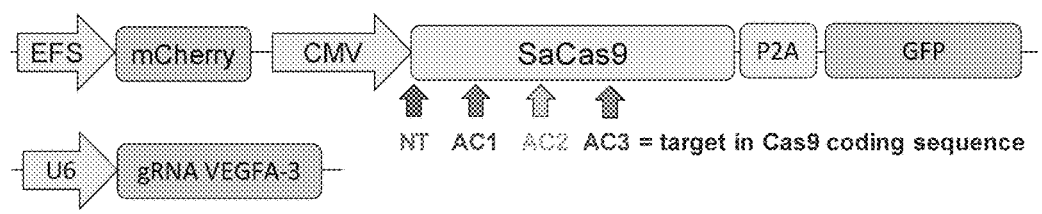
FIG. 4A is a cartoon diagram depicting exemplary constructs with target sites at four different positions in the SaCas9 coding sequence, as well as a gRNA expression plasmid.

This example provides systems and methods of engineering of targets sites in SaCas9 coding sequences that do not disrupt SaCas9 nuclease activity. Various plasmids were constructed, with different target sites at four different positions (NT, AC1, AC2, or AC3) in the SaCas9 coding sequence. FIG. 4A is a cartoon diagram depicting exemplary constructs with target sites at the four different positions in the SaCas9 coding sequence, as well as a human VEGFA-3 gRNA expression plasmid. The target sites were from mCEP290 (guides 7, 9), hCEP290 (guides 64, 323, KKH) and SERPINA1 (guides 333 and 776).

Figure 4B:
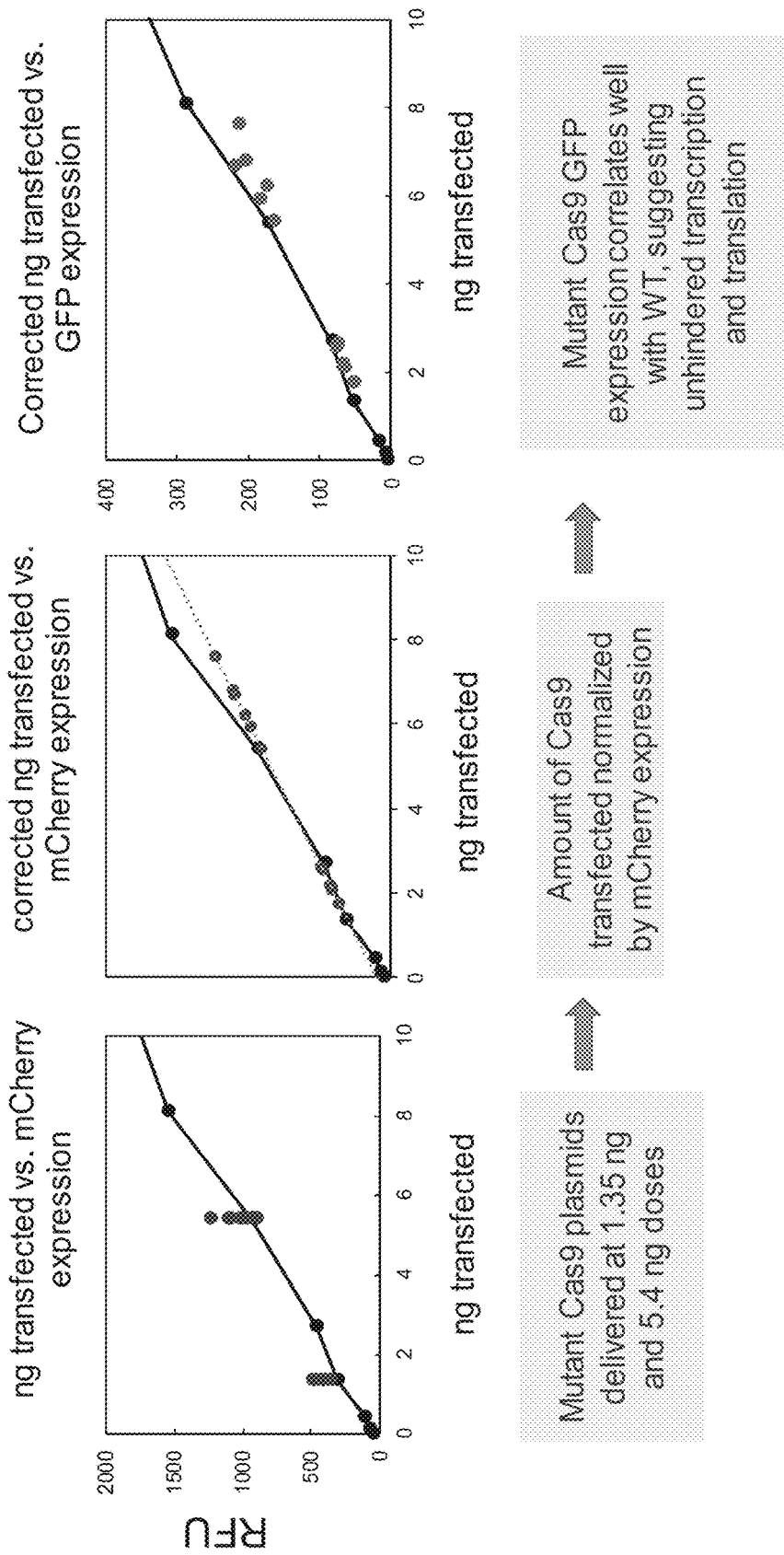
FIG. 4B depicts comparisons of transcription levels and translation levels of wild-type Cas9 constructs and self-inactivating Cas9 constructs.

Self-inactivating or control Cas9 plasmids were transfected into HEK293 cells along with the gRNA expression plasmid targeting VEFGA site 3. mCherry was expressed through a separate promoter and was used to normalize the transfected amount of plasmid. GFP was expressed from the same transcript as SaCas9 and was used to measure the potential differences between transcription and translation rates. FIG. 4B shows that self-inactivating SaCas9 mutants exhibited similar expression level compared to control SaCas9 (WT) in HEK293 cells. GFP expression in self-inactivating SaCas9 constructs correlated with that of control SaCas9 constructs (WT), indicating unhindered transcription and translation of the self-inactivating SaCas9.

Figure 4C:
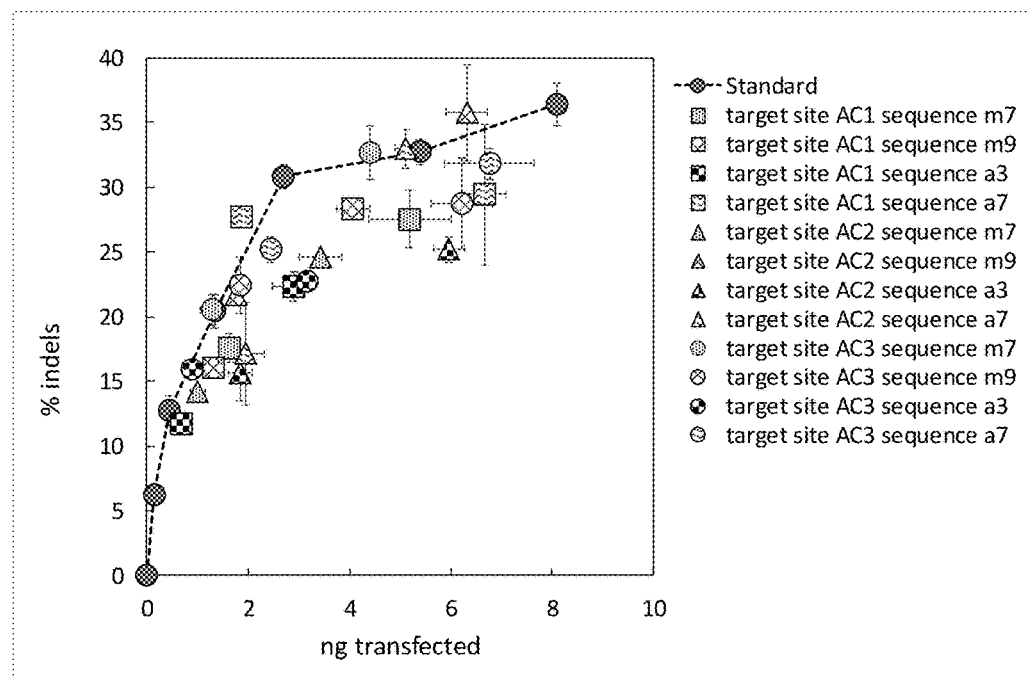
FIGS. 4C-4E depict the levels of nuclease activity among wild-type and self-inactivating SaCas9 proteins.
Figure 4D:
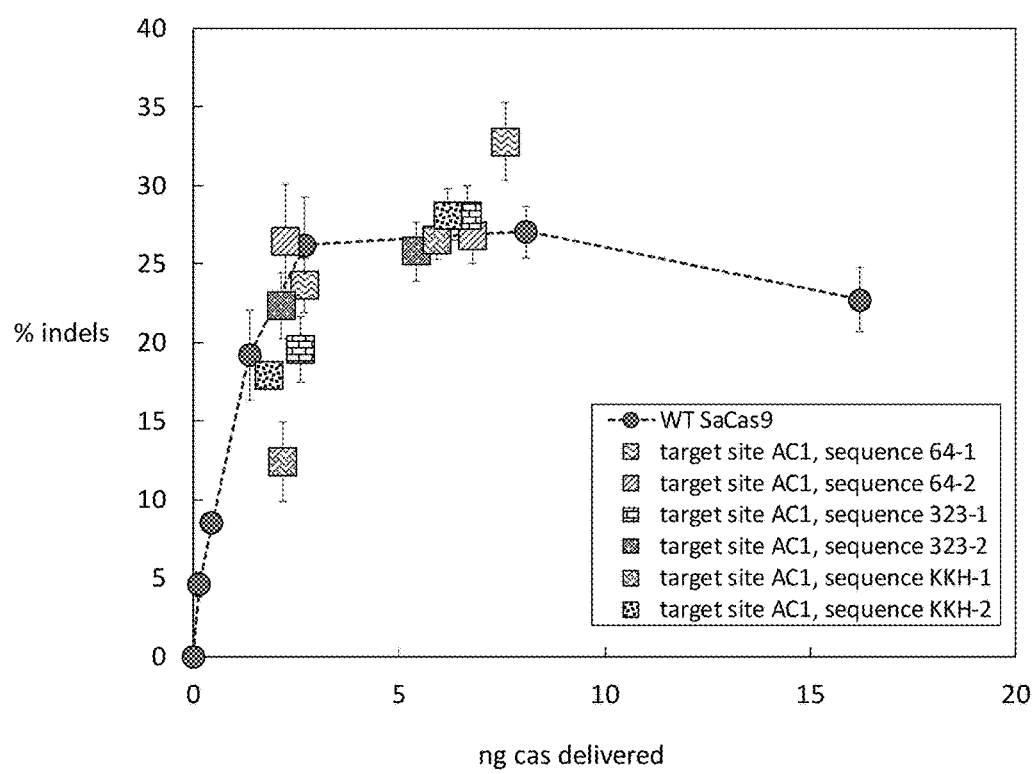
Figure 4E:
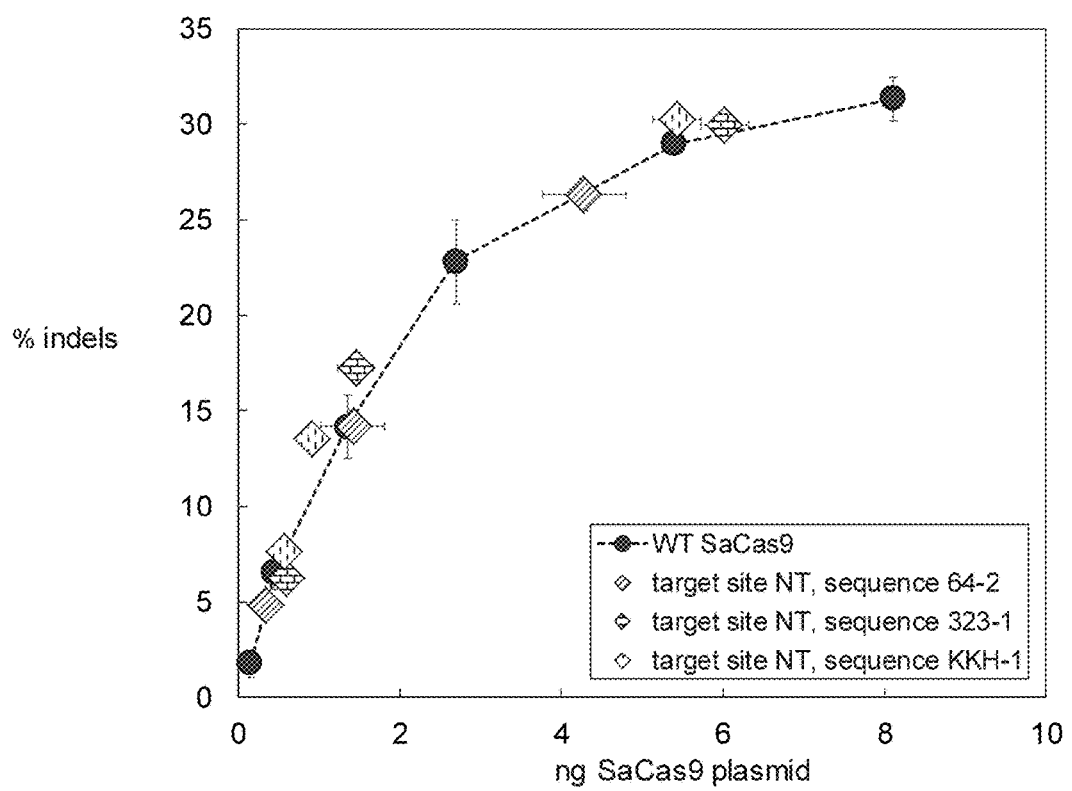

Wild-type control and engineered self-inactivating SaCas9 proteins exhibited similar levels of nuclease activity as shown in FIGS. 4C-4E. Self-inactivating SaCas9 constructs having specific target sequences inserted at specific target sites are indicated in each figure. Target sites AC1, AC2, AC3, and NT are in the coding sequence as depicted in FIGS. 1B and 2. Target sequences m7, m9, a3, a7, 64-1, 64-2, 323-1, 323-2, KKH-1, and KKH-2 refer to sequences in genes mouse CEP290 (guides m7 and m9), human A1ATSERPINA1 (guides a3 and a7), and human CEP290 (guides 64-1, 64-2, 323-1, 323-2, KKH-1, and KKH-2), which are shown in Table 10 below. Control (labeled as "Standard") and self-inactivating SaCas9 nuclease activity was measured by a T7E1 assay. The x-axis shows the amount of plasmid transfected into HEK293 cells, and the y-axis shows the % indels in VEGFA-3 as determined by the T7E1 assay.

TABLE 10

| Target name | Target sequence |
|---|---|
| m7 | AAGCTGCGTGAGACATGTGTTT [SEQ ID NO: 15] |
| m9 | AGCTATCTGTAGCATGCTGA [SEQ ID NO: 16] |
| a3 | AAGGCTGTAGCGATGCTCACTG [SEQ ID NO: 17] |
| a7 | GTGTGCCAGCTGGCGGTATAGG [SEQ ID NO: 18] |
| 64-1 and 64-2 | GTCAAAAGCTACCGGTTACCTG [SEQ ID NO: 19] |
| 323-1 and 323-2 | GTTCTGTCCTCAGTAAAAGGTA [SEQ ID NO: 20] |
| KKH-1 and KKH-2 | CAATAGGGATAGGTATGAGATACT [SEQ ID NO: 21] |

Example 3—Self-Inactivating AAVs Maintain Efficacy at Target GFP Plasmids while Self-Inactivating in HEK293 Cells This example provides in vitro data demonstrating the feasibility of attaining both robust target modification and self-targeting the pool of AAV DNA at its source.

Figure 5A:
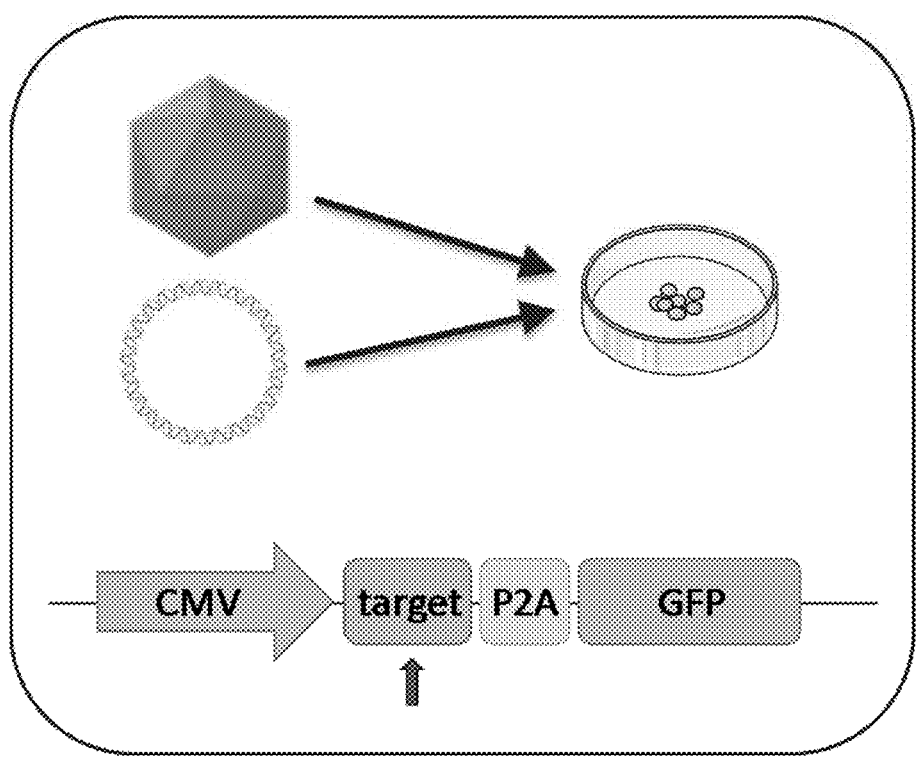
FIG. 5A depicts the experimental design in Example 3.
Figure 5B:
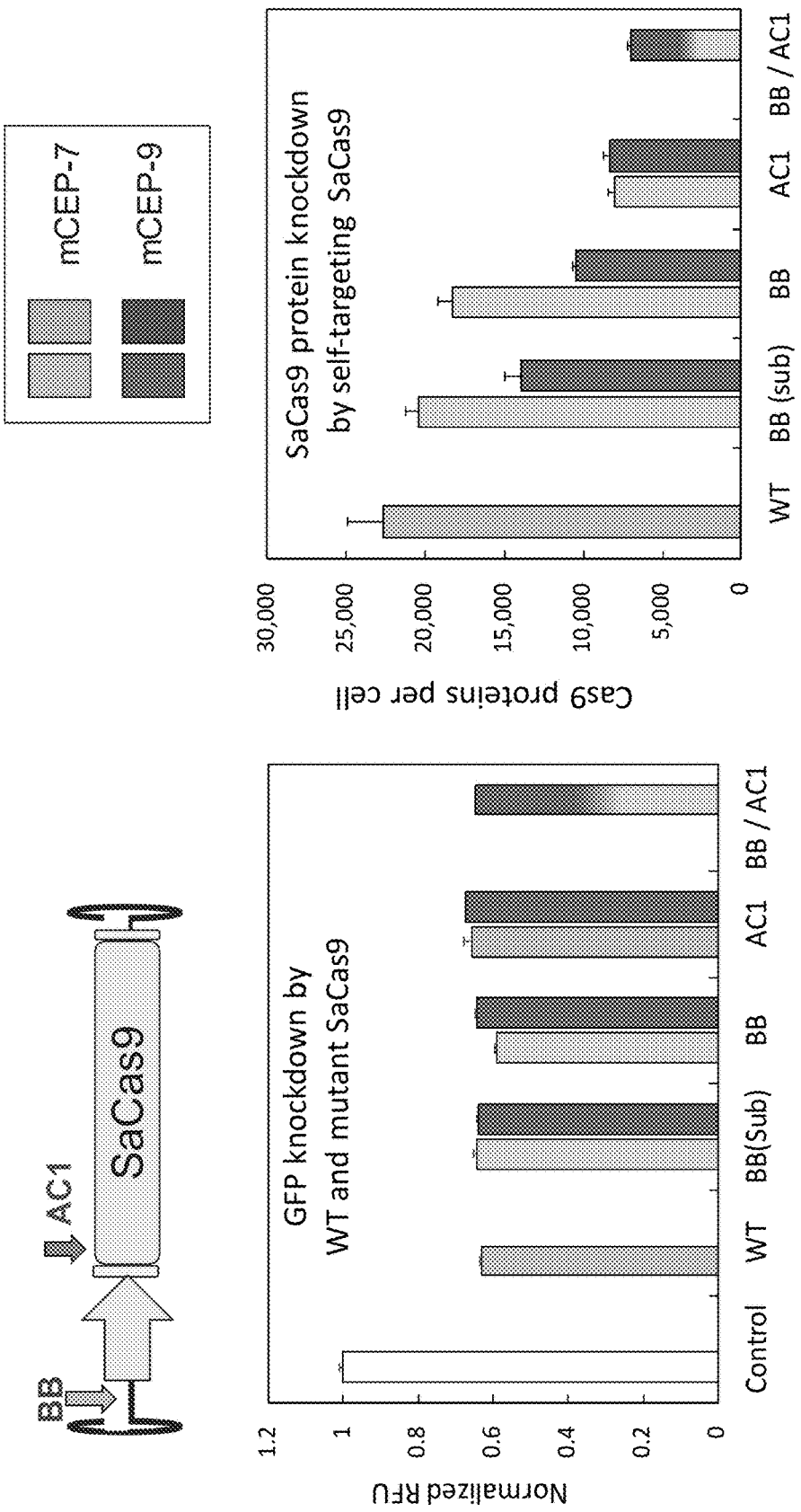
FIG. 5B depicts self-inactivating AAVs maintain efficacy at target GFP plasmids while self-inactivating in HEK293 cells. The upper left panel shows the locations of target sites inserted in the self-inactivating Cas9 constructs. The lower left panel shows GFP expression levels in HEK293 cells with or without wild-type or self-inactivating SaCas9 constructs. The lower right panel shows Cas9 protein levels in HEK293 cells transduced with wild-type or self-inactivating SaCas9 constructs.

HEK293 cells were seeded in 24-well plates and transfected with 500 ng/well of GFP expression plasmids containing gRNA target sites embedded in the 5' end of the GFP coding sequences. The HEK293 cells were transduced the next day with a mixture of gRNA AAV targeting GFP, and either wild-type or self-targeting SaCas9 AAV (as shown in FIG. 1B) at a total dose of 200,000 vg/cell. Two days later, cells were analyzed by fluorescence-activated cell sorting (FACS) to determine knockdown of GFP expression. A schematic of the experimental design is shown in FIG. 5A. FIG. 5B shows GFP expression levels in HEK293 cells with or without wild-type or engineered SaCas9 proteins. Control: no SaCas9 protein; WT: wild-type SaCas9 protein; BB (sub): engineered SaCas9 with target site inserted in the AAV backbone with suboptimal PAM sequence NNGRRA or NNGRRV; BB: engineered SaCas9 with target site inserted in the AAV backbone with canonical PAM sequence; AC1: engineered SaCas9 with target site inserted at the AC1 site of the SaCas9 coding sequence; BB/AC1: engineered SaCas9 with target site inserted both in the AAV backbone and at the AC1 site of the SaCas9 coding sequence. Two different gRNA constructs (mCEP-7 and mCEP-9) were tested individually with self-inactivating SaCas9 proteins. As shown in FIG. 5B, lower left panel, the control SaCas9 construct (WT) and the self-inactivating SaCas9 constructs exhibited similar capacities in knocking down GFP expression.

Protein was also harvested and SaCas9 level was quantified by an alphaLISA assay. FIG. 5B, lower right panel shows Cas9 protein levels in HEK293 cells transduced with wild-type or self-inactivating SaCas9 constructs. All cells transduced with self-inactivating SaCas9 constructs exhibited reduced levels of SaCas9 protein, Engineered SaCas9 constructs with target site inserted at the AC1 site of SaCas9 coding sequence exhibited improved efficacy of self-inactivation compared to SaCas9 constructs with target site inserted in the AAV backbone alone. In addition, gRNA mCEP-9 exhibited stronger self-inactivating capacity than gRNA mCEP-7.

Example 4—Self-Inactivating AAVs Maintain Efficacy at Target Locus while Self-Inactivating in Retinal Explants This example provides tissue explant data demonstrating the feasibility of attaining both robust target modification and self-targeting the pool of AAV DNA at its source.

Figure 6A:
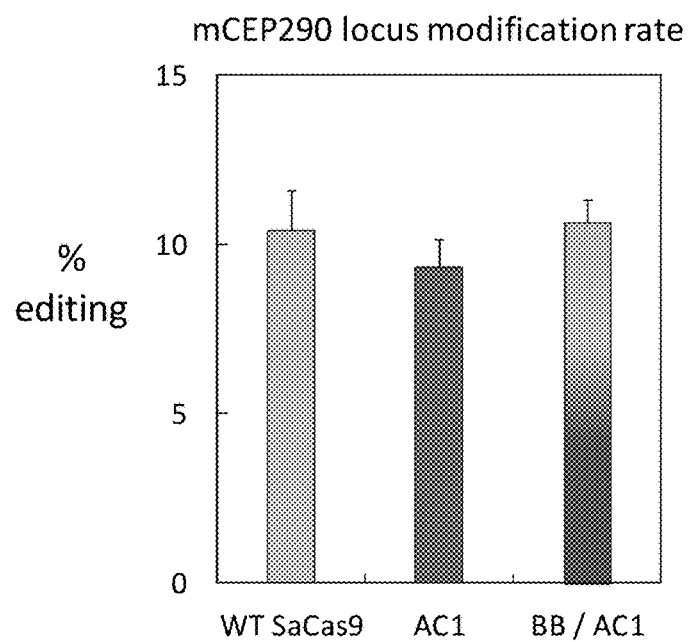
FIG. 6A is a graph showing the editing levels of an endogenous target locus (mCEP290) with wild-type or self-inactivating SaCas9 constructs in mouse retinal explants.

Retinal explants were extracted from BL6 mice and cultured in 24-well plates. The explants were transduced with a mixture of gRNA AAV and either wild-type or self-targeting SaCas9 AAV (as shown in FIG. 1B) at a total dose of 1E11 vg/retina. At day 14 post extraction, both DNA and RNA were harvested from the explants. The endogenous target locus (mCEP290) was amplified from extracted DNA by PCR, cloned into TOPO vector, and sequenced. Control (WT) or self-inactivating SaCas9 constructs exhibited similar gene editing rate at the endogenous target locus in mouse retinal explants as shown in FIG. 6A.

Figure 6B:
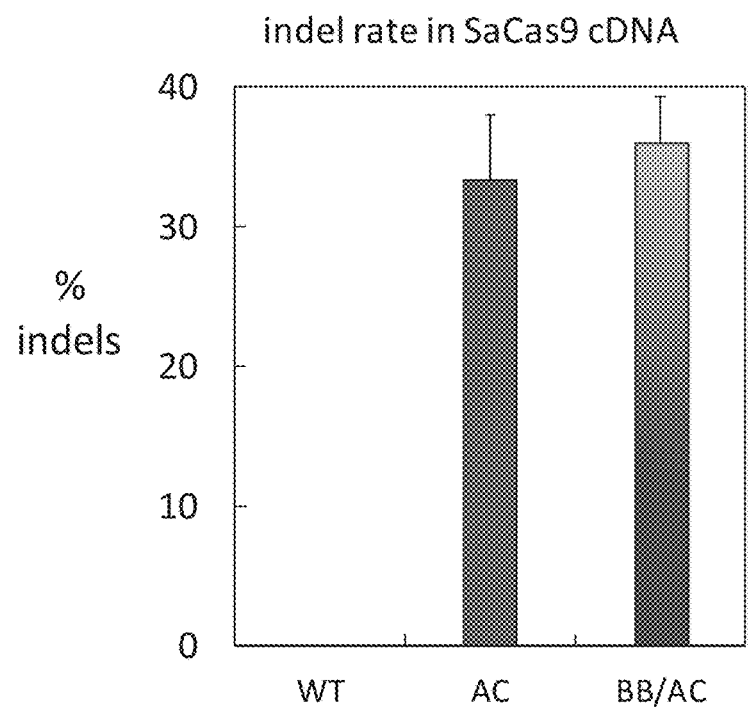
FIG. 6B is a graph demonstrating the % wild-type SaCas9 sequence levels in mouse retinal explants with wild-type or self-inactivating SaCas9 constructs.

In addition, cDNA was generated from the extracted RNA. SaCas9 sequence was amplified by PCR, cloned into TOPO vector, and sequenced. The % indel rates in SaCas9 cDNA are shown in FIG. 6B.

Example 5—Self-Inactivating AAVs Successfully Modified Target Loci while Self-Inactivating In Vivo This example provides in vivo data demonstrating the feasibility of attaining both efficient target modification and self-targeting the pool of AAV DNA at its source. AAVs with SaCas9 and gRNAs targeting mCEP290 were injected subretinally into C57BL/6J mice, and retinas were harvested 6 weeks later for DNA and cDNA sequencing.

Figure 7A:
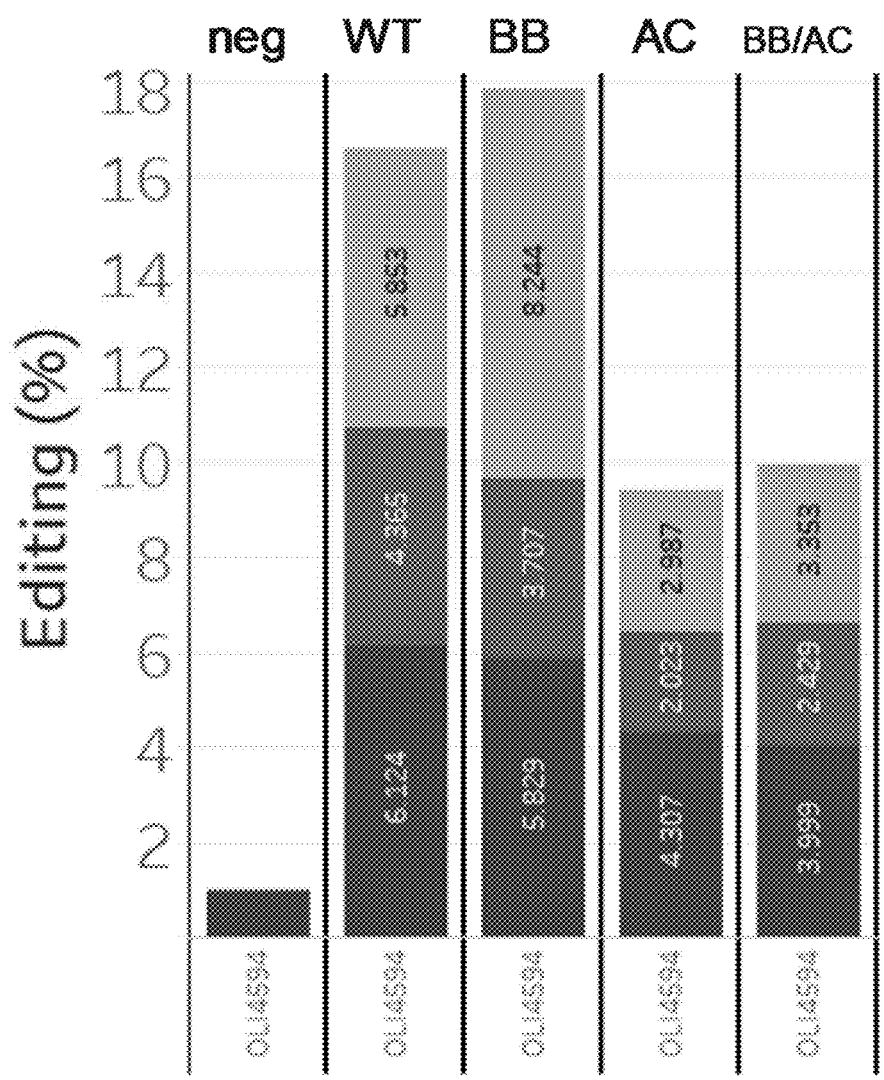
FIG. 7A depicts the editing levels of an endogenous target locus with wild-type or self-inactivating SaCas9 constructs in vivo.

A mixture of gRNA AAV and either wild-type control or self-targeting SaCas9 AAV (as shown in FIG. 1B) at a total dose of $1.16 \times 10^{10}$ AAV per eye were transduced. At 6 weeks post transduction, both DNA and RNA were harvested from the animal tissue. The endogenous target locus was amplified from extracted DNA by PCR and sequenced with Next Generation Sequencing methods on a Miseq machine. Self-inactivating SaCas9 constructs exhibited efficient gene editing rates compared to the negative control as shown in FIG. 7A, though the gene editing rates of SaCas9 constructs having targeting sites within Cas9 coding sequence (AC and BB/AC) were relatively lower compared to the wild-type control.

Figure 7B:
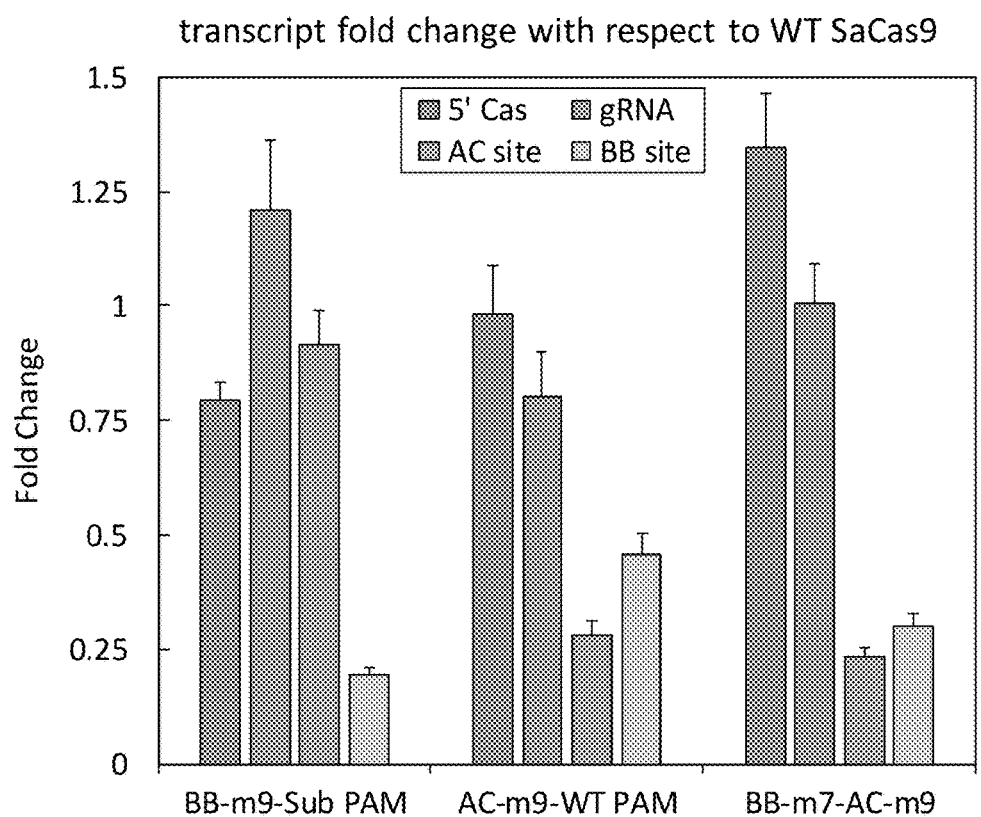
FIG. 7B depicts the fold changes of specific transcripts expressed through self-inactivating SaCas9 constructs compared to the wild-type SaCas9 construct.

In addition, cDNA was generated from the extracted RNA. SaCas9 sequence was amplified by PCR, cloned into TOPO vector, and sequenced. The fold change of specific transcripts of the self-inactivating SaCas9 constructs compared to the wild-type SaCas9 construct are shown in FIG. 7B. Transcripts containing SaCas9 coding sequence were significantly reduced in tissues transduced with AC-m9-WT PAM construct (self-inactivating SaCas9 having target site inserted at the AC1 site of the SaCas9 coding sequence) and BB-m7-AC-m9 construct (self-inactivating SaCas9 having target site inserted both in the AAV backbone and at the AC1 site of the SaCas9 coding sequence).

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments described herein. Such equivalents are intended to be encompassed by the following claims.

We claim:

1. An isolated nucleic acid encoding an RNA-guided nuclease comprising a eukaryotic nucleic acid sequence, wherein the eukaryotic nucleic acid sequence is at least 17 nucleotides in length and either comprises or is adjacent to a protospacer adjacent motif (PAM) that is recognized by the RNA-guided nuclease,
   wherein the RNA-guided nuclease is a Cas9 protein,
   wherein the Cas9 protein comprises an amino acid insertion relative to SEQ ID NO: 2 selected from the group consisting of:
   E271_N272insGX$_{6-10}$G,
   L371_N372insGX$_{6-10}$G, and
   Q737_A738insGX$_{6-10}$G; or
   wherein the Cas9 protein comprises an amino acid insertion S12_M13insGX$_{6-10}$G relative to SEQ ID NO: 10,
   which results in a polypeptide comprising an amino acid sequence having at least 95% sequence identity to a sequence selected from the group consisting of SEQ ID NOs: 3-5 and 10 and having an RNA-guided nuclease activity.

2. The isolated nucleic acid of claim 1, further encoding a guide RNA (gRNA) comprising a targeting domain that is complementary to a portion of the eukaryotic nucleic acid sequence that is adjacent to the PAM.

3. The isolated nucleic acid of claim 2, wherein the targeting domain of the gRNA is 16-24 nucleotides in length.

4. The isolated nucleic acid of claim 1, wherein the eukaryotic nucleic acid sequence is within a portion of the nucleic acid that includes, at each of its 3' and 5' ends, at least one codon for glycine, alanine or valine.

5. The isolated nucleic acid of claim 1, comprising an insertion, relative to SEQ ID NO: 6, selected from the group consisting of:
c.813_814insN$_{24-36}$,
c.1113_1114ins N$_{24-36}$, and
c.2211_2212insN$_{24-36}$; or
comprising an insertion c.36_37insN$_{24-36}$ relative to SEQ ID NO: 11.

6. The isolated nucleic acid of claim 1, comprising a nucleic acid sequence having at least 95% sequence identity to a sequence selected from the group consisting of SEQ ID NOs: 7-9 and 11.

7. The isolated nucleic acid of claim 1, wherein the Cas9 protein comprises an amino acid insertion relative to SEQ ID NO: 2, which is E271_N272insGX$_{6-10}$G.

8. The isolated nucleic acid of claim 1, wherein the Cas9 protein comprises an amino acid insertion relative to SEQ ID NO: 2, which is L371_N372insGX$_{6-10}$G.

9. The isolated nucleic acid of claim 1, wherein the Cas9 protein comprises an amino acid insertion relative to SEQ ID NO: 2, which is Q737_A738insGX$_{6-10}$G.

10. The isolated nucleic acid of claim 1, wherein the Cas9 protein comprises an amino acid insertion relative to SEQ ID NO: 10, which is S12_M13insGX$_{6-10}$G.

11. The isolated nucleic acid of claim 1, wherein the isolated nucleic acid comprises an insertion relative to SEQ ID NO: 6, which is c.813_814insN$_{24-36}$.

12. The isolated nucleic acid of claim 1, wherein the isolated nucleic acid comprises an insertion relative to SEQ ID NO: 6, which is c.1113_1114insN$_{24-36}$.

13. The isolated nucleic acid of claim 1, wherein the isolated nucleic acid comprises an insertion relative to SEQ ID NO: 6, which is c.2211_2212insN$_{24-36}$.

14. The isolated nucleic acid of claim 1, wherein the isolated nucleic acid comprises an insertion relative to SEQ ID NO: 11, which is c.36_37insN$_{24-36}$.

* * * * *

SEQUENCE LISTING

<160> NUMBER OF SEQ ID NOS: 21

<210> SEQ ID NO 1
<211> LENGTH: 4520
<212> TYPE: DNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (158)..(183)
<223> OTHER INFORMATION: n is a, c, g, or t

<400> SEQUENCE: 1

```
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcctcagat ctgaattnnn nnnnnnnnn nnnnnnnnnn     180 nnnctagcgc ttaagtcgcg cattgattat tgactagtta ttaatagtaa tcaattacgg     240
ggtcattagt tcatagccca tatatggagt tccgcgttac ataacttacg gtaaatggcc     300
cgcctggctg accgcccaac gacccccgcc cattgacgtc aataatgacg tatgttccca     360
tagtaacgcc aatagggact tccattgac gtcaatgggt ggactattta cggtaaactg     420
cccacttggc agtacatcaa gtgtatcata tgccaagtac gccccctatt gacgtcaatg     480
acggtaaatg gcccgcctgg cattatgccc agtacatgac cttatgggac tttcctactt     540
ggcagtacat ctacgtatta gtcatcgcta ttaccatggt gatgcggttt tggcagtaca     600
tcaatgggcg tggatagcgg tttgactcac ggggatttcc aagtctccac cccattgacg     660
tcaatgggag tttgttttgg caccaaaatc aacgggactt tccaaaatgt cgtaacaact     720
ccgccccatt gacgcaaatg ggcggtaggc gtgtacggtg ggaggtctat ataagcagag     780
ctggtttagt gaaccgtcag atccgctaga gatccgctct agaggatccg gtactcgagg     840
aactgaaaaa ccagaaagtt aactggtaag tttagtcttt ttgtcttttta tttcaggtcc     900 cggatccggt ggtggtgcaa atcaaagaac tgctcctcag tggatgttgc ctttacttct     960
aggcctgtac ggaagtgtta cgcggccgcc accatggac cgaagaaaaa gcgcaaggtc    1020
gaagcgtcca tgaaaaggaa ctacattctg gggctggaca tcgggattac aagcgtgggg    1080
```

```
tatgggatta ttgactatga aacaagggac gtgatcgacg caggcgtcag actgttcaag   1140
gaggccaacg tggaaaacaa tgagggacgg agaagcaaga ggggagccag gcgcctgaaa   1200
cgacggagaa ggcacagaat ccagagggtg aagaaactgc tgttcgatta caacctgctg   1260
accgaccatt ctgagctgag tggaattaat ccttatgaag ccagggtgaa aggcctgagt   1320
cagaagctgt cagaggaaga gttttccgca gctctgctgc acctggctaa gcgccgagga   1380
gtgcataacg tcaatgaggt ggaagaggac accggcaacg agctgtctac aaaggaacag   1440
atctcacgca atagcaaagc tctggaagag aagtatgtcg cagagctgca gctggaacgg   1500
ctgaagaaag atggcgaggt gagagggtca attaataggt tcaagacaag cgactacgtc   1560
aaagaagcca agcagctgct gaaagtgcag aaggcttacc accagctgga tcagagcttc   1620
atcgatactt atatcgacct gctggagact cggagaaccct actatgaggg accaggagaa   1680
gggagcccct tcggatggaa agacatcaag gaatggtacg agatgctgat gggacattgc   1740
acctattttc cagaagagct gagaagcgtc aagtacgctt ataacgcaga tctgtacaac   1800
gccctgaatg acctgaacaa cctggtcatc accagggatg aaaacgagaa actggaatac   1860
tatgagaagt tccagatcat cgaaaacgtg tttaagcaga agaaaaagcc tacactgaaa   1920
cagattgcta aggagatcct ggtcaacgaa gaggacatca agggctaccg ggtgacaagc   1980
actggaaaac cagagttcac caatctgaaa gtgtatcacg atattaagga catcacagca   2040
cggaaagaaa tcattgagaa cgccgaactg ctggatcaga ttgctaagat cctgactatc   2100
taccagagct ccgaggacat ccaggaagag ctgactaacc tgaacagcga gctgacccag   2160
gaagagatcg aacagattag taatctgaag gggtacaccg aacacacaca cctgtccctg   2220
aaagctatca atctgattct ggatgagctg tggcatacaa cgacaatca gattgcaatc   2280 tttaaccggc tgaagctggt cccaaaaaag gtggacctga gtcagcagaa agagatccca   2340
accacactgg tggacgattt cattctgtca cccgtggtca gcggagcctt catccagagc   2400
atcaaagtga tcaacgccat catcaagaag tacggcctgc ccaatgatat cattatcgag   2460
ctggctaggg agaagaacag caaggacgca cagaagatga tcaatgagat gcagaaacga   2520
aaccggcaga ccaatgaacg cattgaagag attatccgaa ctaccgggaa agaaaacgca   2580
aagtacctga ttgaaaaaat caagctgcac gatatgcagg agggaaagtg tctgtattct   2640
ctggaggcca tcccctgga ggacctgctg aacaatccat tcaactacga ggtcgatcat   2700
attatcccca gaagcgtgtc cttcgacaat tcctttaaca acaaggtgct ggtcaagcag   2760
gaagagaact ctaaaaaggg caataggact ccttttccagt acctgtctag ttcagattcc   2820
aagatctctt acgaaaacct taaaaagcac attctgaatc tggccaaagg aaagggccgc   2880
atcagcaaga ccaaaaagga gtacctgctg gaagagcggg acatcaacag attctccgtc   2940
cagaaggatt ttattaaccg gaatctggtg gacacaagat acgctactcg cggcctgatg   3000
aatctgctgc gatccatttt ccgggtgaac aatctggatg tgaaagtcaa gtccatcaac   3060
ggcgggttca catcttttct gaggcgcaaa tggaagttta aaaaggagcg caacaaaggg   3120
tacaagcacc atgccgaaga tgctctgatt atcgcaaatg ccgacttcat ctttaaggag   3180
tggaaaaagc tggacaaagc caagaaagtg atggagaacc agatgttcga agagaagcag   3240
gccgaatcta tgcccgaaat cgagacagaa caggagtaca aggagatttt catcactcct   3300
caccagatca agcatatcaa ggatttcaag gactacaagt actctcaccg ggtggataaa   3360
aagcccaaca gagagctgat caatgacacc ctgtatagta caagaaaaga cgataagggg   3420
```

```
aatacccctga ttgtgaacaa tctgaacgga ctgtacgaca agataatga caagctgaaa    3480 aagctgatca acaaaagtcc cgagaagctg ctgatgtacc accatgatcc tcagacatat    3540
cagaaactga agctgattat ggagcagtac ggcgacgaga agaacccact gtataagtac    3600
tatgaagaga ctgggaacta cctgaccaag tatagcaaaa aggataatgg ccccgtgatc    3660
aagaagatca agtactatgg gaacaagctg aatgcccatc tggacatcac agacgattac    3720
cctaacagtc gcaacaaggt ggtcaagctg tcactgaagc catacagatt cgatgtctat    3780
ctggacaacg gcgtgtataa atttgtgact gtcaagaatc tggatgtcat caaaaaggag    3840
aactactatg aagtgaatag caagtgctac gaagaggcta aaaagctgaa aaagattagc    3900
aaccaggcag agttcatcgc ctccttttac aacaacgacc tgattaagat caatggcgaa    3960
ctgtataggg tcatcggggt gaacaatgat ctgctgaacc gcattgaagt gaatatgatt    4020
gacatcactt accgagagta tctggaaaac atgaatgata agcgcccccc tcgaattatc    4080
aaaacaattg cctctaagac tcagagtatc aaaaagtact caaccgacat tctgggaaac    4140
ctgtatgagg tgaagagcaa aaagcaccct cagattatca aaaagggcgg atcccccaag    4200
aagaagagga agtctcgag cgactacaaa gaccatgacg gtgattataa agatcatgac    4260
atcgattaca aggatgacga tgacaagtag caataaagga tcgtttattt tcattggaag    4320
cgtgtgttgg tttttttgatc aggcgcgtcc aagcttgcat gctggggaga gatctaggaa    4380
cccctagtga tggagttggc cactccctct ctgcgcgctc gctcgctcac tgaggccgcc    4440
cgggcaaagc ccgggcgtcg ggcgacctt ggtcgcccgg cctcagtgag cgagcgagcg    4500
cgcagagagg gagtggccaa                                                 4520
```

<210> SEQ ID NO 2
<211> LENGTH: 1053
<212> TYPE: PRT
<213> ORGANISM: Artificial sequence
<220> FEATURE:
<223> OTHER INFORMATION: Synthetic polypeptide

<400> SEQUENCE: 2

```
Met Lys Arg Asn Tyr Ile Leu Gly Leu Asp Ile Gly Ile Thr Ser Val
1               5                   10                  15

Gly Tyr Gly Ile Ile Asp Tyr Glu Thr Arg Asp Val Ile Asp Ala Gly
                20                  25                  30

Val Arg Leu Phe Lys Glu Ala Asn Val Glu Asn Asn Glu Gly Arg Arg
            35                  40                  45

Ser Lys Arg Gly Ala Arg Arg Leu Lys Arg Arg Arg His Arg Ile
        50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Glu Phe Ser Ala Ala Leu Leu His Leu
            100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala
    130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
```

```
            165                 170                 175
Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Glu Thr Arg
        195                 200                 205

Arg Thr Tyr Tyr Glu Gly Pro Gly Glu Gly Ser Pro Phe Gly Trp Lys
    210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
            260                 265                 270

Glu Lys Leu Glu Tyr Tyr Glu Lys Phe Gln Ile Ile Glu Asn Val Phe
        275                 280                 285

Lys Gln Lys Lys Lys Pro Thr Leu Lys Gln Ile Ala Lys Glu Ile Leu
    290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                325                 330                 335

Ala Arg Lys Glu Ile Ile Glu Asn Ala Glu Leu Leu Asp Gln Ile Ala
            340                 345                 350

Lys Ile Leu Thr Ile Tyr Gln Ser Ser Glu Asp Ile Gln Glu Glu Leu
        355                 360                 365

Thr Asn Leu Asn Ser Glu Leu Thr Gln Glu Glu Ile Glu Gln Ile Ser
    370                 375                 380

Asn Leu Lys Gly Tyr Thr Gly Thr His Asn Leu Ser Leu Lys Ala Ile
385                 390                 395                 400

Asn Leu Ile Leu Asp Glu Leu Trp His Thr Asn Asp Asn Gln Ile Ala
                405                 410                 415

Ile Phe Asn Arg Leu Lys Leu Val Pro Lys Lys Val Asp Leu Ser Gln
            420                 425                 430

Gln Lys Glu Ile Pro Thr Thr Leu Val Asp Asp Phe Ile Leu Ser Pro
        435                 440                 445

Val Val Lys Arg Ser Phe Ile Gln Ser Ile Lys Val Ile Asn Ala Ile
    450                 455                 460

Ile Lys Lys Tyr Gly Leu Pro Asn Asp Ile Ile Ile Glu Leu Ala Arg
465                 470                 475                 480

Glu Lys Asn Ser Lys Asp Ala Gln Lys Met Ile Asn Glu Met Gln Lys
                485                 490                 495

Arg Asn Arg Gln Thr Asn Glu Arg Ile Glu Glu Ile Ile Arg Thr Thr
            500                 505                 510

Gly Lys Glu Asn Ala Lys Tyr Leu Ile Glu Lys Ile Lys Leu His Asp
        515                 520                 525

Met Gln Glu Gly Lys Cys Leu Tyr Ser Leu Glu Ala Ile Pro Leu Glu
    530                 535                 540

Asp Leu Leu Asn Asn Pro Phe Asn Tyr Glu Val Asp His Ile Ile Pro
545                 550                 555                 560

Arg Ser Val Ser Phe Asp Asn Ser Phe Asn Asn Lys Val Leu Val Lys
                565                 570                 575

Gln Glu Glu Asn Ser Lys Lys Gly Asn Arg Thr Pro Phe Gln Tyr Leu
            580                 585                 590
```

```
Ser Ser Ser Asp Ser Lys Ile Ser Tyr Glu Thr Phe Lys Lys His Ile
            595                 600                 605

Leu Asn Leu Ala Lys Gly Lys Gly Arg Ile Ser Lys Thr Lys Lys Glu
610                 615                 620

Tyr Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
                    645                 650                 655

Met Asn Leu Leu Arg Ser Tyr Phe Arg Val Asn Asn Leu Asp Val Lys
                660                 665                 670

Val Lys Ser Ile Asn Gly Gly Phe Thr Ser Phe Leu Arg Arg Lys Trp
            675                 680                 685

Lys Phe Lys Lys Glu Arg Asn Lys Gly Tyr Lys His His Ala Glu Asp
690                 695                 700

Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Glu Lys
                725                 730                 735

Gln Ala Glu Ser Met Pro Glu Ile Glu Thr Gln Gln Tyr Lys Glu
                740                 745                 750

Ile Phe Ile Thr Pro His Gln Ile Lys His Ile Lys Asp Phe Lys Asp
            755                 760                 765

Tyr Lys Tyr Ser His Arg Val Asp Lys Lys Pro Asn Arg Glu Leu Ile
770                 775                 780

Asn Asp Thr Leu Tyr Ser Thr Arg Lys Asp Lys Gly Asn Thr Leu
785                 790                 795                 800

Ile Val Asn Asn Leu Asn Gly Leu Tyr Asp Lys Asp Asn Asp Lys Leu
                805                 810                 815

Lys Lys Leu Ile Asn Lys Ser Pro Glu Lys Leu Leu Met Tyr His His
                820                 825                 830

Asp Pro Gln Thr Tyr Gln Lys Leu Lys Leu Ile Met Glu Gln Tyr Gly
        835                 840                 845

Asp Glu Lys Asn Pro Leu Tyr Lys Tyr Tyr Glu Glu Thr Gly Asn Tyr
        850                 855                 860

Leu Thr Lys Tyr Ser Lys Lys Asp Asn Gly Pro Val Ile Lys Lys Ile
865                 870                 875                 880

Lys Tyr Tyr Gly Asn Lys Leu Asn Ala His Leu Asp Ile Thr Asp Asp
                885                 890                 895

Tyr Pro Asn Ser Arg Asn Lys Val Val Lys Leu Ser Leu Lys Pro Tyr
            900                 905                 910

Arg Phe Asp Val Tyr Leu Asp Asn Gly Val Tyr Lys Phe Val Thr Val
            915                 920                 925

Lys Asn Leu Asp Val Ile Lys Lys Glu Asn Tyr Tyr Glu Val Asn Ser
930                 935                 940

Lys Cys Tyr Glu Glu Ala Lys Lys Leu Lys Lys Ile Ser Asn Gln Ala
945                 950                 955                 960

Glu Phe Ile Ala Ser Phe Tyr Asn Asn Asp Leu Ile Lys Ile Asn Gly
                965                 970                 975

Glu Leu Tyr Arg Val Ile Gly Val Asn Asn Asp Leu Leu Asn Arg Ile
            980                 985                 990

Glu Val Asn Met Ile Asp Ile Thr  Tyr Arg Glu Tyr Leu  Glu Asn Met
                995                 1000                1005
```

```
Asn Asp Lys Arg Pro Pro Arg Ile Ile Lys Thr Ile Ala Ser Lys
    1010                1015                1020

Thr Gln Ser Ile Lys Lys Tyr Ser Thr Asp Ile Leu Gly Asn Leu
    1025                1030                1035

Tyr Glu Val Lys Ser Lys Lys His Pro Gln Ile Ile Lys Lys Gly
    1040                1045                1050

<210> SEQ ID NO 3
<211> LENGTH: 1065
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (272)..(283)
<223> OTHER INFORMATION: Xaa can be any naturally occurring amino acid

<400> SEQUENCE: 3

Met Lys Arg Asn Tyr Ile Leu Gly Leu Asp Ile Gly Ile Thr Ser Val
1               5                   10                  15

Gly Tyr Gly Ile Ile Asp Tyr Glu Thr Arg Asp Val Ile Asp Ala Gly
                20                  25                  30

Val Arg Leu Phe Lys Glu Ala Asn Val Glu Asn Asn Glu Gly Arg Arg
                35                  40                  45

Ser Lys Arg Gly Ala Arg Arg Leu Lys Arg Arg Arg His Arg Ile
50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Phe Ser Ala Ala Leu Leu His Leu
                100                 105                 110

Ala Lys Arg Arg Gly Val His Asn Val Asn Glu Val Glu Glu Asp Thr
                115                 120                 125

Gly Asn Glu Leu Ser Thr Lys Glu Gln Ile Ser Arg Asn Ser Lys Ala
130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
                180                 185                 190

Leu Asp Gln Ser Phe Ile Asp Thr Tyr Ile Asp Leu Leu Glu Thr Arg
                195                 200                 205

Arg Thr Tyr Tyr Glu Gly Pro Gly Glu Gly Ser Pro Phe Gly Trp Lys
                210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Xaa
                260                 265                 270

Xaa Xaa Xaa Xaa Xaa Xaa Xaa Xaa Xaa Xaa Xaa Asn Glu Lys Leu Glu
                275                 280                 285

Tyr Tyr Glu Lys Phe Gln Ile Ile Glu Asn Val Phe Lys Gln Lys Lys
                290                 295                 300
```

```
Lys Pro Thr Leu Lys Gln Ile Ala Lys Glu Ile Leu Val Asn Glu Glu
305                 310                 315                 320

Asp Ile Lys Gly Tyr Arg Val Thr Ser Thr Gly Lys Pro Glu Phe Thr
            325                 330                 335

Asn Leu Lys Val Tyr His Asp Ile Lys Asp Ile Thr Ala Arg Lys Glu
        340                 345                 350

Ile Ile Glu Asn Ala Glu Leu Leu Asp Gln Ile Ala Lys Ile Leu Thr
    355                 360                 365

Ile Tyr Gln Ser Ser Glu Asp Ile Gln Glu Glu Leu Thr Asn Leu Asn
370                 375                 380

Ser Glu Leu Thr Gln Glu Ile Glu Gln Ile Ser Asn Leu Lys Gly
385                 390                 395                 400

Tyr Thr Gly Thr His Asn Leu Ser Leu Lys Ala Ile Asn Leu Ile Leu
                405                 410                 415

Asp Glu Leu Trp His Thr Asn Asp Asn Gln Ile Ala Ile Phe Asn Arg
            420                 425                 430

Leu Lys Leu Val Pro Lys Lys Val Asp Leu Ser Gln Gln Lys Glu Ile
        435                 440                 445

Pro Thr Thr Leu Val Asp Asp Phe Ile Leu Ser Pro Val Val Lys Arg
    450                 455                 460

Ser Phe Ile Gln Ser Ile Lys Val Ile Asn Ala Ile Ile Lys Lys Tyr
465                 470                 475                 480

Gly Leu Pro Asn Asp Ile Ile Glu Leu Ala Arg Glu Lys Asn Ser
                485                 490                 495

Lys Asp Ala Gln Lys Met Ile Asn Glu Met Gln Lys Arg Asn Arg Gln
            500                 505                 510

Thr Asn Glu Arg Ile Glu Glu Ile Ile Arg Thr Thr Gly Lys Glu Asn
        515                 520                 525

Ala Lys Tyr Leu Ile Glu Lys Ile Lys Leu His Asp Met Gln Glu Gly
    530                 535                 540

Lys Cys Leu Tyr Ser Leu Glu Ala Ile Pro Leu Glu Asp Leu Leu Asn
545                 550                 555                 560

Asn Pro Phe Asn Tyr Glu Val Asp His Ile Ile Pro Arg Ser Val Ser
                565                 570                 575

Phe Asp Asn Ser Phe Asn Asn Lys Val Leu Val Lys Gln Glu Glu Asn
            580                 585                 590

Ser Lys Lys Gly Asn Arg Thr Pro Phe Gln Tyr Leu Ser Ser Ser Asp
        595                 600                 605

Ser Lys Ile Ser Tyr Glu Thr Phe Lys Lys His Ile Leu Asn Leu Ala
    610                 615                 620

Lys Gly Lys Gly Arg Ile Ser Lys Thr Lys Lys Glu Tyr Leu Leu Glu
625                 630                 635                 640

Glu Arg Asp Ile Asn Arg Phe Ser Val Gln Lys Asp Phe Ile Asn Arg
                645                 650                 655

Asn Leu Val Asp Thr Arg Tyr Ala Thr Arg Gly Leu Met Asn Leu Leu
            660                 665                 670

Arg Ser Tyr Phe Arg Val Asn Asn Leu Asp Val Lys Val Lys Ser Ile
        675                 680                 685

Asn Gly Gly Phe Thr Ser Phe Leu Arg Arg Lys Trp Lys Phe Lys Lys
    690                 695                 700

Glu Arg Asn Lys Gly Tyr Lys His His Ala Glu Asp Ala Leu Ile Ile
705                 710                 715                 720
```

```
Ala Asn Ala Asp Phe Ile Phe Lys Glu Trp Lys Lys Leu Asp Lys Ala
            725                 730                 735

Lys Lys Val Met Glu Asn Gln Met Phe Glu Glu Lys Gln Ala Glu Ser
        740                 745                 750

Met Pro Glu Ile Glu Thr Glu Gln Glu Tyr Lys Glu Ile Phe Ile Thr
        755                 760                 765

Pro His Gln Ile Lys His Ile Lys Asp Phe Lys Asp Tyr Lys Tyr Ser
        770                 775                 780

His Arg Val Asp Lys Lys Pro Asn Arg Glu Leu Ile Asn Asp Thr Leu
785                 790                 795                 800

Tyr Ser Thr Arg Lys Asp Asp Lys Gly Asn Thr Leu Ile Val Asn Asn
                805                 810                 815

Leu Asn Gly Leu Tyr Asp Lys Asp Asn Asp Lys Leu Lys Lys Leu Ile
                820                 825                 830

Asn Lys Ser Pro Glu Lys Leu Leu Met Tyr His His Asp Pro Gln Thr
            835                 840                 845

Tyr Gln Lys Leu Lys Leu Ile Met Glu Gln Tyr Gly Asp Glu Lys Asn
850                 855                 860

Pro Leu Tyr Lys Tyr Tyr Glu Glu Thr Gly Asn Tyr Leu Thr Lys Tyr
865                 870                 875                 880

Ser Lys Lys Asp Asn Gly Pro Val Ile Lys Lys Ile Lys Tyr Tyr Gly
                885                 890                 895

Asn Lys Leu Asn Ala His Leu Asp Ile Thr Asp Asp Tyr Pro Asn Ser
            900                 905                 910

Arg Asn Lys Val Val Lys Leu Ser Leu Lys Pro Tyr Arg Phe Asp Val
        915                 920                 925

Tyr Leu Asp Asn Gly Val Tyr Lys Phe Val Thr Val Lys Asn Leu Asp
930                 935                 940

Val Ile Lys Lys Glu Asn Tyr Tyr Glu Val Asn Ser Lys Cys Tyr Glu
945                 950                 955                 960

Glu Ala Lys Lys Leu Lys Lys Ile Ser Asn Gln Ala Glu Phe Ile Ala
                965                 970                 975

Ser Phe Tyr Asn Asn Asp Leu Ile Lys Ile Asn Gly Glu Leu Tyr Arg
            980                 985                 990

Val Ile Gly Val Asn Asn Asp Leu Leu Asn Arg Ile Glu Val Asn Met
        995                1000                1005

Ile Asp Ile Thr Tyr Arg Glu Tyr Leu Glu Asn Met Asn Asp Lys
    1010                1015                1020

Arg Pro Pro Arg Ile Ile Lys Thr Ile Ala Ser Lys Thr Gln Ser
    1025                1030                1035

Ile Lys Lys Tyr Ser Thr Asp Ile Leu Gly Asn Leu Tyr Glu Val
    1040                1045                1050

Lys Ser Lys Lys His Pro Gln Ile Ile Lys Lys Gly
    1055                1060                1065

<210> SEQ ID NO 4
<211> LENGTH: 1065
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (372)..(383)
<223> OTHER INFORMATION: Xaa can be any naturally occurring amino acid

<400> SEQUENCE: 4
```

```
Met Lys Arg Asn Tyr Ile Leu Gly Leu Asp Ile Gly Ile Thr Ser Val
1               5                   10                  15

Gly Tyr Gly Ile Ile Asp Tyr Glu Thr Arg Asp Val Ile Asp Ala Gly
                20                  25                  30

Val Arg Leu Phe Lys Glu Ala Asn Val Glu Asn Asn Glu Gly Arg Arg
            35                  40                  45

Ser Lys Arg Gly Ala Arg Arg Leu Lys Arg Arg Arg His Arg Ile
    50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Phe Ser Ala Ala Leu Leu His Leu
                100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala
    130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
                180                 185                 190

Leu Asp Gln Ser Phe Ile Asp Thr Tyr Ile Asp Leu Leu Glu Thr Arg
            195                 200                 205

Arg Thr Tyr Tyr Glu Gly Pro Gly Glu Gly Ser Pro Phe Gly Trp Lys
    210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
            260                 265                 270

Glu Lys Leu Glu Tyr Tyr Glu Lys Phe Gln Ile Ile Glu Asn Val Phe
    275                 280                 285

Lys Gln Lys Lys Lys Pro Thr Leu Lys Gln Ile Ala Lys Glu Ile Leu
290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
            325                 330                 335

Ala Arg Lys Glu Ile Ile Glu Asn Ala Glu Leu Leu Asp Gln Ile Ala
        340                 345                 350

Lys Ile Leu Thr Ile Tyr Gln Ser Ser Glu Asp Ile Gln Glu Glu Leu
    355                 360                 365

Thr Asn Leu Xaa Xaa Xaa Xaa Xaa Xaa Xaa Xaa Xaa Xaa Xaa Asn
    370                 375                 380

Ser Glu Leu Thr Gln Glu Glu Ile Glu Gln Ile Ser Asn Leu Lys Gly
385                 390                 395                 400

Tyr Thr Gly Thr His Asn Leu Ser Leu Lys Ala Ile Asn Leu Ile Leu
                405                 410                 415
```

Asp Glu Leu Trp His Thr Asn Asp Asn Gln Ile Ala Ile Phe Asn Arg
            420                 425                 430

Leu Lys Leu Val Pro Lys Lys Val Asp Leu Ser Gln Gln Lys Glu Ile
        435                 440                 445

Pro Thr Thr Leu Val Asp Asp Phe Ile Leu Ser Pro Val Val Lys Arg
    450                 455                 460

Ser Phe Ile Gln Ser Ile Lys Val Ile Asn Ala Ile Ile Lys Lys Tyr
465                 470                 475                 480

Gly Leu Pro Asn Asp Ile Ile Glu Leu Ala Arg Glu Lys Asn Ser
                485                 490                 495

Lys Asp Ala Gln Lys Met Ile Asn Glu Met Gln Lys Arg Asn Arg Gln
        500                 505                 510

Thr Asn Glu Arg Ile Glu Glu Ile Ile Arg Thr Thr Gly Lys Glu Asn
    515                 520                 525

Ala Lys Tyr Leu Ile Glu Lys Ile Lys Leu His Asp Met Gln Glu Gly
        530                 535                 540

Lys Cys Leu Tyr Ser Leu Glu Ala Ile Pro Leu Glu Asp Leu Leu Asn
545                 550                 555                 560

Asn Pro Phe Asn Tyr Glu Val Asp His Ile Ile Pro Arg Ser Val Ser
                565                 570                 575

Phe Asp Asn Ser Phe Asn Asn Lys Val Leu Val Lys Gln Glu Glu Asn
            580                 585                 590

Ser Lys Lys Gly Asn Arg Thr Pro Phe Gln Tyr Leu Ser Ser Ser Asp
        595                 600                 605

Ser Lys Ile Ser Tyr Glu Thr Phe Lys Lys His Ile Leu Asn Leu Ala
    610                 615                 620

Lys Gly Lys Gly Arg Ile Ser Lys Thr Lys Lys Glu Tyr Leu Leu Glu
625                 630                 635                 640

Glu Arg Asp Ile Asn Arg Phe Ser Val Gln Lys Asp Phe Ile Asn Arg
                645                 650                 655

Asn Leu Val Asp Thr Arg Tyr Ala Thr Arg Gly Leu Met Asn Leu Leu
            660                 665                 670

Arg Ser Tyr Phe Arg Val Asn Asn Leu Asp Val Lys Val Lys Ser Ile
        675                 680                 685

Asn Gly Gly Phe Thr Ser Phe Leu Arg Arg Lys Trp Lys Phe Lys Lys
    690                 695                 700

Glu Arg Asn Lys Gly Tyr Lys His His Ala Glu Asp Ala Leu Ile Ile
705                 710                 715                 720

Ala Asn Ala Asp Phe Ile Phe Lys Glu Trp Lys Lys Leu Asp Lys Ala
                725                 730                 735

Lys Lys Val Met Glu Asn Gln Met Phe Glu Glu Lys Gln Ala Glu Ser
            740                 745                 750

Met Pro Glu Ile Glu Thr Glu Gln Glu Tyr Lys Glu Ile Phe Ile Thr
        755                 760                 765

Pro His Gln Ile Lys His Ile Lys Asp Phe Lys Asp Tyr Lys Tyr Ser
    770                 775                 780

His Arg Val Asp Lys Lys Pro Asn Arg Glu Leu Ile Asn Asp Thr Leu
785                 790                 795                 800

Tyr Ser Thr Arg Lys Asp Asp Lys Gly Asn Thr Leu Ile Val Asn Asn
                805                 810                 815

Leu Asn Gly Leu Tyr Asp Lys Asp Asn Asp Lys Leu Lys Lys Leu Ile
            820                 825                 830

Asn Lys Ser Pro Glu Lys Leu Leu Met Tyr His His Asp Pro Gln Thr

```
                    835                 840                 845

Tyr Gln Lys Leu Lys Leu Ile Met Glu Gln Tyr Gly Asp Glu Lys Asn
    850                 855                 860

Pro Leu Tyr Lys Tyr Tyr Glu Glu Thr Gly Asn Tyr Leu Thr Lys Tyr
865                 870                 875                 880

Ser Lys Lys Asp Asn Gly Pro Val Ile Lys Ile Lys Tyr Tyr Gly
                885                 890                 895

Asn Lys Leu Asn Ala His Leu Asp Ile Thr Asp Tyr Pro Asn Ser
            900                 905                 910

Arg Asn Lys Val Val Lys Leu Ser Leu Lys Pro Tyr Arg Phe Asp Val
        915                 920                 925

Tyr Leu Asp Asn Gly Val Tyr Lys Phe Val Thr Val Lys Asn Leu Asp
    930                 935                 940

Val Ile Lys Lys Glu Asn Tyr Glu Val Asn Ser Lys Cys Tyr Glu
945                 950                 955                 960

Glu Ala Lys Lys Leu Lys Lys Ile Ser Asn Gln Ala Glu Phe Ile Ala
                965                 970                 975

Ser Phe Tyr Asn Asn Asp Leu Ile Lys Ile Asn Gly Glu Leu Tyr Arg
            980                 985                 990

Val Ile Gly Val Asn Asn Asp Leu  Leu Asn Arg Ile Glu  Val Asn Met
        995                  1000                 1005

Ile Asp Ile Thr Tyr Arg Glu  Tyr Leu Glu Asn Met  Asn Asp Lys
    1010                 1015                 1020

Arg Pro Pro Arg Ile Ile Lys  Thr Ile Ala Ser Lys  Thr Gln Ser
1025                 1030                 1035

Ile Lys Lys Tyr Ser Thr Asp  Ile Leu Gly Asn Leu  Tyr Glu Val
    1040                 1045                 1050

Lys Ser Lys Lys His Pro Gln  Ile Ile Lys Lys Gly
    1055                 1060                 1065

<210> SEQ ID NO 5
<211> LENGTH: 1065
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (738)..(749)
<223> OTHER INFORMATION: Xaa can be any naturally occurring amino acid

<400> SEQUENCE: 5

Met Lys Arg Asn Tyr Ile Leu Gly Leu Asp Ile Gly Ile Thr Ser Val
1               5                   10                  15

Gly Tyr Gly Ile Ile Asp Tyr Glu Thr Arg Asp Val Ile Asp Ala Gly
            20                  25                  30

Val Arg Leu Phe Lys Glu Ala Asn Val Glu Asn Asn Glu Gly Arg Arg
        35                  40                  45

Ser Lys Arg Gly Ala Arg Arg Leu Lys Arg Arg Arg His Arg Ile
    50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Glu Phe Ser Ala Ala Leu Leu His Leu
            100                 105                 110
```

```
Ala Lys Arg Arg Gly Val His Asn Val Asn Glu Val Glu Glu Asp Thr
            115                 120                 125

Gly Asn Glu Leu Ser Thr Lys Glu Gln Ile Ser Arg Asn Ser Lys Ala
        130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Leu Glu Thr Arg
        195                 200                 205

Arg Thr Tyr Tyr Glu Gly Pro Gly Glu Gly Ser Pro Phe Gly Trp Lys
    210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
            260                 265                 270

Glu Lys Leu Glu Tyr Tyr Glu Lys Phe Gln Ile Ile Glu Asn Val Phe
        275                 280                 285

Lys Gln Lys Lys Lys Pro Thr Leu Lys Gln Ile Ala Lys Glu Ile Leu
    290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                325                 330                 335

Ala Arg Lys Glu Ile Ile Glu Asn Ala Glu Leu Leu Asp Gln Ile Ala
            340                 345                 350

Lys Ile Leu Thr Ile Tyr Gln Ser Ser Glu Asp Ile Gln Glu Glu Leu
        355                 360                 365

Thr Asn Leu Asn Ser Glu Leu Thr Gln Glu Glu Ile Glu Gln Ile Ser
    370                 375                 380

Asn Leu Lys Gly Tyr Thr Gly Thr His Asn Leu Ser Leu Lys Ala Ile
385                 390                 395                 400

Asn Leu Ile Leu Asp Glu Leu Trp His Thr Asn Asp Asn Gln Ile Ala
                405                 410                 415

Ile Phe Asn Arg Leu Lys Leu Val Pro Lys Lys Val Asp Leu Ser Gln
            420                 425                 430

Gln Lys Glu Ile Pro Thr Thr Leu Val Asp Asp Phe Ile Leu Ser Pro
        435                 440                 445

Val Val Lys Arg Ser Phe Ile Gln Ser Ile Lys Val Ile Asn Ala Ile
    450                 455                 460

Ile Lys Lys Tyr Gly Leu Pro Asn Asp Ile Ile Ile Glu Leu Ala Arg
465                 470                 475                 480

Glu Lys Asn Ser Lys Asp Ala Gln Lys Met Ile Asn Glu Met Gln Lys
                485                 490                 495

Arg Asn Arg Gln Thr Asn Glu Arg Ile Glu Glu Ile Ile Arg Thr Thr
            500                 505                 510

Gly Lys Glu Asn Ala Lys Tyr Leu Ile Glu Lys Ile Lys Leu His Asp
        515                 520                 525

Met Gln Glu Gly Lys Cys Leu Tyr Ser Leu Glu Ala Ile Pro Leu Glu
```

-continued

```
        530             535             540
Asp Leu Leu Asn Asn Pro Phe Asn Tyr Glu Val Asp His Ile Ile Pro
545                 550                 555                 560

Arg Ser Val Ser Phe Asp Asn Ser Phe Asn Asn Lys Val Leu Val Lys
                565                 570                 575

Gln Glu Glu Asn Ser Lys Lys Gly Asn Arg Thr Pro Phe Gln Tyr Leu
            580                 585                 590

Ser Ser Ser Asp Ser Lys Ile Ser Tyr Glu Thr Phe Lys Lys His Ile
        595                 600                 605

Leu Asn Leu Ala Lys Gly Lys Gly Arg Ile Ser Lys Thr Lys Lys Glu
    610                 615                 620

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
                645                 650                 655

Met Asn Leu Leu Arg Ser Tyr Phe Arg Val Asn Asn Leu Asp Val Lys
            660                 665                 670

Val Lys Ser Ile Asn Gly Gly Phe Thr Ser Phe Leu Arg Arg Lys Trp
        675                 680                 685

Lys Phe Lys Lys Glu Arg Asn Lys Gly Tyr Lys His His Ala Glu Asp
    690                 695                 700

Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Glu Lys
                725                 730                 735

Gln Xaa Xaa Xaa Xaa Xaa Xaa Xaa Xaa Xaa Xaa Xaa Xaa Ala Glu Ser
            740                 745                 750

Met Pro Glu Ile Glu Thr Glu Gln Glu Tyr Lys Glu Ile Phe Ile Thr
        755                 760                 765

Pro His Gln Ile Lys His Ile Lys Asp Phe Lys Asp Tyr Lys Tyr Ser
    770                 775                 780

His Arg Val Asp Lys Lys Pro Asn Arg Glu Leu Ile Asn Asp Thr Leu
785                 790                 795                 800

Tyr Ser Thr Arg Lys Asp Asp Lys Gly Asn Thr Leu Ile Val Asn Asn
                805                 810                 815

Leu Asn Gly Leu Tyr Asp Lys Asp Asn Asp Lys Leu Lys Lys Leu Ile
            820                 825                 830

Asn Lys Ser Pro Glu Lys Leu Leu Met Tyr His His Asp Pro Gln Thr
        835                 840                 845

Tyr Gln Lys Leu Lys Leu Ile Met Glu Gln Tyr Gly Asp Glu Lys Asn
    850                 855                 860

Pro Leu Tyr Lys Tyr Tyr Glu Glu Thr Gly Asn Tyr Leu Thr Lys Tyr
865                 870                 875                 880

Ser Lys Lys Asp Asn Gly Pro Val Ile Lys Lys Ile Lys Tyr Tyr Gly
                885                 890                 895

Asn Lys Leu Asn Ala His Leu Asp Ile Thr Asp Asp Tyr Pro Asn Ser
            900                 905                 910

Arg Asn Lys Val Val Lys Leu Ser Leu Lys Pro Tyr Arg Phe Asp Val
        915                 920                 925

Tyr Leu Asp Asn Gly Val Tyr Lys Phe Val Thr Val Lys Asn Leu Asp
    930                 935                 940

Val Ile Lys Lys Glu Asn Tyr Tyr Glu Val Asn Ser Lys Cys Tyr Glu
945                 950                 955                 960
```

Glu Ala Lys Lys Leu Lys Lys Ile Ser Asn Gln Ala Glu Phe Ile Ala
             965                 970                 975

Ser Phe Tyr Asn Asn Asp Leu Ile Lys Ile Asn Gly Glu Leu Tyr Arg
        980                 985                 990

Val Ile Gly Val Asn Asn Asp Leu Leu Asn Arg Ile Glu Val Asn Met
    995                 1000                1005

Ile Asp Ile Thr Tyr Arg Glu Tyr Leu Glu Asn Met Asn Asp Lys
    1010                1015                1020

Arg Pro Pro Arg Ile Ile Lys Thr Ile Ala Ser Lys Thr Gln Ser
    1025                1030                1035

Ile Lys Lys Tyr Ser Thr Asp Ile Leu Gly Asn Leu Tyr Glu Val
    1040                1045                1050

Lys Ser Lys Lys His Pro Gln Ile Ile Lys Lys Gly
    1055                1060                1065

<210> SEQ ID NO 6
<211> LENGTH: 3159
<212> TYPE: DNA
<213> ORGANISM: Artificial sequence
<220> FEATURE:
<223> OTHER INFORMATION: Synthetic nucleic acid

<400> SEQUENCE: 6
atgaaaagga actacattct ggggctggac atcgggatta caagcgtggg gtatgggatt      60
attgactatg aaacaaggga cgtgatcgac gcaggcgtca gactgttcaa ggaggccaac     120
gtggaaaaca atgagggacg gagaagcaag aggggagcca ggcgcctgaa acgacgagaa     180
aggcacagaa tccagagggt gaagaaactg ctgttcgatt acaacctgct gaccgaccat     240
tctgagctga gtggaattaa tccttatgaa gccagggtga aaggcctgag tcagaagctg     300
tcagaggaag agttttccgc agctctgctg cacctggcta agcgccgagg agtgcataac     360
gtcaatgagg tggaagagga caccggcaac gagctgtcta caaggaaca gatctcacgc      420 aatagcaaag ctctggaaga gaagtatgtc gcagagctgc agctggaacg gctgaagaaa     480
gatggcgagg tgagagggtc aattaatagg ttcaagacaa gcgactacgt caaagaagcc     540
aagcagctgc tgaaagtgca gaaggcttac caccagctgg atcagagctt catcgatact     600
tatatcgacc tgctggagac tcggagaacc tactatgagg gaccaggaga agggagcccc     660
ttcggatgga aagacatcaa ggaatggtac gagatgctga tgggacattg cacctatttt     720
ccagaagagc tgagaagcgt caagtacgct tataacgcag atctgtacaa cgccctgaat     780
gacctgaaca acctggtcat caccagggat gaaaacgaga actggaata ctatgagaag      840 ttccagatca tcgaaaacgt gtttaagcag aagaaaagc ctacactgaa acagattgct      900
aaggagatcc tggtcaacga agaggacatc aagggctacc gggtgacaag cactggaaaa     960
ccagagttca ccaatctgaa agtgtatcac gatattaagg acatcacagc acggaaagaa    1020
atcattgaga acgccgaact gctggatcag attgctaaga tcctgactat ctaccagagc    1080
tccgaggaca tccaggaaga gctgactaac ctgaacagcg agctgaccca ggaagagatc    1140
gaacagatta gtaatctgaa ggggtacacc ggaacacaca cctgtccct gaaagctatc     1200 aatctgattc tggatgagct gtggcataca aacgacaatc agattgcaat ctttaaccgg    1260
ctgaagctgg tcccaaaaaa ggtggacctg agtcagcaga agagatccc aaccacactg     1320 gtggacgatt tcattctgtc acccgtggtc aagcggagct tcatccagag catcaaagtg    1380
atcaacgcca tcatcaagaa gtacggcctg cccaatgata tcattatcga gctggctagg    1440

-continued

| | |
|---|---|
| gagaagaaca gcaaggacgc acagaagatg atcaatgaga tgcagaaacg aaaccggcag | 1500 |
| accaatgaac gcattgaaga gattatccga actaccggga agagaacgc aaagtacctg | 1560 |
| attgaaaaaa tcaagctgca cgatatgcag gagggaaagt gtctgtattc tctggaggcc | 1620 |
| atcccctgg aggacctgct gaacaatcca ttcaactacg aggtcgatca tattatcccc | 1680 |
| agaagcgtgt ccttcgacaa ttcctttaac aacaaggtgc tggtcaagca ggaagagaac | 1740 |
| tctaaaaagg gcaataggac tcctttccag tacctgtcta gttcagattc caagatctct | 1800 |
| tacgaaacct taaaaagca cattctgaat ctggccaaag gaaagggccg catcagcaag | 1860 |
| accaaaaagg agtacctgct ggaagagcgg gacatcaaca gattctccgt ccagaaggat | 1920 |
| tttattaacc ggaatctggt ggacacaaga tacgctactc gcggcctgat gaatctgctg | 1980 |
| cgatcctatt tccgggtgaa caatctggat gtgaaagtca agtccatcaa cggcgggttc | 2040 |
| acatcttttc tgaggcgcaa atggaagttt aaaaaggagc gcaacaaagg gtacaagcac | 2100 |
| catgccgaag atgctctgat tatcgcaaat gccgacttca tctttaagga gtggaaaaag | 2160 |
| ctggacaaag ccaagaaagt gatggagaac cagatgttcg aagagaagca ggccgaatct | 2220 |
| atgcccgaaa tcgagacaga acaggagtac aaggagattt tcatcactcc tcaccagatc | 2280 |
| aagcatatca aggatttcaa ggactacaag tactctcacc gggtggataa aaagcccaac | 2340 |
| agagagctga tcaatgacac cctgtatagt acaagaaaag acgataaggg gaataccctg | 2400 |
| attgtgaaca atctgaacgg actgtacgac aaagataatg acaagctgaa aaagctgatc | 2460 |
| aacaaaagtc ccgagaagct gctgatgtac caccatgatc ctcagacata tcagaaactg | 2520 |
| aagctgatta tggagcagta cggcgacgag aagaacccac tgtataagta ctatgaagag | 2580 |
| actgggaact acctgaccaa gtatagcaaa aaggataatg cccccgtgat caagaagatc | 2640 |
| aagtactatg gaacaagct gaatgcccat ctggacatca cagacgatta ccctaacagt | 2700 |
| cgcaacaagg tggtcaagct gtcactgaag ccatacagat cgatgtcta tctggacaac | 2760 |
| ggcgtgtata aatttgtgac tgtcaagaat ctggatgtca tcaaaaagga gaactactat | 2820 |
| gaagtgaata gcaagtgcta cgaagaggct aaaaagctga aaaagattag caaccaggca | 2880 |
| gagttcatcg cctcctttta caacaacgac ctgattaaga tcaatggcga actgtatagg | 2940 |
| gtcatcgggg tgaacaatga tctgctgaac cgcattgaag tgaatatgat tgacatcact | 3000 |
| taccgagagt atctgaaaaa catgaatgat aagcgccccc ctcgaattat caaaacaatt | 3060 |
| gcctctaaga ctcagagtat caaaaagtac tcaaccgaca ttctgggaaa cctgtatgag | 3120 |
| gtgaagagca aaaagcaccc tcagattatc aaaaagggc | 3159 |

<210> SEQ ID NO 7
<211> LENGTH: 3195
<212> TYPE: DNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (814)..(849)
<223> OTHER INFORMATION: n is a, c, g, or t

<400> SEQUENCE: 7

| | |
|---|---|
| atgaaaagga actacattct ggggctggac atcgggatta caagcgtggg gtatgggatt | 60 |
| attgactatg aaacaaggga cgtgatcgac gcaggcgtca gactgttcaa ggaggccaac | 120 |
| gtggaaaaca atgagggacg gagaagcaag aggggagcca ggcgcctgaa acgacggaga | 180 |

```
aggcacagaa tccagagggt gaagaaactg ctgttcgatt acaacctgct gaccgaccat    240
tctgagctga gtggaattaa tccttatgaa gccagggtga aaggcctgag tcagaagctg    300
tcagaggaag agttttccgc agctctgctg cacctggcta agcgccgagg agtgcataac    360
gtcaatgagg tggaagagga caccggcaac gagctgtcta caaggaaaca gatctcacgc    420
aatagcaaag ctctggaaga gaagtatgtc gcagagctgc agctggaacg gctgaagaaa    480
gatggcgagg tgagagggtc aattaatagg ttcaagacaa gcgactacgt caaagaagcc    540
aagcagctgc tgaaagtgca gaaggcttac caccagctgg atcagagctt catcgatact    600
tatatcgacc tgctggagac tcggagaacc tactatgagg gaccaggaga agggagcccc    660
ttcggatgga agacatcaa ggaatggtac gagatgctga tgggacattg cacctatttt    720
ccagaagagc tgagaagcgt caagtacgct ataacgcag atctgtacaa cgccctgaat    780
gacctgaaca acctggtcat caccagggat gaannnnnnn nnnnnnnnnn nnnnnnnnnn    840
nnnnnnnnna acgagaaact ggaatactat gagaagttcc agatcatcga aaacgtgttt    900
aagcagaaga aaaagcctac actgaaacag attgctaagg atcctggt caacgaagag    960 gacatcaagg gctaccgggt gacaagcact ggaaaaccag agttcaccaa tctgaaagtg    1020
tatcacgata ttaaggacat cacagcacgg aaagaaatca ttgagaacgc cgaactgctg    1080
gatcagattg ctaagatcct gactatctac cagagctccg aggacatcca ggaagagctg    1140
actaacctga cagcgagct gacccaggaa gagatcgaac agattagtaa tctgaaggg    1200 tacaccggaa cacacaacct gtccctgaaa gctatcaatc tgattctgga tgagctgtgg    1260
catacaaacg acaatcagat tgcaatcttt aaccggctga agctggtccc aaaaaaggtg    1320
gacctgagtc agcagaaaga gatcccaacc acactggtgg acgatttcat tctgtcaccc    1380
gtggtcaagc ggagcttcat ccagagcatc aaagtgatca acgccatcat caagaagtac    1440
ggcctgccca tgatatcat tatcgagctg gctagggaga gaacagcaa ggacgcacag    1500 aagatgatca atgagatgca gaaacgaaac cggcagacca tgaacgcat tgaagagatt    1560 atccgaacta ccgggaaaga gaacgcaaag tacctgattg aaaaaatcaa gctgcacgat    1620
atgcaggagg gaaagtgtct gtattctctg gaggccatcc ccctggagga cctgctgaac    1680
aatccattca actacgaggt cgatcatatt atccccagaa gcgtgtcctt cgacaattcc    1740
tttaacaaca aggtgctggt caagcaggaa gagaactcta aaaagggcaa taggactcct    1800
ttccagtacc tgtctagttc agattccaag atctcttacg aaacctttaa aaagcacatt    1860
ctgaatctgg ccaaaggaaa gggccgcatc agcaagacca aaaaggagta cctgctggaa    1920
gagcgggaca tcaacagatt ctccgtccag aaggatttta ttaaccggaa tctggtggac    1980
acaagatacg ctactcgcgg cctgatgaat ctgctgcgat cctatttccg ggtgaacaat    2040
ctggatgtga aagtcaagtc catcaacggc gggttcacat cttttctgag gcgcaaatgg    2100
aagtttaaaa aggagcgcaa caaagggtac aagcaccatg ccgaagatgc tctgattatc    2160
gcaaatgccg acttcatctt taaggagtgg aaaaagctgg acaaagccaa gaaagtgatg    2220
gagaaccaga tgttcgaaga gaagcaggcc gaatctatgc ccgaaatcga cagaacag    2280 gagtacaagg agattttcat cactcctcac cagatcaagc atatcaagga tttcaaggac    2340
tacaagtact ctcaccgggt ggataaaaag cccaacagag agctgatcaa tgacaccctg    2400
tatagtacaa gaaaagacga taaggggaat accctgattg tgaacaatct gaacggactg    2460
tacgacaaag ataatgacaa gctgaaaaag ctgatcaaca aaagtcccga agagctgctg    2520
atgtaccacc atgatcctca gacatatcag aaactgaagc tgattatgga gcagtacggc    2580
```

```
gacgagaaga acccactgta taagtactat gaagagactg ggaactacct gaccaagtat    2640
agcaaaaagg ataatggccc cgtgatcaag aagatcaagt actatgggaa caagctgaat    2700
gcccatctgg acatcacaga cgattaccct aacagtcgca acaaggtggt caagctgtca    2760
ctgaagccat acagattcga tgtctatctg gacaacggcg tgtataaatt tgtgactgtc    2820
aagaatctgg atgtcatcaa aaaggagaac tactatgaag tgaatagcaa gtgctacgaa    2880
gaggctaaaa agctgaaaaa gattagcaac caggcagagt tcatcgcctc cttttacaac    2940
aacgacctga ttaagatcaa tggcgaactg tatagggtca tcggggtgaa caatgatctg    3000
ctgaaccgca ttgaagtgaa tatgattgac atcacttacc gagagtatct ggaaaacatg    3060
aatgataagc gccccctcg aattatcaaa acaattgcct ctaagactca gagtatcaaa    3120
aagtactcaa ccgacattct gggaaacctg tatgaggtga gagcaaaaa gcaccctcag    3180 attatcaaaa agggc                                                     3195

<210> SEQ ID NO 8
<211> LENGTH: 3195
<212> TYPE: DNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (1114)..(1149)
<223> OTHER INFORMATION: n is a, c, g, or t

<400> SEQUENCE: 8
atgaaaagga actacattct ggggctggac atcgggatta caagcgtggg gtatgggatt      60
attgactatg aaacaaggga cgtgatcgac gcaggcgtca gactgttcaa ggaggccaac     120
gtggaaaaca atgagggacg gagaagcaag aggggagcca ggcgcctgaa cgacggaga     180 aggcacagaa tccagagggt gaagaaactg ctgttcgatt acaacctgct gaccgaccat     240
tctgagctga gtggaattaa tccttatgaa gccagggtga aaggcctgag tcagaagctg     300
tcagaggaag agttttccgc agctctgctg cacctggcta gcgccgagg agtgcataac     360 gtcaatgagg tggaagagga caccggcaac gagctgtcta caaaggaaca gatctcacgc     420
aatagcaaag ctctggaaga gaagtatgtc gcagagctgc agctggaacg gctgaagaaa     480
gatggcgagg tgagagggtc aattaatagg ttcaagacaa gcgactacgt caaagaagcc     540
aagcagctgc tgaaagtgca gaaggcttac caccagctgg atcagagctt catcgatact     600
tatatcgacc tgctggagac tcggagaacc tactatgagg gaccaggaga agggagcccc     660
ttcggatgga agacatcaa ggaatggtac gagatgctga tgggacattg cacctatttt     720
ccagaagagc tgaaagcgt caagtacgct tataacgcag atctgtacaa cgccctgaat     780
gacctgaaca acctggtcat caccagggat gaaaacgaga actggaata ctatgagaag     840 ttccagatca tcgaaaacgt gtttaagcag aagaaaagc ctacactgaa acagattgct     900
aaggagatcc tggtcaacga agaggacatc aagggctacc gggtgacaag cactggaaaa     960
ccagagttca ccaatctgaa agtgtatcac gatattaagg acatcacagc acggaaagaa    1020
atcattgaga acgccgaact gctggatcag attgctaaga tcctgactat ctaccagagc    1080
tccgaggaca tccaggaaga gctgactaac ctgnnnnnnn nnnnnnnnnn nnnnnnnnnn    1140
nnnnnnnnna acagcgagct gacccaggaa gagatcgaac agattagtaa tctgaagggg    1200
tacaccggaa cacacaacct gtccctgaaa gctatcaatc tgattctgga tgagctgtgg    1260
```

| | |
|---|---|
| catacaaacg acaatcagat tgcaatcttt aaccggctga agctggtccc aaaaaaggtg | 1320 |
| gacctgagtc agcagaaaga gatcccaacc acactggtgg acgatttcat tctgtcaccc | 1380 |
| gtggtcaagc ggagcttcat ccagagcatc aaagtgatca acgccatcat caagaagtac | 1440 |
| ggcctgccca atgatatcat tatcgagctg gctagggaga agaacagcaa ggacgcacag | 1500 |
| aagatgatca atgagatgca gaaacgaaac cggcagacca atgaacgcat tgaagagatt | 1560 |
| atccgaacta ccgggaaaga gaacgcaaag tacctgattg aaaaaatcaa gctgcacgat | 1620 |
| atgcaggagg gaaagtgtct gtattctctg gaggccatcc ccctggagga cctgctgaac | 1680 |
| aatccattca actacgaggt cgatcatatt atccccagaa gcgtgtcctt cgacaattcc | 1740 |
| tttaacaaca aggtgctggt caagcaggaa gagaactcta aaagggcaa taggactcct | 1800 |
| ttccagtacc tgtctagttc agattccaag atctcttacg aaacctttaa aaagcacatt | 1860 |
| ctgaatctgg ccaaaggaaa gggccgcatc agcaagacca aaaaggagta cctgctggaa | 1920 |
| gagcgggaca tcaacagatt ctccgtccag aaggatttta ttaaccggaa tctggtggac | 1980 |
| acaagatacg ctactcgcgg cctgatgaat ctgctgcgat cctatttccg ggtgaacaat | 2040 |
| ctggatgtga aagtcaagtc catcaacggc gggttcacat cttttctgag gcgcaaatgg | 2100 |
| aagtttaaaa aggagcgcaa caaagggtac aagcaccatg ccgaagatgc tctgattatc | 2160 |
| gcaaatgccg acttcatctt taaggagtgg aaaaagctgg acaaagccaa gaaagtgatg | 2220 |
| gagaaccaga tgttcgaaga aagcaggcc gaatctatgc ccgaaatcga cagaacag | 2280 |
| gagtacaagg agatttttcat cactcctcac cagatcaagc atatcaagga tttcaaggac | 2340 |
| tacaagtact ctcaccgggt ggataaaaag cccaacagag agctgatcaa tgacaccctg | 2400 |
| tatagtacaa gaaaagacga taaggggaat accctgattg tgaacaatct gaacggactg | 2460 |
| tacgacaaag ataatgacaa gctgaaaaag ctgatcaaca aaagtcccga gaagctgctg | 2520 |
| atgtaccacc atgatcctca gacatatcag aaactgaagc tgattatgga gcagtacggc | 2580 |
| gacgagaaga acccactgta taagtactat gaagagactg gaactacct gaccaagtat | 2640 |
| agcaaaaagg ataatggccc cgtgatcaag aagatcaagt actatgggaa caagctgaat | 2700 |
| gcccatctgg acatcacaga cgattaccct aacagtcgca acaaggtggt caagctgtca | 2760 |
| ctgaagccat acagattcga tgtctatctg gacaacggcg tgtataaatt tgtgactgtc | 2820 |
| aagaatctgg atgtcatcaa aaaggagaac tactatgaag tgaatagcaa gtgctacgaa | 2880 |
| gaggctaaaa agctgaaaaa gattagcaac caggcagagt tcatcgcctc cttttacaac | 2940 |
| aacgacctga ttaagatcaa tggcgaactg tatagggtca tcggggtgaa caatgatctg | 3000 |
| ctgaaccgca ttgaagtgaa tatgattgac atcacttacc gagagtatct ggaaaacatg | 3060 |
| aatgataagc gccccctcg aattatcaaa acaattgcct ctaagactca gagtatcaaa | 3120 |
| aagtactcaa ccgacattct gggaaacctg tatgaggtga gagcaaaaa gcaccctcag | 3180 |
| attatcaaaa agggc | 3195 |

<210> SEQ ID NO 9
<211> LENGTH: 3195
<212> TYPE: DNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (2212)..(2247)
<223> OTHER INFORMATION: n is a, c, g, or t

<400> SEQUENCE: 9

```
atgaaaagga actacattct ggggctggac atcgggatta caagcgtggg gtatgggatt      60
attgactatg aaacaaggga cgtgatcgac gcaggcgtca gactgttcaa ggaggccaac     120
gtggaaaaca atgagggacg gagaagcaag aggggagcca ggcgcctgaa acgacggaga     180
aggcacagaa tccagagggt gaagaaactg ctgttcgatt acaacctgct gaccgaccat     240
tctgagctga gtggaattaa tccttatgaa gccagggtga aaggcctgag tcagaagctg     300
tcagaggaag agttttccgc agctctgctg cacctggcta agcgccgagg agtgcataac     360
gtcaatgagg tggaagagga caccggcaac gagctgtcta caaaggaaca gatctcacgc     420
aatagcaaag ctctggaaga gaagtatgtc gcagagctgc agctggaacg gctgaagaaa     480
gatggcgagg tgagagggtc aattaatagg ttcaagacaa gcgactacgt caaagaagcc     540
aagcagctgc tgaaagtgca gaaggcttac caccagctgg atcagagctt catcgatact     600
tatatcgacc tgctggagac tcggagaacc tactatgagg accaggaga agggagcccc      660
ttcggatgga agacatcaa ggaatggtac gagatgctga tgggacattg cacctatttt       720
ccagaagagc tgagaagcgt caagtacgct tataacgcag atctgtacaa cgccctgaat     780
gacctgaaca acctggtcat caccagggat gaaaacgaga actggaata ctatgagaag       840
ttccagatca tcgaaaacgt gtttaagcag aagaaaaagc ctacactgaa acagattgct     900
aaggagatcc tggtcaacga gaggacatc aagggctacc gggtgacaag cactggaaaa       960
ccagagttca ccaatctgaa agtgtatcac gatattaagg acatcacagc acggaaagaa    1020
atcattgaga cgccgaact gctggatcag attgctaaga tcctgactat ctaccagagc      1080
tccgaggaca tccaggaaga gctgactaac ctgaacagcg agctgaccca ggaagagatc    1140
gaacagatta gtaatctgaa ggggtacacc ggaacacaca acctgtccct gaaagctatc    1200
aatctgattc tggatgagct gtggcataca aacgacaatc agattgcaat ctttaaccgg    1260
ctgaagctgg tcccaaaaaa ggtggacctg agtcagcaga aagagatccc aaccacactg    1320
gtggacgatt tcattctgtc acccgtggtc aagcggagct tcatccagag catcaaagtg    1380
atcaacgcca tcatcaagaa gtacggcctg cccaatgata tcattatcga gctggctagg    1440
gagaagaaca gcaaggacgc acagaagatg atcaatgaga tgcagaaacg aaaccggcag    1500
accaatgaac gcattgaaga gattatccga actaccggga agagaacgc aaagtacctg      1560
attgaaaaaa tcaagctgca cgatatgcag gagggaaagt gtctgtattc tctggaggcc    1620
atcccctgg aggacctgct gaacaatcca ttcaactacg aggtcgatca tattatcccc      1680
agaagcgtgt ccttcgacaa ttcctttaac aacaaggtgc tggtcaagca ggaagagaac    1740
tctaaaaagg gcaataggac tccttttccag tacctgtcta gttcagattc caagatctct    1800
tacgaaacct ttaaaaagca cattctgaat ctggccaaag gaaagggccg catcagcaag    1860
accaaaaagg agtacctgct ggaagagcgg gacatcaaca gattctccgt ccagaaggat    1920
tttattaacc ggaatctggt ggacacaaga tacgctactc gcggcctgat gaatctgctg    1980
cgatcctatt tccgggtgaa caatctggat gtgaaagtca agtccatcaa cggcgggttc    2040
acatcttttc tgaggcgcaa atggaagttt aaaaaggagc gcaacaaagg gtacaagcac    2100
catgccgaag atgctctgat tatcgcaaat gccgacttca tctttaagga gtggaaaaag    2160
ctggacaaag ccaagaaagt gatggagaac cagatgttcg aagagaagca gnnnnnnnnn    2220
nnnnnnnnnn nnnnnnnnnn nnnnnnngcc gaatctatgc cgaaatcga cagaacag        2280
gagtacaagg agattttcat cactcctcac cagatcaagc atatcaagga tttcaaggac    2340
```

```
tacaagtact ctcaccgggt ggataaaaag cccaacagag agctgatcaa tgacaccctg   2400
tatagtacaa gaaagacga taagggaat accctgattg tgaacaatct gaacggactg    2460
tacgacaaag ataatgacaa gctgaaaaag ctgatcaaca aaagtcccga aagctgctg    2520 atgtaccacc atgatcctca gacatatcag aaactgaagc tgattatgga gcagtacggc  2580
gacgagaaga acccactgta taagtactat gaagagactg ggaactacct gaccaagtat  2640
agcaaaaagg ataatggccc cgtgatcaag aagatcaagt actatgggaa caagctgaat  2700
gcccatctgg acatcacaga cgattaccct aacagtcgca acaaggtggt caagctgtca  2760
ctgaagccat acagattcga tgtctatctg gacaacggcg tgtataaatt tgtgactgtc  2820
aagaatctgg atgtcatcaa aaaggagaac tactatgaag tgaatagcaa gtgctacgaa  2880
gaggctaaaa agctgaaaaa gattagcaac caggcagagt tcatcgcctc ctttttacaac  2940 aacgacctga ttaagatcaa tggcgaactg tatagggtca tcggggtgaa caatgatctg  3000
ctgaaccgca ttgaagtgaa tatgattgac atcacttacc gagagtatct ggaaaacatg  3060
aatgataagc gccccctcg aattatcaaa acaattgcct ctaagactca gagtatcaaa   3120
aagtactcaa ccgacattct gggaaacctg tatgaggtga agagcaaaaa gcaccctcag  3180
attatcaaaa agggc                                                   3195
```

<210> SEQ ID NO 10
<211> LENGTH: 1075
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (13)..(22)
<223> OTHER INFORMATION: Xaa can be any naturally occurring amino acid

<400> SEQUENCE: 10

```
Met Gly Pro Lys Lys Arg Lys Val Glu Ala Ser Xaa Xaa Xaa Xaa
1               5                  10                  15

Xaa Xaa Xaa Xaa Xaa Xaa Met Lys Arg Asn Tyr Ile Leu Gly Leu Asp
                20                  25                  30

Ile Gly Ile Thr Ser Val Gly Tyr Gly Ile Ile Asp Tyr Glu Thr Arg
            35                  40                  45

Asp Val Ile Asp Ala Gly Val Arg Leu Phe Lys Glu Ala Asn Val Glu
        50                  55                  60

Asn Asn Glu Gly Arg Arg Ser Lys Arg Gly Ala Arg Arg Leu Lys Arg
65                  70                  75                  80

Arg Arg Arg His Arg Ile Gln Arg Val Lys Lys Leu Leu Phe Asp Tyr
                85                  90                  95

Asn Leu Leu Thr Asp His Ser Glu Leu Ser Gly Ile Asn Pro Tyr Glu
            100                 105                 110

Ala Arg Val Lys Gly Leu Ser Gln Lys Leu Ser Glu Glu Phe Ser
        115                 120                 125

Ala Ala Leu Leu His Leu Ala Lys Arg Arg Gly Val His Asn Val Asn
130                 135                 140

Glu Val Glu Glu Asp Thr Gly Asn Glu Leu Ser Thr Lys Glu Gln Ile
145                 150                 155                 160

Ser Arg Asn Ser Lys Ala Leu Glu Glu Lys Tyr Val Ala Glu Leu Gln
                165                 170                 175

Leu Glu Arg Leu Lys Lys Asp Gly Glu Val Arg Gly Ser Ile Asn Arg
            180                 185                 190
```

```
Phe Lys Thr Ser Asp Tyr Val Lys Glu Ala Lys Gln Leu Leu Lys Val
    195                 200                 205

Gln Lys Ala Tyr His Gln Leu Asp Gln Ser Phe Ile Asp Thr Tyr Ile
210                 215                 220

Asp Leu Leu Glu Thr Arg Arg Thr Tyr Glu Gly Pro Gly Glu Gly
225                 230                 235                 240

Ser Pro Phe Gly Trp Lys Asp Ile Lys Glu Trp Tyr Glu Met Leu Met
                245                 250                 255

Gly His Cys Thr Tyr Phe Pro Glu Glu Leu Arg Ser Val Lys Tyr Ala
                260                 265                 270

Tyr Asn Ala Asp Leu Tyr Asn Ala Leu Asn Asp Leu Asn Asn Leu Val
            275                 280                 285

Ile Thr Arg Asp Glu Asn Glu Lys Leu Glu Tyr Tyr Glu Lys Phe Gln
        290                 295                 300

Ile Ile Glu Asn Val Phe Lys Gln Lys Lys Pro Thr Leu Lys Gln
305                 310                 315                 320

Ile Ala Lys Glu Ile Leu Val Asn Glu Glu Asp Ile Lys Gly Tyr Arg
                325                 330                 335

Val Thr Ser Thr Gly Lys Pro Glu Phe Thr Asn Leu Lys Val Tyr His
                340                 345                 350

Asp Ile Lys Asp Ile Thr Ala Arg Lys Glu Ile Ile Glu Asn Ala Glu
            355                 360                 365

Leu Leu Asp Gln Ile Ala Lys Ile Leu Thr Ile Tyr Gln Ser Ser Glu
        370                 375                 380

Asp Ile Gln Glu Glu Leu Thr Asn Leu Asn Ser Glu Leu Thr Gln Glu
385                 390                 395                 400

Glu Ile Glu Gln Ile Ser Asn Leu Lys Gly Tyr Thr Gly Thr His Asn
                405                 410                 415

Leu Ser Leu Lys Ala Ile Asn Leu Ile Leu Asp Glu Leu Trp His Thr
                420                 425                 430

Asn Asp Asn Gln Ile Ala Ile Phe Asn Arg Leu Lys Leu Val Pro Lys
            435                 440                 445

Lys Val Asp Leu Ser Gln Gln Lys Glu Ile Pro Thr Thr Leu Val Asp
        450                 455                 460

Asp Phe Ile Leu Ser Pro Val Val Lys Arg Ser Phe Ile Gln Ser Ile
465                 470                 475                 480

Lys Val Ile Asn Ala Ile Ile Lys Lys Tyr Gly Leu Pro Asn Asp Ile
                485                 490                 495

Ile Ile Glu Leu Ala Arg Glu Lys Asn Ser Lys Asp Ala Gln Lys Met
                500                 505                 510

Ile Asn Glu Met Gln Lys Arg Asn Arg Gln Thr Asn Glu Arg Ile Glu
            515                 520                 525

Glu Ile Ile Arg Thr Thr Gly Lys Glu Asn Ala Lys Tyr Leu Ile Glu
        530                 535                 540

Lys Ile Lys Leu His Asp Met Gln Glu Gly Lys Cys Leu Tyr Ser Leu
545                 550                 555                 560

Glu Ala Ile Pro Leu Glu Asp Leu Leu Asn Asn Pro Phe Asn Tyr Glu
                565                 570                 575

Val Asp His Ile Ile Pro Arg Ser Val Ser Phe Asp Asn Ser Phe Asn
                580                 585                 590

Asn Lys Val Leu Val Lys Gln Glu Glu Asn Ser Lys Lys Gly Asn Arg
            595                 600                 605
```

```
Thr Pro Phe Gln Tyr Leu Ser Ser Asp Ser Lys Ile Ser Tyr Glu
    610                 615                 620

Thr Phe Lys Lys His Ile Leu Asn Leu Ala Lys Gly Lys Gly Arg Ile
625                 630                 635                 640

Ser Lys Thr Lys Lys Glu Tyr Leu Leu Glu Glu Arg Asp Ile Asn Arg
                645                 650                 655

Phe Ser Val Gln Lys Asp Phe Ile Asn Arg Asn Leu Val Asp Thr Arg
                660                 665                 670

Tyr Ala Thr Arg Gly Leu Met Asn Leu Leu Arg Ser Tyr Phe Arg Val
            675                 680                 685

Asn Asn Leu Asp Val Lys Val Lys Ser Ile Asn Gly Gly Phe Thr Ser
    690                 695                 700

Phe Leu Arg Arg Lys Trp Lys Phe Lys Lys Glu Arg Asn Lys Gly Tyr
705                 710                 715                 720

Lys His His Ala Glu Asp Ala Leu Ile Ile Ala Asn Ala Asp Phe Ile
                725                 730                 735

Phe Lys Glu Trp Lys Lys Leu Asp Lys Ala Lys Lys Val Met Glu Asn
                740                 745                 750

Gln Met Phe Glu Glu Lys Gln Ala Glu Ser Met Pro Glu Ile Glu Thr
        755                 760                 765

Glu Gln Glu Tyr Lys Glu Ile Phe Ile Thr Pro His Gln Ile Lys His
    770                 775                 780

Ile Lys Asp Phe Lys Asp Tyr Lys Tyr Ser His Arg Val Asp Lys Lys
785                 790                 795                 800

Pro Asn Arg Glu Leu Ile Asn Asp Thr Leu Tyr Ser Thr Arg Lys Asp
                805                 810                 815

Asp Lys Gly Asn Thr Leu Ile Val Asn Asn Leu Asn Gly Leu Tyr Asp
                820                 825                 830

Lys Asp Asn Asp Lys Leu Lys Lys Leu Ile Asn Lys Ser Pro Glu Lys
            835                 840                 845

Leu Leu Met Tyr His His Asp Pro Gln Thr Tyr Gln Lys Leu Lys Leu
    850                 855                 860

Ile Met Glu Gln Tyr Gly Asp Glu Lys Asn Pro Leu Tyr Lys Tyr Tyr
865                 870                 875                 880

Glu Glu Thr Gly Asn Tyr Leu Thr Lys Tyr Ser Lys Lys Asp Asn Gly
                885                 890                 895

Pro Val Ile Lys Lys Ile Lys Tyr Tyr Gly Asn Lys Leu Asn Ala His
            900                 905                 910

Leu Asp Ile Thr Asp Asp Tyr Pro Asn Ser Arg Asn Lys Val Val Lys
        915                 920                 925

Leu Ser Leu Lys Pro Tyr Arg Phe Asp Val Tyr Leu Asp Asn Gly Val
    930                 935                 940

Tyr Lys Phe Val Thr Val Lys Asn Leu Asp Val Ile Lys Lys Glu Asn
945                 950                 955                 960

Tyr Tyr Glu Val Asn Ser Lys Cys Tyr Glu Ala Lys Lys Leu Lys
                965                 970                 975

Lys Ile Ser Asn Gln Ala Glu Phe Ile Ala Ser Phe Tyr Asn Asn Asp
            980                 985                 990

Leu Ile Lys Ile Asn Gly Glu Leu Tyr Arg Val Ile Gly Val Asn Asn
        995                 1000                1005

Asp Leu Leu Asn Arg Ile Glu Val Asn Met Ile Asp Ile Thr Tyr
        1010                1015                1020

Arg Glu Tyr Leu Glu Asn Met Asn Asp Lys Arg Pro Pro Arg Ile
```

-continued

```
          1025                1030                1035
Ile Lys Thr Ile Ala Ser Lys Thr Gln Ser Ile Lys Lys Tyr Ser
        1040                1045                1050

Thr Asp Ile Leu Gly Asn Leu Tyr Glu Val Lys Ser Lys Lys His
        1055                1060                1065

Pro Gln Ile Ile Lys Lys Gly
        1070            1075

<210> SEQ ID NO 11
<211> LENGTH: 3225
<212> TYPE: DNA
<213> ORGANISM: Artificial Sequence
<220> FEATURE:
<223> OTHER INFORMATION: Synthetic nucleic acid
<220> FEATURE:
<221> NAME/KEY: misc_feature
<222> LOCATION: (37)..(66)
<223> OTHER INFORMATION: n is a, c, g, or t

<400> SEQUENCE: 11
atgggaccga agaaaaagcg caaggtcgaa gcgtccnnnn nnnnnnnnnn nnnnnnnnnn     60
nnnnnnatga aaaggaacta cattctgggg ctggacatcg ggattacaag cgtggggtat   120
gggattattg actatgaaac aagggacgtg atcgacgcag gcgtcagact gttcaaggag   180
gccaacgtgg aaaacaatga gggacggaga agcaagaggg gagccaggcg cctgaaacga   240
cggagaaggc acagaatcca gagggtgaag aaactgctgt tcgattacaa cctgctgacc   300
gaccattctg agctgagtgg aattaatcct tatgaagcca gggtgaaagg cctgagtcag   360
aagctgtcag aggaagagtt ttccgcagct ctgctgcacc tggctaagcg ccgaggagtg   420
cataacgtca atgaggtgga agaggacacc ggcaacgagc tgtctacaaa ggaacagatc   480
tcacgcaata gcaaagctct ggaagagaag tatgtcgcag agctgcagct ggaacggctg   540
aagaaagatg cgaggtgag agggtcaatt aataggttca agacaagcga ctacgtcaaa   600
gaagccaagc agctgctgaa agtgcagaag gcttaccacc agctggatca gagcttcatc   660
gatacttata tcgacctgct ggagactcgg agaacctact atgagggacc aggagaaggg   720
agccccttcg gatggaaaga catcaaggaa tggtacgaga tgctgatggg acattgcacc   780
tattttccag aagagctgag aagcgtcaag tacgcttata cgcagatctg gtacaacgcc   840
ctgaatgacc tgaacaacct ggtcatcacc agggatgaaa acgagaaact ggaatactat   900
gagaagttcc agatcatcga aaacgtgttt aagcagaaga aaaagcctac actgaaacag   960
attgctaagg atcctggtc caacgaagag gacatcaagg gctaccgggt gacaagcact  1020
ggaaaaccag agttcaccaa tctgaaagtg tatcacgata ttaaggacat cacagcacgg  1080
aaagaaatca ttgagaacgc cgaactgctg gatcagattg ctaagatcct gactatctac  1140
cagagctccg aggacatcca ggaagagctg actaacctga cagcgagct gacccaggaa  1200 gagatcgaac agattagtaa tctgaagggg tacaccggaa cacacaacct gtccctgaaa  1260
gctatcaatc tgattctgga tgagctgtgg catacaaacg acaatcagat tgcaatcttt  1320
aaccggctga gctggtccc aaaaaaggtg gacctgagtc agcagaaaga gatcccaacc  1380
acactggtgg acgatttcat tctgtcaccc gtggtcaagc ggagcttcat ccagagcatc  1440
aaagtgatca acgccatcat caagaagtac ggcctgccca tgatatcat tatcgagctg  1500 gctaggagag agaacagcaa ggacgcacag aagatgatca atgagatgca gaaacgaaac  1560
cggcagacca atgaacgcat tgaagagatt atccgaacta ccgggaaaga gaacgcaaag  1620
```

-continued

```
tacctgattg aaaaaatcaa gctgcacgat atgcaggagg gaaagtgtct gtattctctg    1680
gaggccatcc ccctggagga cctgctgaac aatccattca actacgaggt cgatcatatt    1740
atccccagaa gcgtgtcctt cgacaattcc tttaacaaca aggtgctggt caagcaggaa    1800
gagaactcta aaagggcaa taggactcct ttccagtacc tgtctagttc agattccaag    1860
atctcttacg aaacctttaa aaagcacatt ctgaatctgg ccaaaggaaa gggccgcatc    1920
agcaagacca aaaaggagta cctgctggaa gagcgggaca tcaacagatt ctccgtccag    1980
aaggatttta ttaaccggaa tctggtggac acaagatacg ctactcgcgg cctgatgaat    2040
ctgctgcgat cctatttccg ggtgaacaat ctggatgtga agtcaagtc catcaacggc    2100 gggttcacat ctttctgag gcgcaaatgg aagtttaaaa aggagcgcaa caaagggtac    2160
aagcaccatg ccgaagatgc tctgattatc gcaaatgccg acttcatctt taaggagtgg    2220
aaaaagctgg acaaagccaa gaaagtgatg agaaccaga tgttcgaaga aagcaggcc    2280 gaatctatgc ccgaaatcga cagaacag gagtacaagg agatttcat cactcctcac    2340 cagatcaagc atatcaagga tttcaaggac tacaagtact ctcaccgggt ggataaaaag    2400
cccaacagag agctgatcaa tgacaccctg tatagtacaa gaaaagacga taaggggaat    2460
accctgattg tgaacaatct gaacggactg tacgacaaag ataatgacaa gctgaaaaag    2520
ctgatcaaca aaagtcccga gaagctgctg atgtaccacc atgatcctca gacatatcag    2580
aaactgaagc tgattatgga gcagtacggc gacgagaaga acccactgta taagtactat    2640
gaagagactg ggaactacct gaccaagtat agcaaaaagg ataatggccc cgtgatcaag    2700
aagatcaagt actatgggaa caagctgaat gcccatctgg acatcacaga cgattacccct    2760 aacagtcgca acaaggtggt caagctgtca ctgaagccat acagattcga tgtctatctg    2820
gacaacggcg tgtataaatt tgtgactgtc aagaatctgg atgtcatcaa aaaggagaac    2880
tactatgaag tgaatagcaa gtgctacgaa gaggctaaaa agctgaaaaa gattagcaac    2940
caggcagagt tcatcgcctc cttttacaac aacgacctga ttaagatcaa tggcgaactg    3000
tatagggtca tcgggggtgaa caatgatctg ctgaaccgca ttgaagtgaa tatgattgac    3060
atcacttacc gagagtatct ggaaaacatg aatgataagc gcccccctcg aattatcaaa    3120
acaattgcct ctaagactca gagtatcaaa aagtactcaa ccgacattct gggaaacctg    3180
tatgaggtga agagcaaaaa gcaccctcag attatcaaaa agggc                    3225
```

<210> SEQ ID NO 12
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 12

```
Gly Pro Lys Lys Lys Arg Lys Val Glu Ala Ser
1               5                   10
```

<210> SEQ ID NO 13
<211> LENGTH: 1307
<212> TYPE: PRT
<213> ORGANISM: Artificial Sequence
<220> FEATURE:
<223> OTHER INFORMATION: Synthetic polypeptide

<400> SEQUENCE: 13

```
Met Thr Gln Phe Glu Gly Phe Thr Asn Leu Tyr Gln Val Ser Lys Thr
1               5                   10                  15
```

```
Leu Arg Phe Glu Leu Ile Pro Gln Gly Lys Thr Leu Lys His Ile Gln
            20                  25                  30

Glu Gln Gly Phe Ile Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
 50                  55                  60

Cys Leu Gln Leu Val Gln Leu Asp Trp Glu Asn Leu Ser Ala Ala Ile
 65                  70                  75                  80

Asp Ser Tyr Arg Lys Glu Lys Thr Glu Thr Arg Asn Ala Leu Ile
                85                  90                  95

Glu Glu Gln Ala Thr Tyr Arg Asn Ala Ile His Asp Tyr Phe Ile Gly
                100                 105                 110

Arg Thr Asp Asn Leu Thr Asp Ala Ile Asn Lys Arg His Ala Glu Ile
                115                 120                 125

Tyr Lys Gly Leu Phe Lys Ala Glu Leu Phe Asn Gly Lys Val Leu Lys
130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
                180                 185                 190

Ile Val Gln Asp Asn Phe Pro Lys Phe Lys Glu Asn Cys His Ile Phe
                195                 200                 205

Thr Arg Leu Ile Thr Ala Val Pro Ser Leu Arg Glu His Phe Glu Asn
                210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
                260                 265                 270

Lys Ile Lys Gly Leu Asn Glu Val Leu Asn Leu Ala Ile Gln Lys Asn
                275                 280                 285

Asp Glu Thr Ala His Ile Ile Ala Ser Leu Pro His Arg Phe Ile Pro
                290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
                340                 345                 350

Phe Asn Glu Leu Asn Ser Ile Asp Leu Thr His Ile Phe Ile Ser His
                355                 360                 365

Lys Lys Leu Glu Thr Ile Ser Ser Ala Leu Cys Asp His Trp Asp Thr
                370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
                420                 425                 430
```

-continued

```
Glu Ala Phe Lys Gln Lys Thr Ser Glu Ile Leu Ser His Ala His Ala
            435                 440                 445

Ala Leu Asp Gln Pro Leu Pro Thr Thr Leu Lys Lys Gln Glu Glu Lys
450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
            515                 520                 525

Glu Lys Phe Lys Leu Asn Phe Gln Met Pro Thr Leu Ala Ser Gly Trp
        530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
            580                 585                 590

Met Tyr Tyr Asp Tyr Phe Pro Asp Ala Ala Lys Met Ile Pro Lys Cys
            595                 600                 605

Ser Thr Gln Leu Lys Ala Val Thr Ala His Phe Gln Thr His Thr Thr
            610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
            660                 665                 670

Leu Cys Lys Trp Ile Asp Phe Thr Arg Asp Phe Leu Ser Lys Tyr Thr
        675                 680                 685

Lys Thr Thr Ser Ile Asp Leu Ser Ser Leu Arg Pro Ser Ser Gln Tyr
690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
            740                 745                 750

Gly His His Gly Lys Pro Asn Leu His Thr Leu Tyr Trp Thr Gly Leu
        755                 760                 765

Phe Ser Pro Glu Asn Leu Ala Lys Thr Ser Ile Lys Leu Asn Gly Gln
770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
                805                 810                 815

Pro Ile Pro Asp Thr Leu Tyr Gln Glu Leu Tyr Asp Tyr Val Asn His
            820                 825                 830

Arg Leu Ser His Asp Leu Ser Asp Glu Ala Arg Ala Leu Leu Pro Asn
        835                 840                 845

Val Ile Thr Lys Glu Val Ser His Glu Ile Ile Lys Asp Arg Arg Phe
```

```
                850                 855                 860
Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                885                 890                 895

Lys Glu His Pro Glu Thr Pro Ile Ile Gly Ile Asp Arg Gly Glu Arg
                900                 905                 910

Asn Leu Ile Tyr Ile Thr Val Ile Asp Ser Thr Gly Lys Ile Leu Glu
            915                 920                 925

Gln Arg Ser Leu Asn Thr Ile Gln Gln Phe Asp Tyr Gln Lys Lys Leu
        930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
                965                 970                 975

His Glu Ile Val Asp Leu Met Ile His Tyr Gln Ala Val Val Val Leu
            980                 985                 990

Ala Asn Leu Asn Phe Gly Phe Lys Ser Lys Arg Thr Gly Ile Ala Glu
        995                 1000                1005

Lys Ala Val Tyr Gln Gln Phe Glu Lys Met Leu Ile Asp Lys Leu
    1010                1015                1020

Asn Cys Leu Val Leu Lys Asp Tyr Pro Ala Glu Lys Val Gly Gly
    1025                1030                1035

Val Leu Asn Pro Tyr Gln Leu Thr Asp Gln Phe Thr Ser Phe Ala
    1040                1045                1050

Lys Met Gly Thr Gln Ser Gly Phe Leu Phe Tyr Val Pro Ala Pro
    1055                1060                1065

Tyr Thr Ser Lys Ile Asp Pro Leu Thr Gly Phe Val Asp Pro Phe
    1070                1075                1080

Val Trp Lys Thr Ile Lys Asn His Glu Ser Arg Lys His Phe Leu
    1085                1090                1095

Glu Gly Phe Asp Phe Leu His Tyr Asp Val Lys Thr Gly Asp Phe
    1100                1105                1110

Ile Leu His Phe Lys Met Asn Arg Asn Leu Ser Phe Gln Arg Gly
    1115                1120                1125

Leu Pro Gly Phe Met Pro Ala Trp Asp Ile Val Phe Glu Lys Asn
    1130                1135                1140

Glu Thr Gln Phe Asp Ala Lys Gly Thr Pro Phe Ile Ala Gly Lys
    1145                1150                1155

Arg Ile Val Pro Val Ile Glu Asn His Arg Phe Thr Gly Arg Tyr
    1160                1165                1170

Arg Asp Leu Tyr Pro Ala Asn Glu Leu Ile Ala Leu Leu Glu Glu
    1175                1180                1185

Lys Gly Ile Val Phe Arg Asp Gly Ser Asn Ile Leu Pro Lys Leu
    1190                1195                1200

Leu Glu Asn Asp Asp Ser His Ala Ile Asp Thr Met Val Ala Leu
    1205                1210                1215

Ile Arg Ser Val Leu Gln Met Arg Asn Ser Asn Ala Ala Thr Gly
    1220                1225                1230

Glu Asp Tyr Ile Asn Ser Pro Val Arg Asp Leu Asn Gly Val Cys
    1235                1240                1245

Phe Asp Ser Arg Phe Gln Asn Pro Glu Trp Pro Met Asp Ala Asp
    1250                1255                1260
```

| Ala | Asn | Gly | Ala | Tyr | His | Ile | Ala | Leu | Lys | Gly | Gln | Leu | Leu | Leu |
|  |  | 1265 |  |  | 1270 |  |  |  |  | 1275 |  |  |  |  |

| Asn | His | Leu | Lys | Glu | Ser | Lys | Asp | Leu | Lys | Leu | Gln | Asn | Gly | Ile |
|  | 1280 |  |  |  |  | 1285 |  |  |  |  | 1290 |  |  |  |

| Ser | Asn | Gln | Asp | Trp | Leu | Ala | Tyr | Ile | Gln | Glu | Leu | Arg | Asn |  |
| 1295 |  |  |  |  | 1300 |  |  |  |  | 1305 |  |  |  |  |

<210> SEQ ID NO 14
<211> LENGTH: 3921
<212> TYPE: DNA
<213> ORGANISM: Artificial Sequence
<220> FEATURE:
<223> OTHER INFORMATION: Synthetic nucleic acid

<400> SEQUENCE: 14

| atgacacagt tcgagggctt taccaacctg tatcaggtga gcaagacact gcggtttgag | 60 |
| ctgatcccac agggcaagac cctgaagcac atccaggagc agggcttcat cgaggaggac | 120 |
| aaggcccgca atgatcacta caaggagctg aagcccatca tcgatcggat ctacaagacc | 180 |
| tatgccgacc agtgcctgca gctggtgcag ctggattggg agaacctgag cgccgccatc | 240 |
| gactcctata gaaaggagaa accgaggag acaaggaacg ccctgatcga ggagcaggcc | 300 |
| acatatcgca atgccatcca cgactactttc atcggccgga cagacaacct gaccgatgcc | 360 |
| atcaataaga gacacgccga gatctacaag ggcctgttca aggccgagct gtttaatggc | 420 |
| aaggtgctga gcagctggg caccgtgacc acaaccgagc acgagaacgc cctgctgcgg | 480 |
| agcttcgaca gtttacaac ctacttctcc ggcttttatg agaacaggaa gaacgtgttc | 540 |
| agcgccgagg atatcagcac agccatccca caccgcatcg tgcaggacaa cttccccaag | 600 |
| tttaaggaga attgtcacat cttcacacgc tgatcaccg ccgtgcccag cctgcgggag | 660 |
| cactttgaga cgtgaagaa ggccatcggc atcttcgtga gcacctccat cgaggaggtg | 720 |
| ttttccttcc cttttataa ccagctgctg acacagaccc agatcgacct gtataaccag | 780 |
| ctgctgggag gaatctctcg ggaggcaggc accgagaaga tcaagggcct gaacgaggtg | 840 |
| ctgaatctgg ccatccagaa gaatgatgag acagcccaca tcatcgcctc cctgccacac | 900 |
| agattcatcc ccctgtttaa gcagatcctg tccgatagga cacccctgtc tttcatcctg | 960 |
| gaggagtta gagcgacga ggaagtgatc cagtccttct gcaagtacaa gacactgctg | 1020 |
| agaaacgaga acgtgctgga gacagccgag gccctgttta cgagctgaa cagcatcgac | 1080 |
| ctgacacaca tcttcatcag ccacaagaag ctggagacaa tcagcagcgc cctgtgcgac | 1140 |
| cactgggata cactgaggaa tgccctgtat gagcggagaa tctccgagct gacaggcaag | 1200 |
| atcaccaagt ctgccaagga aaggtgcag cgcagcctga gcacgagga tatcaacctg | 1260 |
| caggagatca tctctgccgc aggcaaggag ctgagcgagg ccttcaagca gaaaaccagc | 1320 |
| gagatcctgt cccacgcaca cgccgccctg gatcagccac tgcctacaac cctgaagaag | 1380 |
| caggaggaga aggagatcct gaagtctcag ctggacagcc tgctgggcct gtaccacctg | 1440 |
| ctggactggt tgccgtgga tgagtccaac gaggtggacc ccgagttctc tgcccggctg | 1500 |
| accggcatca gctggagat ggagccttct ctgagcttct acaacaaggc cagaaattat | 1560 |
| gccaccaaga agccctactc cgtggagaag ttcaagctga ctttcagat gcctacactg | 1620 |
| gcctctggct gggacgtgaa taaggagaag aacaatggcg ccatcctgtt tgtgaagaac | 1680 |
| ggcctgtact atctgggcat catgccaaag cagaagggca ggtataaggc cctgagcttc | 1740 |
| gagcccacag agaaaaccag cgagggcttt gataagatgt actatgacta cttccctgat | 1800 |

-continued

```
gccgccaaga tgatcccaaa gtgcagcacc cagctgaagg ccgtgacagc ccactttcag    1860
acccacacaa ccccatcct gctgtccaac aatttcatcg agcctctgga gatcacaaag     1920
gagatctacg acctgaacaa tcctgagaag gagccaaaga agtttcagac agcctacgcc    1980
aagaaaaccg cgaccagaa gggctacaga gaggccctgt gcaagtggat cgacttcaca     2040 agggatttc tgtccaagta taccaagaca acctctatcg atctgtctag cctgcggcca     2100
tcctctcagt ataaggacct gggcgagtac tatgccgagc tgaatcccct gctgtaccac    2160
atcagcttcc agagaatcgc cgagaaggag atcatggatg ccgtggagac aggcaagctg    2220
tacctgttcc agatctataa caaggacttt gccaagggcc accacggcaa gcctaatctg    2280
cacacactgt attggaccgg cctgttttct ccagagaacc tggccaagac aagcatcaag    2340
ctgaatggcc aggccgagct gttctaccgc cctaagtcca ggatgaagag gatggcacac    2400
cggctgggag agaagatgct gaacaagaag ctgaaggatc agaaaacccc aatccccgac    2460
accctgtacc aggagctgta cgactatgtg aatcacagac tgtcccacga cctgtctgat    2520
gaggccaggg ccctgctgcc caacgtgatc accaaggagg tgtctcacga gatcatcaag    2580
gataggcgct ttaccagcga caagttcttt ttccacgtgc ctatcacact gaactatcag    2640
gccgccaatt ccccatctaa gttcaaccag agggtgaatg cctacctgaa ggagcacccc    2700
gagacaccta tcatcggcat cgatcgggc gagagaaacc tgatctatat cacagtgatc    2760
gactccaccg gcaagatcct ggagcagcgg agcctgaaca ccatccagca gtttgattac    2820
cagaagaagc tggacaacag ggagaaggag agggtggcag caaggcaggc ctggtctgtg    2880
gtgggcacaa tcaaggatct gaagcagggc tatctgagcc aggtcatcca cgagatcgtg    2940
gacctgatga tccactacca ggccgtggtg gtgctggcga acctgaattt cggctttaag    3000
agcaagagga ccggcatcgc cgagaaggcc gtgtaccagc agttcgagaa gatgctgatc    3060
gataagctga attgcctggt gctgaaggac tatccagcag agaaagtggg aggcgtgctg    3120
aacccatacc agctgacaga ccagttcacc tcctttgcca gatgggcac ccagtctggc     3180 ttcctgtttt acgtgcctgc cccatataca tctaagatcg atcccctgac cggcttcgtg    3240 gacccttcg tgtggaaaac catcaagaat cacgagagcc gcaagcactt cctggagggc     3300
ttcgactttc tgcactacga cgtgaaaacc ggcgacttca tcctgcactt taagatgaac    3360
agaaatctgt ccttccagag gggcctgccc ggctttatgc ctgcatggga tatcgtgttc    3420
gagaagaacg agacacagtt tgacgccaag ggcaccccctt tcatcgccgg caagagaatc    3480
gtgccagtga tcgagaatca cagattcacc ggcagatacc gggacctgta tcctgccaac    3540
gagctgatcg ccctgctgga ggagaagggc atcgtgttca gggatggctc caacatcctg    3600
ccaaagctgc tggagaatga cgattctcac gccatcgaca ccatggtggc cctgatccgc    3660
agcgtgctgc agatgcggaa ctccaatgcc gccacaggcg aggactatat caacagcccc    3720
gtgcgcgatc tgaatggcgt gtgcttcgac tcccggtttc agaacccaga gtggcccatg    3780
gacgccgatg ccaatggcgc ctaccacatc gccctgaagg gccagctgct gctgaatcac    3840
ctgaaggaga gcaaggatct gaagctgcag aacggcatct ccaatcagga ctggctggcc    3900
tacatccagg agctgcgcaa c                                              3921
```

<210> SEQ ID NO 15
<211> LENGTH: 22
<212> TYPE: DNA
<213> ORGANISM: Artificial Sequence
<220> FEATURE:

<223> OTHER INFORMATION: Synthetic nucleic acid

<400> SEQUENCE: 15
aagctgcgtg agacatgtgt tt                                           22

<210> SEQ ID NO 16
<211> LENGTH: 20
<212> TYPE: DNA
<213> ORGANISM: Artificial Sequence
<220> FEATURE:
<223> OTHER INFORMATION: Synthetic nucleic acid

<400> SEQUENCE: 16
agctatctgt agcatgctga                                              20

<210> SEQ ID NO 17
<211> LENGTH: 22
<212> TYPE: DNA
<213> ORGANISM: Artificial Sequence
<220> FEATURE:
<223> OTHER INFORMATION: Synthetic nucleic acid

<400> SEQUENCE: 17
aaggctgtag cgatgctcac tg                                           22

<210> SEQ ID NO 18
<211> LENGTH: 22
<212> TYPE: DNA
<213> ORGANISM: Artificial Sequence
<220> FEATURE:
<223> OTHER INFORMATION: Synthetic nucleic acid

<400> SEQUENCE: 18
gtgtgccagc tggcggtata gg                                           22

<210> SEQ ID NO 19
<211> LENGTH: 22
<212> TYPE: DNA
<213> ORGANISM: Artificial Sequence
<220> FEATURE:
<223> OTHER INFORMATION: Synthetic nucleic acid

<400> SEQUENCE: 19
gtcaaaagct accggttacc tg                                           22

<210> SEQ ID NO 20
<211> LENGTH: 22
<212> TYPE: DNA
<213> ORGANISM: Artificial Sequence
<220> FEATURE:
<223> OTHER INFORMATION: Synthetic nucleic acid

<400> SEQUENCE: 20
gttctgtcct cagtaaaagg ta                                           22

<210> SEQ ID NO 21
<211> LENGTH: 24
<212> TYPE: DNA
<213> ORGANISM: Artificial Sequence
<220> FEATURE:
<223> OTHER INFORMATION: Synthetic nucleic acid

<400> SEQUENCE: 21
caatagggat aggtatgaga tact                                         24